United States Patent
Lu et al.

(10) Patent No.: US 12,377,162 B2
(45) Date of Patent: Aug. 5, 2025

(54) ANTI-SERINE PROTEASE INHIBITOR KAZAL (SPIK) ANTIBODIES, IMMUNOCONJUGATES, AND METHODS OF USE

(71) Applicant: IMCARE BIOTECH, LLC, Doylestown, PA (US)

(72) Inventors: Xuanyong Lu, Horsham, PA (US); Felix Lu, Burbank, CA (US)

(73) Assignee: ImCare Biotech, LLC, Doylestown, PA (US)

( * ) Notice: Subject to any disclaimer, the term of this patent is extended or adjusted under 35 U.S.C. 154(b) by 880 days.

(21) Appl. No.: 17/625,693

(22) PCT Filed: Jul. 8, 2020

(86) PCT No.: PCT/US2020/041228
§ 371 (c)(1),
(2) Date: Jan. 7, 2022

(87) PCT Pub. No.: WO2021/007338
PCT Pub. Date: Jan. 14, 2021

(65) Prior Publication Data
US 2022/0273810 A1    Sep. 1, 2022

Related U.S. Application Data

(60) Provisional application No. 62/871,565, filed on Jul. 8, 2019.

(51) Int. Cl.
| | | |
|---|---|---|
| *A61K 47/54* | (2017.01) | |
| *A61K 47/68* | (2017.01) | |
| *C07K 16/38* | (2006.01) | |
| *G01N 33/68* | (2006.01) | |

(52) U.S. Cl.
CPC ........ *A61K 47/6843* (2017.08); *A61K 47/542* (2017.08); *A61K 47/6817* (2017.08); *C07K 16/38* (2013.01); *G01N 33/6893* (2013.01); *G01N 2333/811* (2013.01); *G01N 2800/085* (2013.01); *G01N 2800/50* (2013.01)

(58) Field of Classification Search
None
See application file for complete search history.

(56) References Cited

U.S. PATENT DOCUMENTS

| | | |
|---|---|---|
| 4,816,567 A | 3/1989 | Cabilly et al. |
| 4,975,278 A | 12/1990 | Senter et al. |
| 5,500,362 A | 3/1996 | Robinson et al. |
| 5,641,870 A | 6/1997 | Rinderknecht et al. |
| 5,767,237 A | 6/1998 | Sakakibara et al. |
| 5,821,337 A | 10/1998 | Carter et al. |
| 6,124,431 A | 9/2000 | Sakakibara et al. |
| 6,248,564 B1 | 6/2001 | Walter et al. |
| 8,362,213 B2 | 1/2013 | Elkins et al. |
| 2004/0018194 A1 | 1/2004 | Francisco et al. |
| 2005/0238649 A1 | 10/2005 | Doronina et al. |
| 2007/0092940 A1 | 4/2007 | Eigenbrot et al. |
| 2013/0280255 A1 | 10/2013 | Lu et al. |
| 2014/0308657 A1 | 10/2014 | Lu et al. |
| 2017/0067908 A1 | 3/2017 | Nakai et al. |
| 2019/0194327 A1 | 6/2019 | Cohen et al. |
| 2023/0192830 A1 | 6/2023 | Carter et al. |

FOREIGN PATENT DOCUMENTS

| | | | |
|---|---|---|---|
| CN | 102369218 A | | 3/2012 |
| CN | 104994875 A | | 10/2015 |
| CN | 105968209 A | | 9/2016 |
| CN | 109678950 A | | 4/2019 |
| EP | 1391213 A1 | | 2/2004 |
| WO | 02/088172 A2 | | 11/2002 |
| WO | 03/043583 A2 | | 5/2003 |
| WO | 2004/032828 A2 | | 2/2004 |
| WO | 2009052628 A1 | | 4/2009 |
| WO | 2011102999 A2 | | 8/2011 |
| WO | 2012078752 A2 | | 6/2012 |
| WO | 2014127200 A1 | | 8/2014 |
| WO | 2017172990 A1 | | 10/2017 |
| WO | 2019173503 A2 | | 9/2019 |
| WO | 2021007338 A1 | | 1/2021 |

OTHER PUBLICATIONS

Lamontagne et al. Hepatitis B and Hepatitis C Virus Replication Upregulates Serine Protease Inhibitor Kazal, Resulting in Cellular Resistance to Serine Protease-Dependent Apoptosis, J Virol 84(2): 907-917 (2010). (Year: 2010).*

Lu et al. Role of the inflammatory protein serine protease inhibitor Kazal in preventing cytolytic granule granzyme A-mediated apoptosis. Immunology, 134(4), 398-408 (2011). (Year: 2011).*

(Continued)

*Primary Examiner* — Daniel E Kolker
*Assistant Examiner* — Julia A Rossi
(74) *Attorney, Agent, or Firm* — Haynes and Boone LLP

(57) ABSTRACT

Anti-AS-SPIK antibodies are disclosed, along with methods of making such antibodies, compositions, including pharmaceutical compositions, comprising such antibodies, and their use to diagnose and/or treat disorders characterized by the expression of AS-SPIK (e.g., liver cancer). Diagnostic methods and kits comprising the anti-AS-SPIK antibodies are also disclosed.

20 Claims, 21 Drawing Sheets
Specification includes a Sequence Listing.

(56) References Cited

OTHER PUBLICATIONS

Kuwabara I., et al., "Epitope Mapping by Phage Display," Japanese Journal of Thrombosis and Hemostasis, 1998, vol. 9, No. 3, pp. 166-175.

Yamada N., "Peptide and Protein Epitope Mapping by Mass Spectrometry," Journal of the Mass Spectrometry Society of Japan, 1997, vol. 45, No. 3, pp. 355-366.

Anonymous., "A Novel Diagnostic Biomarker for Hepatocellular Carcinoma (HCC)," Jan. 1, 2016, Retrieved from the Internet URL: https://www.sbir.gov/sbirsearch/detail/10460.

Ateeq et al., Therapeutic Targeting of Spinkl-positive Prostate Cancer, Science (2011), Translational Medicine, vol. 3(72):72ra17-72ra17.

Bartelt D.C., et al., "The Primary Structure of the Human Pancreatic Secretory Trypsin Inhibitor: Amino Acid Sequence of the Reduced S-Aminoethylated Protein," Archives of biochemistry and biophysics, 1977, vol. 179, No. 1, pp. 189-199.

Bendtsen J.D., et al., "Improved Prediction of Signal Peptides: SignalP 3.0," Journal of Molecular Biology, Jul. 16, 2004, vol. 340, pp. 783-795.

Bernhard S.L., et al., "Cysteine Analogs of Recombinant Barley Ribosome Inactivating Protein Form Antibody Conjugates with Enhanced Stability and Potency in vitro," Bioconjugate Chemistry, 1994, vol. 5, pp. 126-132.

Bruix J., et al., "Management of Hepatocellular Carcinoma," Hepatology, 2005, vol. 42, No. 5, pp. 1208-1236.

Clackson T., et al., "Making Antibody Fragments using Phage Display Libraries," Nature, 1991, vol. 352, pp. 624-628.

El-Serag H.B., "Hepatocellular Carcinoma," The New England Journal of Medicine, 2011, vol. 365, pp. 1118-1127.

Emini E.A., et al., "Antigenic Conservation and Divergence Between The Viral-Specific Proteins of Poliovirus Type 1 and Various Picornavirusesm," Virology, 1985, vol. 140, pp. 13-20.

Gouyer et al., Autocrine Induction of Invasion and Metastasis by Tumor-assisted Trypsin Inhibitor in Human Colon Cancer Cells, (2008) Oncogene, vol. 27(29):4024-4033.

Greene L.J., et al., "Human Pancreatic Secretory Trypsin Inhibitor," Methods in Enzymology, Academic Press, 1976, vol. 45, pp. 813-825.

Greene L.J., et al., "Pancreatic Exocrine Secretory Proteins," Journal of Surgical Oncology, 1975, vol. 7, No. 2, pp. 151-154.

Hecht H.J., et al., "Three-Dimensional Structure of a Recombinant Variant of Human Pancreatic Secretory Trypsin Inhibitor (Kazal type)," Journal of Molecular Biology, 1992, vol. 225, pp. 1095-1103.

Hirota M., et al., "The Role of Trypsin, Trypsin Inhibitor, and Trypsin Receptor In the Onset and Aggravation of Pancreatitis," Journal of Gastroenterol, 2006, vol. 41, pp. 832-836.

Horii A., et al., "Primary Structure of Human Pancreatic Secretory Trypsin Inhibitor (Psti) Gene," Biochemical and Biophysical Research Communications, 1987, vol. 149, No. 2, pp. 635-641.

Junutula J.R., et al., "Rapid Identification of Reactive Cysteine Residues for Site-Specific Labeling of Antibody-Fabs," Journal of Immunological Methods, 2008, vol. 332, pp. 41-52.

Kanno S., et al., "Assembling of Engineered Igg-Binding Protein on Gold Surface for Highly Oriented Antibody Immobilization," Journal of Biotechnology, 2000, vol. 76, pp. 207-214.

Kew M.C., et al., "Epidemiology of Chronic Hepatitis B Virus Infection, Hepatocellular Carcinoma, and Hepatitis B Virus-Induced Hepatocellular Carcinoma," Pathologie Biologie (Paris), 2010, vol. 58, No. 4, pp. 273-277.

Kikuchi N., et al., "Purification and Complete Amino Acid Sequence of Canine Pancreatic Secretory Trypsin Inhibitor," FEBS Letters, 1985, vol. 191, No. 2, pp. 269-272.

Klussman K., et al., "Secondary mAb-vcMMAE Conjugates Are Highly Sensitive Reporters of Antibody Internalization via the Lysosome Pathway," Bioconjugate Chemistry, 2004, vol. 15, No. 4, pp. 765-773.

Kobayashi K., et al., "Pancreatic Secretory Trypsin Inhibitor as a Diagnostic Marker for Adult-Onset Type II Citrullinemia," Hepatology, 1997, vol. 25, pp. 1160-1165.

Lambert J.M., "Drug-Conjugated Monoclonal Antibodies for the Treatment of Cancer," Current Opinion in Pharmacology, 2005, vol. 5, pp. 543-549.

Lee Y.C et al., "Overexpression of Tumour-Associated Trypsin Inhibitor (Tati) Enhances Tumour Growth and is Associated With Portal Vein Invasion, Early Recurrence and a Stage-Independent Prognostic Factor of Hepatocellular Carcinoma," European Journal of Cancer, 2007, vol. 43, pp. 736-744.

Liu J., et al., "Increasing GPX Activity of Imitating Enzyme by Chemically Modifying Antibody," Chinese Journal of Biochemistry and Molecular Biology, 1999, 15(3), pp. 444-447.

Lode H.N et al., "Targeted Therapy with a Novel Enediyene Antibiotic Calicheamicin Theta (I)1 Effectively Suppresses Growth and Dissemination of Liver Metastases In a Syngeneic Model of Murine Neuroblastoma," Cancer Research, 1998, vol. 58, pp. 2925-2928.

Lok A.S et al., "Management of Hepatitis B: 2000—Summary of a Workshop," Gastroenterology, 2001, vol. 120, No. 7, pp. 1828-1853.

Lu et al., "High Level Expression of Apoptosis Inhibitor in Hepatoma Cell Line Expressing Hepatitis B Virus," International Journal of Medical Sciences, 2005, vol. 2, pp. 30-35.

Mandler et al., "Modifications in Synthesis Strategy Improve the Yield and Efficacy of Geldanamycin-Herceptin Immunoconjugates," Bioconjugate Chemistry, 2002, 13(4), pp. 786-791.

Mandler et al., "Synthesis and Evaluation of Antiproliferative Activity of a Geldanamycin-herceptin," Bioorganic & Medicinal Chemistry Letters, 2000, vol. 10, pp. 1025-1028.

Marks et al., "By-passing Immunization: Human Antibodies From V-gene Libraries Displayed on Phage," Journal of Molecular Biology, 1991, vol. 222, pp. 581-597.

Niculescu-Duvaz et al., "Antibody-directed Enzyme Prodrug Therapy (ADEPT): a Review," Advanced Drug Delivery Reviews, Jul. 1997, 26(2-3), pp. 151-172.

Ohmachi Y et al., "Specific Expression of the Pancreatic-secretory-trypsin-inhibitor (PSTI) Gene in Hepatocellular Carcinoma," International Journal of Cancer, Nov. 1993, 55(5), pp. 728-734.

Playford R.J et al., "Influence of Inflammation and Atrophy on Pancreatic Secretory Trypsin Inhibitor Levels Within the Gastric Mucosa," Gastroenterology, 1994, vol. 106, pp. 735-741.

Pluckthun A., "Antibodies from Escherichia coli," The Pharmacology of Monoclonal Antibodies, Rosenburg and Moore eds., Springer-Verlag, New York, 1994, vol. 113, pp. 269-315.

Presta L.G., "Antibody Engineering," Current Opinion in Structural Biology, 1992, 2:593-596.

Qiu., et al., "Pharmacologic Preconditioning for Hepatic Ischemia-reperfusion Injury (A Review of the Literature)," Foreign Medicine Surgery, 2004, vol. 31(4), pp. 230-234.

Rasanen et al., "Emerging Roles of SPINK1 in Cancer," (2015), Clinical Chemistry, vol. 62(3), pp. 449-457.

Rowland et al., "Drug Localisation and Growth Inhibition Studies of Vindesine-Monoclonal Anti-CEA Conjugates in a Human Tumour Xenograft," Cancer Immunology, Immunotherapy, 1986, 21(3), pp. 183-187.

Scatchard G., "The Attractions of Proteins for Small Molecules an Ions," Annals of the New York Academy of Sciences, 1949, 51, pp. 660-672.

Soon et al., Combined Genomic and Phenotype Screening Reveals Secretory Factor SPINK1 as an Invasion and Survival Factor Associated with Patient Prognosis in Breast Cancer, (2011) Embo Molecular Medicine, vol. 3(8), pp. 451-464.

Timmerman et al., "Functional Reconstruction and Synthetic Mimicry of a Conformational Epitope Using CLIPS Technology," Journal of Molecular Recognition, 2007, 20(5), pp. 283-299.

Van Regenmortel., "Molecular Dissection of Protein Antigens and the Prediction of Epitopes," Chapter 1 in: Laboratory Techniques in Biochemistry and Molecular Biology, vol. 19, 1988, pp. 1-39.

Wu et al., "Arming Antibodies: Prospects and Challenges for Immunoconjugates," Nature Biotechnology, Sep. 2005, 23 (9), pp. 1137-1146.

(56) References Cited

OTHER PUBLICATIONS

Yanwei et al., "Expression of Human Genetically Engineered Single-chain Antibodies to Hepatitis C Virus NS_3 Protein," Chinese Journal of Hepatology, 2000, vol. 3, pp. 171-173.
Zapta et al., "Engineering Linear F(Ab')2 Fragments for Efficient Production in *Escherichia Coli* and Enhanced Antiproliferative Activity," Protein Engineering, 1995, 8(10), pp. 1057-1062.
Zhang et al., "Complete Disulfide Bond Assignment of a Recombinant Immunoglobulin G4 Monoclonal Antibody," Analytical Biochemistry, 2002, 311, pp. 1-9.
Saraswat et al., "Historical epidemiology of hepatitis C virus (HCV) in select countries—vol. 2," (2015) Journal of Viral Hepatitis 22 (Suppl 1):6-25.
El-Serag et al., "Epidemiology of Hepatocellular Carcinoma in the United States: Where Are We? Where Do We Go?" (2014) Hepatology 60(5):1767-1775.
Kanwal et al., "Surveillance for Hepatocellular Carcinoma: Can We Focus on the Mission?" (2015) Clinical Gastroenterology and Hepatology 13( 4):805-807.
El-Serag et al., "Surveillance for hepatocellular carcinoma: in whom and how?" (2011) Therapeutic Advances in Gastroenterology 4(1):5-10.
Yu et al., "CT and MRI Improve Detection of Hepatocellular Carcinoma, Compared With Ultrasound Alone, in Patients With Cirrhosis," (2011) Clinical Gastroenterology and Hepatology 9(2):161-167.
Bruix et al., "Management of hepatocellular carcinoma: an update," (2011) Hepatology 53(3):1020-1022.
Kohler et al., "Continuous cultures of fused cells secreting antibody of predefined specificity," (2005) The Journal of Immunology 174:2453-2455[Reprinted from (1975) Nature 256:495-497].
Morrison et al., "Chimeric human antibody molecules: mouse antigen-binding domains with human constant region domains," (1984) Proc Natl Acad Sci USA 81:6851-6855.
Jones et al., "Replacing the complementarity-determining regions in a human antibody with those from a mouse," (1986) Nature 321:522-525.
Riechmann et al., "Reshaping human antibodies for therapy," (1988) Nature 332:323-329.
Dai et al., "Chimeric Antigen Receptors Modified T-Cells for Cancer Therapy," (2016) Journal Natl Cancer Inst. 108(7): djv439.
Jackson et al., "Driving CAR T-cells forward," (2016) Nature Reviews Clinical Oncology 13:370-383.
Ravetch et al., "Fc Receptors," (1991) Annu Rev Immunol 9:457-492.
Clynes et al., "Fc receptors are required in passive and active immunity to melanoma," (1998) PNAS (USA) 95 (2):652-656.
Gazzano-Santoro et al., "A non-radioactive complement-dependent cytotoxicity assay for anti-CD20 monoclonal antibody," J Immunol Methods 202(2):163-171.
Lu et al., "Role of the inflammatory protein serine protease inhibitor Kazal in preventing cytolytic granule granzyme A-mediated apoptosis," (2011) Immunology 134(4):398-408.
Stenman, "Tumor-associated Trypsin Inhibitor," (2002) Clin Chem 48(8):1206-1209.
GenBank Accession No. M11949.1, "Human pancreatic secretory trypsin inhibitor (PSTI) mRNA, complete cds," available at https://www.ncbi.nlm.nih.gov/nuccore/M11949.1 (last visited Jul. 14, 2022).
GenBank Accession No. NM003122, "*Homo sapiens* serine peptidase inhibitor Kazal type 1 (SPINK1), transcript variant 2, mRNA," available at https://www.ncbi.nlm.nih.gov/nuccore/NM_003122 (Last Visited Jul. 14, 2022).
GenBank Accession No. BC025790 "*Homo sapiens* serine peptidase inhibitor, Kazal type 1, mRNA (cDNA clone MGC:34543 IMAGE:5225693), complete cds," available at https://www.ncbi.nlm.nih.gov/nuccore/BC025790 (Last Visited Jul. 14, 2022).
Huehls et al., "Bispecific T-cell engagers for cancer immunotherapy," (2015) Immunol Cell Biol 93(3):290-296.
Iri-Sofla et al., "Nanobody-based chimeric receptor gene integration in Jurkat cells mediated by PhiC31 integrase," (2011) Experimental Cell Research 317(18):2630-2641.
Jamnani et al., "T cells expressing VHH-directed oligoclonal chimeric HER2 antigen receptors: Towards tumor-directed oligoclonal T cell therapy," (2014) Biochim Biophys Acta, 1840(1):378-386.
Pardo et al., "Granzymes are essential for natural killer cell-mediated and perf-facilitated tumor control," (2002) Eur J Immunol 32(10):2881-2887.
Rothemberg, "Humanized Anti-IL-5 Antibody Therapy," (2016) Cell 165(3):509.
Kyte, "A simple method for displaying the hydropathic character of a protein," (1982) J Mol Biol 157(1):105-132.
Hopp et al., "Prediction of protein antigenic determinants from amino acid sequences," (1981) Proc Natl Acad Sci USA 78(6):3824-3828.
Hopp et al., "A computer program for predicting protein antigenic determinants," (1983) Mol Immunol 20(4):483-489.
Hopp, "Methods for identifying antigenic determinants and other interaction sites," (1986) J Immunol Methods 88 (1):1-18.
Jameson et al., "The antigenic index: a novel algorithm for predicting antigenic determinants" (1988) Comput Appl Biosci 4(1):181-186.
Ponomarenko et al., "B-Cell Epitope Prediction," (2009) Structural Bioinformatics, Second Edition 849-879.
Kolaskar et al., "A semi-empirical method for prediction of antigenic determinants on protein antigens," (1990) FEBS Letters, 276(1-2):172-174.
Yao et al., "Conformational B-Cell Epitope Prediction on Antigen Protein Structures: A Review of Current Algorithms and Comparison with Common Binding Site Prediction Methods," (2013) PLOS ONE 8(4):1-4.
Payne, "Progress in immunoconjugate cancer therapeutics," (2003) Cancer Cell 3(3):207-212.
Mandler et al., "Immunoconjugates of Geldanamycin and Anti-HER2 Monoclonal Antibodies: Antiproliferative Activity on Human Breast Carcinoma Cell Lines," (2000) J of the Nat Cancer Inst 92(19):1573-1581.
Liu et al., "Eradication of large colon tumor xenografts by targeted delivery of maytansinoids," (1996) Proc Natl Acad Sci USA 93(16):8618-8623.
Hinman et al., "Preparation and Characterization of Monoclonal Antibody Conjugate of the Calicheamicins: A Novel and Potent Family of Antitumor Antibiotics," (1993) Cancer Res 53:3336-3342.
Doronina et al., "Development of potent monoclonal antibody auristatin conjugates for cancer therapy," (2003) Nature Biotechnology 21(7):778-784.
Francisco et al., "cAC10-vcMMAE, an anti-CD30-monomethyl auristatin E conjugate with potent and selective antitumor activity," (2003) Blood 102(4):1458-1465.
Mao et al., "EphB2 as a Therapeutic Antibody Drug Target for the Treatment of Colorectal Cancer," (2004) Cancer Research 64(3):781-788.
Bhaskar et al., "E-Selectin Up-Regulation Allows for Targeted Drug Delivery in Prostate Cancer," (2003) Cancer Res 63(9):6387-6394.
Better et al., "Gelonin analogs with engineered cysteine residues form antibody immunoconjugates with unique properties," (1994) J Biol Chem 269(13):9644-9650.
Tu et al., "Protein footprinting at cysteines: Probing ATP-modulated contacts in cysteine-substitution mutants of yeast DNA topoisomerase II," (1999) Proc Natl Acad Sci USA 96(9):4862-4867.
Krogh et al., "Predicting Transmembrane Protein Topology with a Hiddne Markov Model: Application to Complete Genomes," (2001) J Mol Biol 305:567-580.
Chmura et al., "Antibodies with infinite affinity," (2001) Proc Nat Acad Sci USA 98(15):8480-8484.
Pons et al., "Staging systems in hepatocellular carcinoma," (2005) HPB 7(1):35-41.
Farges et al., "AJCC 7th edition of TNM staging accurately discriminates outcomes of patients with resectable intrahepatic cholangiocarcinoma," (2011) Cancer 117(10):2170-2177.

(56) References Cited

OTHER PUBLICATIONS

Lu et al., "Tumor-associated protein SPIK/TATI suppresses serine protease dependent cell Apoptosis," (2008) Apoptosis 13(4):483-494.

* cited by examiner

FIG. 1. The Antibodies Bind AS-SPIK but not NS-SPIK

FIG. 2: Detection of Antibody-Antigen Complex in Samples with IM-E2
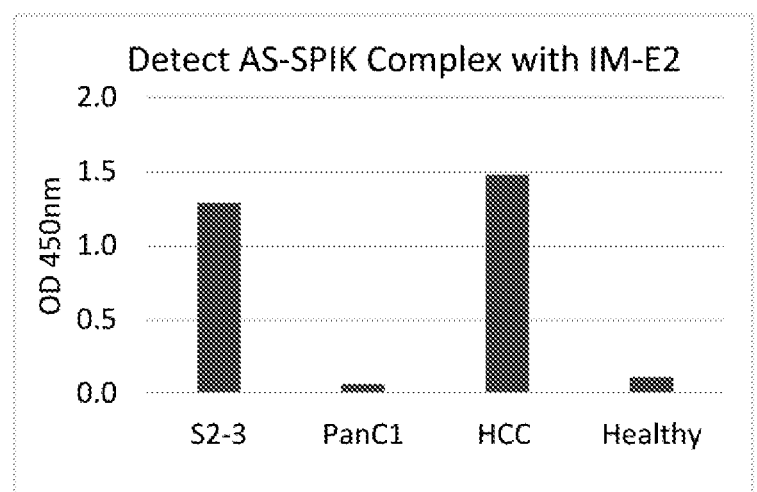

FIG. 3: Alignment: VH of A1, A6, B10, C6, D3, D5, E2, F5, G6, G7

CDRs are underlined. First region is CDR1, Second is CDR2 and third is CDR3

```
                                10         20         30         40         50         60
                         ....|....| ....|....| ....|....| ....|....| ....|....| ....|....|
SEQ ID NO  1: A1  VH     LVAVLKGVQC QSVKESEGGL FKPTDTLTLT CTVSGFSLSS NAISWVRQAP GNGLEWIGAI
SEQ ID NO  2: A6  VH     -VAVLKGVQC QSVKESEGGL FKPTDTLTLT CTVSGFSLSS YAISWVRQAP GNGLEWIGRI
SEQ ID NO  3: B10 VH     LVAVLKGVQC QSVKESEGGL FKPTDTLTLT CTVSGFSLSS YGVSWVRQAP GKGLEWIGSI
SEQ ID NO  4: C6  VH     LVAVLKGVQC QSVKESEGGL FKPTDALTLT CTVSGFSLSS YAISWVRQAP GSGLEWIGAI
SEQ ID NO  5: D3  VH     -VAVLKGVQC QSVKESEGGL FKPTDTLTLT CTVSGFSLSS YAIGWVRQAP GNGLEWIGTI
SEQ ID NO  6: D5  VH     -VAVLKGVQC QSVKESEGGL FKPTDTLTLT CTVSGFSLSS YAISWVRQAP GNGLEWIGAI
SEQ ID NO  7: E2  VH     LVAVLKGVQC QSVKESEGGL FKPTDTLTLT CTVSGFSLSA YAISWVRQAP GNGLEWIGAI
SEQ ID NO  8: F5  VH     -VAVLKGVQC QSVKESEGGL FKPTDTLTLT CTVSGFSLSI YGVSWVRQAP GNGLEWIGII
SEQ ID NO  9: G6  VH     LVAVLKGVQC QSVKESEGGL FKPTDTLTLT CTVSGFSLSS YPISWVRQAP GNGLEWIGDI
SEQ ID NO 10: G7  VH     LVAVLKGVQC QSVKESEGGL FKPTDTLTLT CTVSGFSLSS NVISWVRQAP GKGLEWIGDI
Consensus                LVAVLKGVQC QSVKESEGGL FKPTDTLTLT CTVSGFSLSS YAISWVRQAP GNGLEWIG I 70         80         90        100        110        120
                         ....|....| ....|....| ....|....| ....|....| ....|....| ....|....|
SEQ ID NO  1: A1  VH     GSSGSTYYAS WAKSRSTVTR NTNLNTVTLK MTSLTAADTA TYFCARWENI GYTNVRLDL-
SEQ ID NO  2: A6  VH     NSGGATDYAS WARSRSTITR DTNLNTVTLQ MTSLTAADTA TYFCAKEEYS YGGAYGM---
SEQ ID NO  3: B10 VH     WSGGTTDYAS WAKSRSTITR NTNENTVTLK VTSLTAADTA TYFCARGGYD YGYASNI---
SEQ ID NO  4: C6  VH     NTYGGTYYAS WAKSRSTITR NTNENTVTLK MTSLTAADTA TYFCARDFDS DAYTSASGGM
SEQ ID NO  5: D3  VH     VTSGIPYYAN WAKSRSTITR NTNLNTVTLK MTSLTAADTA TYFCARNLDP AYSTTRLDL-
SEQ ID NO  6: D5  VH     GKSGSAYYAS WAKSRSTITR NTNLNTVSLK MTSLTAADTA TYFCARWDSV GWTDARLDL-
SEQ ID NO  7: E2  VH     NSGGSAYYAN WAKSRSTITR NTNLNTVTLK MTSLTAADTA TYFCAREDIY DYGGAFDP--
SEQ ID NO  8: F5  VH     YASGSADYAS WAKSRSTITR NTNLNTVTLK MTSLTAADTA TYFCAREDDT YGYTSSI---
SEQ ID NO  9: G6  VH     YASGSILYAS WATGRSTITR NTNLNTVTLK MTSLTAADTA TYFCARVSYS GGIDI-----
SEQ ID NO 10: G7  VH     YVSGNTDYAS WAKSRSTITR NANLNTVTLK MTSLTAADTA TYFCARYDMS SDAFDP----
Consensus                     SG   YAS WAKSRSTITR NTNLNTVTLK MTSLTAADTA TYFCAR 130        140        150
                         ....|....| ....|....| ....|....|
SEQ ID NO  1: A1  VH     --WGQGTLVT VSSGQPKAPS VFPLAPCCGD TPSS
SEQ ID NO  2: A6  VH     --WGPGTLVT VSSGQPKAPS VFPLAPCCGD TPSS
SEQ ID NO  3: B10 VH     --WGPGTLVT VSSGQPKAPS
SEQ ID NO  4: C6  VH     DPWGPGTLVT VSSGQPKAPS FFPLAPCCGD TPR
SEQ ID NO  5: D3  VH     --WGQGTLVT VSSGQPKAPS VFPLAPCCGD TPS
SEQ ID NO  6: D5  VH     --WGQGTLVT VSSGQPKAPS VFPLAPCCGD TPS
SEQ ID NO  7: E2  VH     --WGPGTLVT VSTGQPKLHH
SEQ ID NO  8: F5  VH     --WGPGTLVT VSSGQPKAPS VFPLAPCCGD TPS
SEQ ID NO  9: G6  VH     --WGPGTLVT VSSGQPKAPS VFPLAPCCGD TPS
SEQ ID NO 10: G7  VH     --WGPGTLVT VSSGQPKAPS VFPLAPCCGD TPSS
Consensus                  --WG-GTLVT VSSGQPK
```

FIG. 4: Alignment: VL of A1, A6, B10, C6, D3, D5, E2, F5, G6, G7

CDRs are underlined. First region is CDR1, Second is CDR2 and third is CDR3

```
                              10         20         30         40         50         60
                        ....|....| ....|....| ....|....| ....|....| ....|....| ....|....|
SEQ ID NO 11: A1  VL    -WLPGARCAY DMTQTPASVE VAVGGTVTIK CQASQSISTA LAWYQQKPGQ PPKLLIYGAS
SEQ ID NO 12: A6  VL    LWLPGARCAY DMTQTPASVS AAVGGTVTIK CQASESISTY LSWLQQKPGQ PPKLLIYKAS
SEQ ID NO 13: B10 VL    LWLPGARCAY DMTQTPASVE VAVGGTVTIK CQASESISSY LSWYQQKPGQ PPKLLIYRAS
SEQ ID NO 14: C6  VL    -WLPGARCAY DMTQTPASVE VAVGGTVTIK CQASQSINNY LSWYQQIPGQ PPKLLIYRAS
SEQ ID NO 15: D3  VL    -WLPGARCAY DMTQTPASVS EPVRGTVTIK CQASQSISTA LAWYQQKPGQ PPKLLIYAAS
SEQ ID NO 16: D5  VL    -WLPGARCAY DMTQTPASVE VAVGGTVTIK CQASQSISTA LAWYQQKPGQ RPKLLIYGAS
SEQ ID NO 17: E2  VL    -WLPGARCAY DMTQTPASVE VTVGGTVTIK CQASQGISSY LSWYQQKPGQ PPKLLIYAAT
SEQ ID NO 18: F5  VL    -WLPGARCAY DMTQTPASVS AAVGGTVTIK CQASQSISSY LNWYQQKPGQ PPKRLIYRAS
SEQ ID NO 19: G6  VL    -WLPGARCAY DMTQTPASVE VAVGGTVTIK CQASEDIESY LAWYQQKPGQ PPKLLIYRAS
SEQ ID NO 20: G7  VL    LWLPGARCAY DMTQTPASVE VAVGGTVTIK CQASQNIGSY LSWYQHKPGQ RPRLLMYRAS
Consensus               -WLPGARCAY DMTQTPASVE VAVGGTVTIK CQASQSIS Y L WYQQKPGQ PPKLLIY AS 70         80         90        100        110        120
                        ....|....| ....|....| ....|....| ....|....| ....|....| ....|....|
SEQ ID NO 11: A1  VL    TLASGVSSRF KGSGSGTQFT LTISGVECAD AATYYCQQGY STSDVDNAFG GGTEG-----
SEQ ID NO 12: A6  VL    TLASGVPSRF KGSGSGTEFT LTISGVQCDD AATYYCQQDY TISNVGNVFG GGTEVVVKGD
SEQ ID NO 13: B10 VL    TLASGVSSRF SGSGSGTEFT LTISGVQCDD AATYYCQQGY SVSNVDNIFG GGTEVVVKGD
SEQ ID NO 14: C6  VL    TLASGVSSRF KGSGSGTQFT LTISGVQCAD AATYYCQQGY TSNVDNVFGG GTEVVVKGDP
SEQ ID NO 15: D3  VL    YLASGVPSRF SGSGSGTEFT LTISDLECAD AATYYCHQGY SASNVDNTFG GGTEGGVKGD
SEQ ID NO 16: D5  VL    KLASGVSSRF SGSGSGTEFT LTISGVECAD AATYYCQQGY ETSNVDNAFG GGTEVVVKGD
SEQ ID NO 17: E2  VL    TVLSGVSSRF KGSGSGTQFT LTISGVECAD AATYYCQQDY TTSNVDNTFG GGTEVVVKGD
SEQ ID NO 18: F5  VL    TLASGVSSRF KGSGSGTQFT LTISGVECAD AATYYCQQDY SSNNIDNTFG GGTEVVVKGD
SEQ ID NO 19: G6  VL    TLPSGVPSRF KGSGSGTEFT LTISDLECAD AATYYCQQDY SSSNVDNTFG GGTEVVVKGD
SEQ ID NO 20: G7  VL    TLASGVSSRF KGSGSGTEFT LTISGVQCDN AATYYCQQGY TNSGVDNTFG GGTEVVVKGD
Consensus               TLASGVSSRF KGSGSGTEFT LTISGVECAD AATYYCQQGY  SNVDN FG GGTEVVVKGD 130
                        ....|....| ....
SEQ ID NO 11: A1  VL    ---------- ----
SEQ ID NO 12: A6  VL    PVAPTVLIFP PSAD
SEQ ID NO 13: B10 VL    PVAPTVLIFP PSAD
SEQ ID NO 14: C6  VL    VAPTVLIFPP SAD
SEQ ID NO 15: D3  VL    PVAPTVLIFP P
SEQ ID NO 16: D5  VL    PVAPTVLIFP PSAD
SEQ ID NO 17: E2  VL    PVAPTVLIFP PSAD
SEQ ID NO 18: F5  VL    PVAPTVLIFP P
SEQ ID NO 19: G6  VL    PVAPTVLIFP P
SEQ ID NO 20: G7  VL    PVAPTVLIFP PSA
Consensus               PVAPTVLIFP P
```

FIG. 5: Alignment: VH CDR of A1, A6, B10, C6, D3, D5, E2, F5, G6, G7

```
                                          10
CDR1                              ....|....|
SEQ ID NO 21: A1  VH     SSNAIS
SEQ ID NO 22: A6  VH     SSYAIS
SEQ ID NO 23: B10 VH     SSYGVS
SEQ ID NO 24: C6  VH     SSYAIS
SEQ ID NO 25: D3  VH     SSYAIG
SEQ ID NO 26: D5  VH     SSYAIS
SEQ ID NO 27: E2  VH     SAYAIS
SEQ ID NO 28: F5  VH     SIYGVS
SEQ ID NO 29: G6  VH     SSYPIS
SEQ ID NO 30: G7  VH     SSNVIS
Consensus                SSYAIS 10
CDR2                              ....|....| ......
SEQ ID NO 31: A1  VH     AIGSSGSTYY ASWAKS
SEQ ID NO 32: A6  VH     RINSGGATDY ASWARS
SEQ ID NO 33: B10 VH     SIWSGGTTDY ASWAKS
SEQ ID NO 34: C6  VH     AINTYGGTYY ASWAKS
SEQ ID NO 35: D3  VH     TIVTSGIPYY ANWAKS
SEQ ID NO 36: D5  VH     AIGKSGSAYY ASWAKS
SEQ ID NO 37: E2  VH     AINSGGSAYY ANWAKS
SEQ ID NO 38: F5  VH     IIYASGSADY ASWAKS
SEQ ID NO 39: G6  VH     DIYASGSILY ASWATG
SEQ ID NO 40: G7  VH     DIYVSGNTDY ASWAKS
Consensus                -I  SG   Y ASWAKS 10
CDR3                              ....|....| ....
SEQ ID NO 41: A1  VH     RWENIGYTNV RLDL
SEQ ID NO 42: A6  VH     KEEYSYGGAY GM
SEQ ID NO 43: B10 VH     RGGYDYGYAS NI
SEQ ID NO 44: C6  VH     RDFDSDAYTS ASGGMDP
SEQ ID NO 45: D3  VH     RNLDPAYSTT RLDL
SEQ ID NO 46: D5  VH     RWDSVGWTDA RLDL
SEQ ID NO 47: E2  VH     REDIYDYGGA FDP
SEQ ID NO 48: F5  VH     REDDTYGYTS SI
SEQ ID NO 49: G6  VH     RVSYSGGTDI --
SEQ ID NO 50: G7  VH     RYDMSSDAFD P-
Consensus                R
```

FIG. 6: Alignment: VL CDR of A1, A6, B10, C6, D3, D5, E2, F5, G6, G7

```
                                         10
CDR1                         ....|....|...
SEQ ID NO 51: A1 VL          QASQSISTA LA
SEQ ID NO 52: A6 VL          QASESISTY LS
SEQ ID NO 53: B10VL          QASESISSY LS
SEQ ID NO 54: C6 VL          QASQSINNY LS
SEQ ID NO 55: D3 VL          QASQSISTA LA
SEQ ID NO 56: D5 VL          QASQSISTA LA
SEQ ID NO 57: E2 VL          QASQGISSY LS
SEQ ID NO 58: F5 VL          QASQSISSY LN
SEQ ID NO 59: G6 VL          QASEDIESY LA
SEQ ID NO 60: G7 VL          QASQNIGSY LS
Consensus                    QASQSIS-Y L 10
CDR2                         ....|....|
SEQ ID NO 61: A1 VL          GASTLAS
SEQ ID NO 62: A6 VL          KASTLAS
SEQ ID NO 63: B10VL          RASTLAS
SEQ ID NO 64: C6 VL          RASTLAS
SEQ ID NO 65: D3 VL          AASYLAS
SEQ ID NO 66: D5 VL          GASKLAS
SEQ ID NO 67: E2 VL          AATTVLS
SEQ ID NO 68: F5 VL          RASTLAS
SEQ ID NO 69: G6 VL          RASTLPS
SEQ ID NO 70: G7 VL          RASTLAS
Consensus                    ASTLAS 10
CDR3                         ....|....| ....
SEQ ID NO 71: A1 VL          QQGYSTSDVD NA
SEQ ID NO 72: A6 VL          QQDYTISNVG NV
SEQ ID NO 73: B10VL          QQGYSVSNVD NI
SEQ ID NO 74: C6 VL          QQGYTSNVDN VF
SEQ ID NO 75: D3 VL          HQGYSASNVD NT
SEQ ID NO 76: D5 VL          QQGYETSNVD NA
SEQ ID NO 77: E2 VL          QQDYTTSNVD NT
SEQ ID NO 78: F5 VL          QQDYSSNNID NT
SEQ ID NO 79: G6 VL          QQDYSSSNVD NT
SEQ ID NO 80: G7 VL          QQGYTNSGVD NT
Consensus                    QQGY--SNVD N
```

FIG. 7: Sequence Information

SEQ ID NO: 1     A1 variable region heavy chain

LVAVLKGVQCQSVKESEGGLFKPTDTLTLTCTVSGFSLSSNAISWVRQAPGNGLEWIGAI
GSSGSTYYASWAKSRSTVTRNTNLNTVTLKMTSLTAADTATYFCARWENIGYTNVRLD
LWGQGTLVTVSSGQPKAPSVFPLAPCCGDTPSS

SEQ ID NO: 2     A6 variable region heavy chain

VAVLKGVQCQSVKESEGGLFKPTDTLTLTCTVSGFSLSSYAISWVRQAPGNGLEWIGRI
NSGGATDYASWARSRSTITRDTNLNTVTLQMTSLTAADTATYFCAKEEYSYGGAYGM
WGPGTLVTVSSGQPKAPSVFPLAPCCGDTPSS

SEQ ID NO: 3     B10 variable region heavy chain

LVAVLKGVQCQSVKESEGGLFKPTDTLTLTCTVSGFSLSSYGVSWVRQAPGKGLEWIGS
IWSGGTTDYASWAKSRSTITRNTNENTVTLKVTSLTAADTATYFCARGGYDYGYASNI
WGPGTLVTVSSGQPKAPS

SEQ ID NO: 4     C6 variable region heavy chain

LVAVLKGVQCQSVKESEGGLFKPTDALTLTCTVSGFSLSSYAISWVRQAPGSGLEWIGAI
NTYGGTYYASWAKSRSTITRNTNENTVTLKMTSLTAADTATYFCARDFDSDAYTSASG
GMD WGPGTLVTVSSGQPKAPSFFPLAPCCGDTPR

SEQ ID NO: 5     D3 variable region heavy chain

VAVLKGVQCQSVKESEGGLFKPTDTLTLTCTVSGFSLSSYAIGWVRQAPGNGLEWIGTI
VTSGIPYYANWAKSRSTITRNTNLNTVTLKMTSLTAADTATYFCARNLDPAYSTTRLDL
WGQGTLVTVSSGQPKAPSVFPLAPCCGDTPS

FIG. 7 (Cont.)

SEQ ID NO: 6    D5 variable region heavy chain

VAVLKGVQCQSVKESEGGLFKPTDTLTLTCTVSGFSLSSYAISWVRQAPGNGLEWIGAI
GKSGSAYYASWAKSRSTITRNTNLNTVSLKMTSLTAADTATYFCARWDSVGWTDARL
DLWGQGTLVTVSSGQPKAPSVFPLAPCCGDTPS

SEQ ID NO: 7    E2 variable region heavy chain

LVAVLKGVQCQSVKESEGGLFKPTDTLTLTCTVSGFSLSAYAISWVRQAPGNGLEWIGA
INSGGSAYYANWAKSRSTITRNTNLNTVTLKMTSLTAADTATYFCAREDIYDYGGAFDP
WGPGTLVTVSTGQPKLHH

SEQ ID NO: 8    F5 variable region heavy chain

VAVLKGVQCQSVKESEGGLFKPTDTLTLTCTVSGFSLSIYGVSWVRQAPGNGLEWIGIIY
ASGSADYASWAKSRSTITRNTNLNTVTLKMTSLTAADTATYFCAREDDTYGYTSSIWGP
GTLVTVSSGQPKAPSVFPLAPCCGDTPS

SEQ ID NO: 9    G6 variable region heavy chain

LVAVLKGVQCQSVKESEGGLFKPTDTLTLTCTVSGFSLSSYPISWVRQAPGNGLEWIGDI
YASGSILYASWATGRSTITRNTNLNTVTLKMTSLTAADTATYFCARVSYSGGTDIWGPG
TLVTVSSGQPKAPSVFPLAPCCGDTPS

SEQ ID NO: 10    G7 variable region heavy chain

LVAVLKGVQCQSVKESEGGLFKPTDTLTLTCTVSGFSLSSNVISWVRQAPGKGLEWIGDI
YVSGNTDYASWAKSRSTITRNANLNTVTLKMTSLTAADTATYFCARYDMSSDAFDPW
GPGTLVTVSSGQPKAPSVFPLAPCCGDTPSS

FIG. 7 (Cont.)

Light chain variable region sequences:

SEQ ID NO: 11    A1 variable region light chain

WLPGARCAYDMTQTPASVEVAVGGTVTIKCQASQSISTALAWYQQKPGQPPKLLIYGA
STLASGVSSRFKGSGSGTQFTLTISGVECADAATYYCQQGYSTSDVDNAFGGGTEG

SEQ ID NO: 12    A6 variable region light chain

LWLPGARCAYDMTQTPASVSAAVGGTVTIKCQASESISTYLSWLQQKPGQPPKLLIYKA
STLASGVPSRFKGSGSGTEFTLTISGVQCDDAATYYCQQDYTISNVGNVFGGGTEVVVK
GDPVAPTVLIFPPSAD

SEQ ID NO: 13    B10 variable region light chain

LWLPGARCAYDMTQTPASVEVAVGGTVTIKCQASESISSYLSWYQQKPGQPPKLLIYRA
STLASGVPSRFSGSGSGTEFTLTISDGQCDDAATYYCQQGYSVSNVDNIFGGGTEVVVK
GDPVAPTVLIFPPSAD

SEQ ID NO: 14    C6 variable region light chain

WLPGARCAYDMTQTPASVEVAVGGTVTIKCQASQSINNYLSWYQQIPGQPPKLLIYRAS
TLASGVSSRFKGSGSGTQFTLTISGVQCADAATYYCQQGYTSNVDNVFGGGTEVVVKG
DPVAPTVLIFPPSAD

SEQ ID NO: 15    D3 variable region light chain

WLPGARCAYDMTQTPASVSEPVRGTVTIKCQASQSISTALAWYQQKPGQPPKLLIYAAS
YLASGVPSRFSGSGSGTEFTLTISDLECADAATYYCHQGYSASNVDNTFGGGTEGGVKG
DPVAPTVLIFPP

FIG. 7 (Cont.)

SEQ ID NO: 16    D5 variable region light chain
WLPGARCAYDMTQTPASVEVAVGGTVTIKCQASQSISTALAWYQQKPGQRPKLLIYGA
SKLASGVSSRFSGSGSGTEFTLTISGVECADAATYYCQQGYETSNVDNAFGGGTEVVVK
GDPVAPTVLIFPPSAD SEQ ID NO: 17    E2 variable region light chain
WLPGARCAYDMTQTPASVEVTVGGTVTIKCQASQGISSYLSWYQQKPGQPPKLLIYAA
TTLVSGVSSRFKGSGSGTQFTLTISGVECADAATYYCQQDYTTSNVDNTFGGGTEVVVK
GDPVAPTVLIFPPSAD SEQ ID NO: 18    F5 variable region light chain
WLPGARCAYDMTQTPASVSAAVGGTVTIKCQASQSISSYLNWYQQKPGQPPKRLIYRA
STLASGVSSRFKGSGSGTQFTLTISGVECADAATYYCQQDYSSNNIDNTFGGGTEVVVK
GDPVAPTVLIFPP SEQ ID NO: 19    G6 variable region light chain
WLPGARCAYDMTQTPASVEVAVGGTVTIKCQASEDIESYLAWYQQKPGQPPKLLIYRA
STLPSGVPSRFKGSGSGTEFTLTISDLECADAATYYCQQDYSSSNVDNTFGGGTEVVVK
GDPVAPTVLIFPP SEQ ID NO: 20    G7 variable region light chain
LWLPGARCAYDMTQTPASVEVAVGGTVTIKCQASQNIGSYLSWYQHKPGQRPRLLMY
RASTLASGVSSRFKGSGSGTEFTLTISGVQCDNAATYYCQQGYTNSGVDNTFGGGTEVV
VKGDPVAPTVLIFPPSA

FIG. 7 (Cont.)

CDRH Sequences:

| Antibody Name | CDRH1 | CDRH2 | CDRH3 |
|---|---|---|---|
| A1 | SSNAIS (SEQ ID NO: 21) | AIGSSGSTYYASWAKS (SEQ ID NO: 31) | RWENIGYTNVRLDL (SEQ ID NO: 41) |
| A6 | SAYAISW (SEQ ID NO: 22) | RINSGGATDYASWARS( SEQ ID NO: 32) | KEEYSYGGAYGM (SEQ ID NO: 42) |
| B10 | SSYGVS (SEQ ID NO: 23) | SIWSGGTTDYASWAKS (SEQ ID NO: 33) | RGGYDYGYASNI (SEQ ID NO: 43) |
| C6 | SYAISW (SEQ ID NO: 24) | AINTYGGTYYASWAKS (SEQ ID NO: 34) | RDFDSDAYTSASGGMDP (SEQ ID NO: 44) |
| D3 | SSYAIG (SEQ ID NO: 25) | TIVTSGIPYYANWAKS (SEQ ID NO: 35) | RNLDPAYSTTRLDL (SEQ ID NO: 45) |
| D5 | SSYAIS (SEQ ID NO: 26) | AIGKSGSAYYASWAKS (SEQ ID NO: 36) | RWDSVGWTDARLDL (SEQ ID NO: 46) |
| E2 | SAYAISW (SEQ ID NO: 27) | AINSGGSAYYANWAKS (SEQ ID NO: 37) | REDIYDYGGAFDP (SEQ ID NO: 47) |
| F5 | IYGVSW (SEQ ID NO: 28) | IIYASGSADYASWAKS (SEQ ID NO: 38) | REDDTYGYTSSI (SEQ ID NO: 48) |
| G6 | SYPISW (SEQ ID NO: 29) | DIYASGSILYASWATG (SEQ ID NO: 39) | RVSYSGGTDI (SEQ ID NO: 49) |
| G7 | SNVISW (SEQ ID NO: 30) | DIYVSGNTDYASWAKS (SEQ ID NO: 40) | RYDMSSDAFDP (SEQ ID NO: 50) |

FIG. 7 (Cont.)

CDRL Sequences:

| Antibody Name | CDRL1 | CDRL2 | CDRL3 |
|---|---|---|---|
| A1 | QASQSISTALA (SEQ ID NO: 51) | GASTLAS (SEQ ID NO: 61) | QQGYSTSDVDNA (SEQ ID NO: 71) |
| A6 | QASESISTYLS (SEQ ID NO: 52) | KASTLAS (SEQ ID NO: 62) | QQDYTISNVGNV (SEQ ID NO: 72) |
| B10 | QASESISSYLS (SEQ ID NO: 53) | RASTLAS (SEQ ID NO: 63) | QQGYSVSNVDNI (SEQ ID NO: 73) |
| C6 | QASQSINNYLS (SEQ ID NO: 54) | RASTLAS (SEQ ID NO: 64) | QQGYTSNVDNVF (SEQ ID NO: 74) |
| D3 | QASQSISTALA (SEQ ID NO: 55) | AASYLAS (SEQ ID NO: 65) | HQGYSASNVDNT (SEQ ID NO: 75) |
| D5 | QASQSISTALA (SEQ ID NO: 56) | GASKLAS (SEQ ID NO: 66) | QQGYETSNVDNA (SEQ ID NO: 76) |
| E2 | QASQGISSYLS (SEQ ID NO: 57) | AATTLVS (SEQ ID NO: 67) | QQDYTTSNVDNT (SEQ ID NO: 77) |
| F5 | QASQSISSYLN (SEQ ID NO: 58) | RASTLAS (SEQ ID NO: 68) | QQDYSSNNIDNT (SEQ ID NO: 78) |
| G6 | QASEDIESYLA (SEQ ID NO: 59) | RASTLPS (SEQ ID NO: 69) | QQDYSSSNVDNT (SEQ ID NO: 79) |
| G7 | QASQNIGSYLS (SEQ ID NO: 60) | MYRASTLAS (SEQ ID NO: 70) | QQGYTNSGVDNT (SEQ ID NO: 80) |

FIG. 7 (Cont.)

AS-SPIK and NS-SPIK Protein Sequence Data:

SEQ ID NO: 81     (23 amino acid sequence only existing at the N-terminus of AS-SPIK, but not in NS-SPIK)

MKVTGIFLLSALALLSLSGNTGA

SEQ ID NO: 82     (Protein sequence of full-length AS-SPIK)

MKVTGIFLLSALALLSLSGNTGADSLGREAKCYNELNGCTKIYDPVCGTDGNTYPNECV
LCFENRKRQTSILIQKSGPC

SEQ ID NO: 83     (Protein sequence of full-length NS-SPIK)

DSLGREAKCYNELNGCTKIYDPVCGTDGNTYPNECVLCFENRKRQTSILIQKSGPC

FIG. 7 (Cont.)

DNA SEQUENCE DATA

SEQ ID NO: 84    A1 variable region heavy chain

CTGGTCGCTGTGCTCAAAGGTGTCCAGTGTCAGTCGGTGAAGGAGTCCGAGGGAGGTCTCTT
CAAGCCAACGGATACCCTGACACTCACCTGCACAGTCTCTGGATTCTCCCTCAGTAGCAATG
CAATAAGCTGGGTCCGCCAGGCTCCAGGGAACGGGCTGGAATGGATCGGAGCCATTGGTAG
TAGTGGTAGCACATACTACGCGAGCTGGGCGAAAAGCCGATCCACCGTCACCAGAAACACC
AACCTGAACACGGTGACTCTAAAGATGACCAGTCTGACAGCCGCGGACACGGCCACCTATTT
CTGTGCGAGATGGGAGAATATTGGTTATACTAATGTTCGGTTGGATCTCTGGGGCCAGGGCA
CCCTGGTCACCGTCTCCTCAGGGCAACCTAAGGCTCCATCAGTCTTCCCACTGGCCCCCTGCT
GCGGGGACACACCCAGCTCC

SEQ ID NO: 85    A1 variable region light chain

TGGCTCCCAGGTGCCAGATGTGCCTATGATATGACCCAGACTCCAGCCTCTGTGGAGGTAGC
TGTGGGAGGCACAGTCACCATCAAGTGCCAGGCCAGTCAGAGCATTAGCACTGCATTAGCCT
GGTATCAGCAGAAACCAGGGCAGCCTCCCAAGCTCCTGATCTATGGTGCATCCACTCTGGCA
TCTGGGGTCTCATCGCGGTTCAAAGGCAGTGGATCTGGGACACAGTTCACTCTCACCATCAG
CGGCGTGGAGTGTGCCGATGCTGCCACTTACTACTGTCAACAGGGTTATAGTACTAGTGATG
TTGATAATGCTTTCGGCGGAGGGACCGAGGGGG

SEQ ID NO: 86    A6 variable region heavy chain

GGTCGCTGTGCTCAAAGGTGTCCAGTGTCAGTCGGTGAAGGAGTCCGAGGGAGGTCTCTTCA
AGCCAACGGATACCCTGACACTCACCTGCACAGTCTCTGGATTCTCCCTCAGTAGCTATGCA
ATAAGTTGGGTCCGCCAGGCTCCAGGGAACGGGCTGGAATGGATCGGGCGCATTAATAGTG
GTGGTGCCACAGACTACGCGAGCTGGGCGAGAAGCCGATCCACCATCACCAGAGACACCAA
CCTGAACACGGTGACTCTGCAAATGACCAGTCTGACCGCCGCGGACACGGCCACCTATTTCT
GTGCGAAAGAAGAGTATAGTTATGGTGGTGCTTATGGTATGTGGGGCCCAGGCACTCTGGTC
ACCGTCTCCTCAGGGCAACCTAAGGCTCCATCAGTCTTCCCACTGGCCCCCTGCTGCGGGGA
CACACCCAGCTCC

FIG. 7 (Cont.)

SEQ ID NO: 87    A6 variable region light chain
CTCTGGCTCCCAGGTGCCAGATGTGCCTATGATATGACCCAGACTCCAGCCTCCGTGTCTGC
AGCTGTGGGAGGCACAGTCACCATCAAGTGCCAGGCCAGTGAGAGCATTAGTACCTACTTAT
CCTGGTTGCAGCAGAAACCAGGGCAGCCTCCCAAGCTCCTGATCTACAAGGCTTCCACTCTG
GCATCTGGGGTCCCATCGCGGTTCAAAGGCAGTGGATCTGGGACAGAGTTCACTCTCACCAT
CAGCGGTGTGCAGTGTGACGATGCTGCCACTTACTACTGTCAACAGGATTATACTATTAGTA
ATGTTGGTAATGTTTTCGGCGGAGGGACCGAGGTGGTGGTCAAAGGTGATCCAGTTGCACCT
ACTGTCCTCATCTTCCCACCATCAGCGGACCA SEQ ID NO: 88    B10 variable region heavy chain
CCTGGTCGCTGTGCTCAAAGGTGTCCAGTGTCAGTCGGTGAAGGAGTCCGAGGGAGGTCTCT
TCAAGCCAACGGATACCCTGACACTCACCTGCACAGTCTCTGGATTCTCCCTCAGTAGTTAT
GGAGTGAGCTGGGTCCGCCAGGCTCCAGGGAAGGGGCTGGAGTGGATCGGGTCCATTTGGA
GTGGTGGTACCACAGACTACGCGAGCTGGGCGAAAAGCCGATCCACCATAACCAGAAACAC
CAACGAGAACACGGTGACTCTGAAAGTGACCAGTCTGACAGCCGCGGACACGGCCACCTAT
TTCTGTGCGAGGGGGGGTTATGATTATGGTTATGCCTCGAACATCTGGGGCCCAGGCACCCT
GGTCACCGTCTCCTCAGGGCAACCTAAGGCTCCATCA SEQ ID NO: 89    B10 variable region light chain
CTCTGGCTCCCAGGTGCCAGATGTGCCTATGATATGACCCAGACTCCAGCCTCTGTGGAGGT
AGCTGTGGGAGGCACAGTCACCATCAAGTGCCAGGCCAGTGAAAGCATTAGCAGCTACTTA
TCCTGGTATCAGCAGAAACCAGGGCAGCCTCCCAAGCTCCTGATCTACAGGGCTTCCACTCT
GGCATCTGGGGTCCCATCGCGGTTCAGTGGCAGTGGATCTGGGACAGAGTTCACTCTCACCA
TCAGCGACGGGCAGTGTGACGATGCTGCCACTTACTACTGTCAACAGGGTTATAGTGTTAGT
AATGTTGATAATATTTTCGGCGGAGGGACCGAGGTGGTGGTCAAAGGTGATCCAGTTGCACC
TACTGTCCTCATCTTCCCACCATCAGCGGACCA

FIG. 7 (Cont.)

SEQ ID NO: 90      C6 variable region heavy chain

CCTGGTCGCTGTGCTCAAAGGTGTCCAGTGTCAGTCGGTGAAGGAGTCCGAGGGAGGTCTCT
TCAAGCCAACGGATGCCCTGACACTCACCTGCACAGTCTCTGGATTCTCCCTCAGTAGCTAT
GCAATAAGCTGGGTCCGCCAGGCTCCAGGGAGCGGGCTGGAATGGATCGGAGCCATTAATA
CTTATGGTGGCACATACTACGCGAGCTGGGCGAAAAGCCGATCCACCATCACCAGAAACAC
CAACGAGAACACGGTGACTCTGAAAATGACCAGTCTGACAGCCGCGGACACGGCCACCTAT
TTCTGTGCGAGAGACTTCGATAGTGATGCTTATACTTCTGCTAGTGGGGGCATGGACCCCTG
GGGCCCAGGGACCCTCGTCACCGTCTCTTCAGGGCAACCTAAGGCTCCATCATTCTTCCCAC
TGGCCCCCTGCTGCGGGGACACACCCAG

SEQ ID NO: 91      C6 variable region light chain

TCTGGCTCCCAGGTGCCAGATGTGCCTATGATATGACCCAGACTCCAGCCTCTGTGGAGGTA
GCTGTGGGAGGCACAGTCACCATCAAGTGCCAGGCCAGTCAGAGCATTAACAACTACTTATC
CTGGTATCAGCAAATACCAGGGCAGCCTCCCAAGCTCCTGATCTACAGGGCATCCACTCTGG
CATCTGGGGTCTCATCGCGGTTCAAAGGCAGTGGATCTGGGACACAGTTCACTCTCACCATC
AGCGGCGTGCAGTGTGCCGATGCTGCCACTTACTACTGTCAACAGGGTTATACTAGTAATGT
TGATAATGTTTTCGGCGGAGGGACCGAGGTGGTGGTCAAAGGTGATCCAGTTGCACCTACTG
TCCTCATCTTCCCACCATCAGCGGACCA

SEQ ID NO: 92      D3 variable region heavy chain

GGTCGCTGTGCTCAAAGGTGTCCAGTGTCAGTCGGTGAAGGAGTCCGAGGGAGGTCTCTTCA
AGCCAACGGATACCCTGACACTCACCTGCACAGTCTCTGGATTCTCCCTCAGTAGCTATGCA
ATAGGCTGGGTCCGCCAGGCTCCAGGGAACGGGCTGGAATGGATCGGAACCATTGTTACTA
GTGGTATCCCATACTACGCGAACTGGGCGAAAAGCCGATCCACCATCACCAGAAACACCAA
CCTGAACACGGTGACTCTGAAAATGACCAGTCTGACAGCCGCGGACACGGCCACCTATTTCT
GTGCGAGAAATTTAGATCCTGCTTATAGTACCACTCGGTTGGATCTCTGGGCCAGGGCACC
CTGGTCACCGTCTCCTCAGGGCAACCTAAGGCTCCATCAGTCTTCCCACTGGCCCCCTGCTGC
GGGGACACACCCAGCTC

FIG. 7 (Cont.)

SEQ ID NO: 93    D3 variable region light chain
TCTGGCTCCCAGGTGCCAGATGTGCCTATGATATGACCCAGACTCCAGCCTCCGTGTCTGAA
CCTGTGAGAGGCACAGTCACCATCAAGTGCCAGGCCAGTCAGAGCATTAGCACTGCATTAG
CCTGGTATCAGCAGAAACCAGGGCAGCCTCCCAAGCTCCTGATCTATGCTGCATCCTATCTG
GCCTCTGGGGTCCCATCGCGGTTCAGCGGCAGTGGATCTGGGACAGAGTTCACTCTCACCAT
CAGCGACCTGGAGTGTGCCGATGCTGCCACTTACTACTGTCATCAGGGTTATAGTGCTAGTA
ATGTTGATAATACTTTCGGCGGAGGGACCGAGGGGGGGGTCAAAGGTGATCCAGTTGCACC
TACTGTCCTCATCTTCCCACCATC

SEQ ID NO: 94    D5 variable region heavy chain
GGTCGCTGTGCTCAAAGGTGTCCAGTGTCAGTCAGTGAAGGAGTCCGAGGGAGGTCTCTTCA
AGCCAACGGATACCCTGACACTCACCTGCACAGTCTCTGGATTCTCCCTCAGTAGCTATGCA
ATAAGTTGGGTCCGCCAGGCTCCAGGGAACGGGCTGGAATGGATCGGAGCCATTGGTAAAA
GTGGTAGCGCATACTACGCGAGCTGGGCGAAAAGCCGATCCACCATCACCAGAAACACCAA
CCTGAACACGGTGTCGCTGAAAATGACCAGTCTGACAGCCGCGGACACGGCCACCTATTTCT
GTGCGAGATGGGATAGTGTTGGTTGGACTGATGCTCGGTTGGATCTCTGGGGCCAGGGCACC
CTGGTCACCGTCTCCTCAGGGCAACCTAAGGCTCCATCAGTCTTCCCACTGGCCCCCTGCTGC
GGGGACACACCCAGCTC

SEQ ID NO: 95    D5 variable region light chain
CTGGCTCCCAGGTGCCAGATGTGCCTATGATATGACCCAGACTCCAGCCTCTGTGGAGGTAG
CTGTGGGAGGCACAGTCACCATCAAGTGCCAGGCCAGTCAGAGCATTAGCACTGCATTAGC
CTGGTATCAGCAGAAACCAGGGCAGCGTCCCAAGCTCCTGATCTATGGTGCATCGAAACTGG
CATCTGGGGTCTCATCGCGGTTCAGTGGCAGTGGATCTGGGACAGAGTTCACTCTCACCATC
AGCGGCGTGGAGTGTGCCGATGCTGCCACTTACTACTGTCAACAGGGTTATGAAACTAGTAA
TGTTGATAATGCTTTCGGCGGAGGGACCGAGGTGGTGGTCAAAGGTGATCCAGTTGCACCTA
CTGTCCTCATCTTCCCACCATCAGCGGACCA

FIG. 7 (Cont.)

SEQ ID NO: 96     E2 variable region heavy chain
CTGGTCGCTGTGCTCAAAGGTGTCCAGTGTCAGTCGGTGAAGGAGTCCGAGGGAGGTCTCTT
CAAGCCAACGGATACCCTGACACTCACCTGCACAGTCTCTGGATTCTCCCTCAGTGCCTATG
CAATAAGCTGGGTCCGCCAGGCTCCAGGGAACGGGCTGGAATGGATCGGAGCCATTAATAG
TGGTGGTAGCGCATACTACGCGAACTGGGCGAAAAGCCGATCCACCATCACCAGAAACACC
AACCTGAACACGGTGACTCTGAAAATGACCAGTCTGACAGCCGCGGACACGGCCACCTATTT
CTGTGCGAGGGAAGATATTTATGATTATGGTGGTGCATTCGATCCCTGGGGCCCAGGCACCC
TGGTCACCGTCTCCACAGGGCAACCTAAGCTCCATCAT

SEQ ID NO: 97     E2 variable region light chain
CTGGCTCCCAGGTGCCAGATGTGCCTATGATATGACCCAGACTCCAGCCTCTGTGGAGGTAA
CTGTGGGAGGCACAGTCACCATCAAGTGCCAGGCCAGTCAAGGCATTAGTAGTTACTTATCC
TGGTATCAGCAGAAACCAGGGCAGCCTCCCAAGCTCCTGATCTATGCTGCGACCACTCTGGT
ATCTGGGGTCTCATCGCGGTTCAAAGGCAGTGGATCTGGGACACAGTTCACTCTCACCATCA
GCGGCGTGGAGTGTGCCGATGCTGCCACTTACTACTGTCAGCAGGATTATACTACTAGTAAT
GTTGATAATACTTTCGGCGGAGGGACCGAGGTGGTGGTCAAAGGTGATCCAGTTGCACCTAC
TGTCCTCATCTTCCCACCATCAGCGGACC

SEQ ID NO: 98     F5 variable region heavy chain
GTCGCTGTGCTCAAAGGTGTCCAGTGTCAGTCGGTGAAGGAGTCCGAGGGAGGTCTCTTCAA
GCCAACGGATACCCTGACACTCACCTGCACAGTCTCTGGATTCTCCCTCAGCATCTATGGAG
TGAGCTGGGTCCGCCAGGCTCCAGGGAACGGGCTGGAATGGATCGGAATCATTTATGCTAGT
GGTAGCGCAGACTACGCGAGCTGGGCGAAAAGCCGATCCACCATCACCAGAAACACCAACC
TGAACACGGTGACTCTGAAGATGACCAGTCTGACAGCCGCGGACACGGCCACCTATTTCTGT
GCGAGAGAGGACGATACTTATGGTTATACTAGTAGTATATGGGGCCCAGGCACCCTGGTCAC
CGTCTCCTCAGGGCAACCTAAGGCTCCATCAGTCTTCCCACTGGCCCCCTGCTGCGGGGACA
CACCCAGCTC

FIG. 7 (Cont.)

SEQ ID NO: 99    F5 variable region light chain
TGGCTCCCAGGTGCCAGATGTGCCTATGATATGACCCAGACTCCAGCCTCCGTGTCTGCAGC
TGTGGGAGGCACAGTCACCATCAAGTGCCAGGCCAGTCAGAGCATTAGTAGCTACTTAAACT
GGTATCAGCAGAAACCAGGGCAGCCTCCCAAGCGCCTGATCTACAGGGCATCCACTCTGGC
ATCTGGGGTCTCATCGCGGTTCAAAGGCAGTGGATCTGGGACACAGTTCACTCTCACCATCA
GCGGCGTGGAGTGTGCCGATGCTGCCACTTACTACTGTCAACAGGATTATAGTAGTAATAAT
ATTGATAATACTTTCGGCGGAGGGACCGAGGTGGTGGTCAAAGGTGATCCAGTTGCACCTAC
TGTCCTCATCTTCCCACCAT

SEQ ID NO: 100    G6 variable region heavy chain
CTGGTCGCTGTGCTCAAAGGTGTCCAGTGTCAGTCGGTGAAGGAGTCCGAGGGAGGTCTCTT
CAAGCCAACGGATACCCTGACACTCACCTGCACAGTCTCTGGATTCTCCCTCAGTAGCTATC
CAATAAGCTGGGTCCGCCAGGCTCCAGGGAACGGGCTGGAATGGATCGGAGACATTTATGC
TAGTGGTAGTATATTGTACGCGAGCTGGGCGACAGGCCGATCTACCATCACCAGAAATACCA
ACCTGAACACGGTGACTCTGAAAATGACCAGTCTGACAGCCGCGGACACGGCCACCTATTTC
TGTGCGAGAGTAAGTTATAGTGGTGGTACCGACATCTGGGGCCCAGGCACCCTGGTCACCGT
CTCCTCAGGGCAACCTAAGGCTCCATCAGTCTTCCCACTGGCCCCCTGCTGCGGGGACACAC
CCAGCTC

SEQ ID NO: 101    G6 variable region light chain
TCTGGCTCCCAGGTGCCAGATGTGCCTATGATATGACCCAGACTCCAGCCTCTGTGGAGGTA
GCTGTGGGAGGCACAGTCACCATCAAGTGCCAGGCCAGTGAGGACATTGAAAGCTATTTAG
CCTGGTATCAGCAGAAACCAGGGCAGCCTCCCAAGCTCCTGATCTACAGGGCATCCACTCTG
CCATCTGGGGTCCCATCGCGGTTCAAAGGCAGTGGATCTGGGACAGAGTTCACTCTCACCAT
CAGCGACCTGGAGTGTGCCGATGCTGCCACTTACTACTGTCAACAGGATTATAGTAGTAGTA
ATGTTGATAATACTTTCGGCGGAGGGACCGAGGTGGTGGTCAAAGGTGATCCAGTTGCACCT
ACTGTCCTCATCTTCCCACCATC

FIG. 7 (Cont.)

SEQ ID NO: 102   G7 variable region heavy chain
CTGGTCGCTGTGCTCAAAGGTGTCCAGTGTCAGTCGGTGAAGGAGTCCGAGGGAGGTCTCTT
CAAGCCAACGGATACCCTGACACTCACCTGCACAGTCTCTGGATTCTCCCTCAGTAGCAATG
TAATAAGCTGGGTCCGCCAGGCTCCAGGGAAGGGGCTGGAGTGGATCGGAGACATTTATGT
TAGTGGTAACACAGACTACGCGAGCTGGGCGAAAAGCCGATCCACCATCACCAGAAACGCC
AACCTGAACACGGTGACTCTGAAAATGACCAGTCTGACAGCCGCGGACACGGCCACCTATTT
CTGTGCGAGATATGATATGAGTAGTGATGCTTTCGATCCCTGGGGCCCAGGCACCCTGGTCA
CCGTCTCCTCAGGGCAACCTAAGGCTCCATCAGTCTTCCCACTGGCCCCCTGCTGCGGGGAC
ACACCCAGCTCC

SEQ ID NO: 103   G7 variable region light chain
TCTCTGGCTCCCAGGTGCCAGATGTGCCTATGATATGACCCAGACTCCAGCCTCTGTGGAGG
TAGCTGTGGGAGGCACAGTCACCATCAAGTGCCAGGCCAGTCAGAACATTGGTAGCTACTTA
TCCTGGTATCAGCACAAACCAGGGCAGCGTCCCAGACTCCTGATGTACAGGGCATCCACTCT
GGCATCTGGGGTCTCATCGCGGTTCAAAGGCAGTGGATCTGGGACAGAGTTCACTCTCACCA
TCAGCGGTGTGCAGTGTGACAATGCTGCCACTTACTACTGTCAACAGGGTTATACTAATAGT
GGTGTTGATAATACTTTCGGCGGAGGGACCGAGGTGGTGGTCAAAGGTGATCCAGTTGCACC
TACTGTCCTCATCTTCCCACCATCAGCGG

SEQ ID NO: 104   DNA sequence only existing in AS-SPIK but not NS-SPIK)
ATGAAGGTAACAGGCATCTTTCTTCTCAGTGCCTTGGCCCTGTTGAGTCTATCTGGTAACACTG
GAGCT

SEQ ID NO: 105   DNA sequence of full-length AS-SPIK
ATGAAGGTAACAGGCATCTTTCTTCTCAGTGCCTTGGCCCTGTTGAGTCTATCTGGTAACACTG
GAGCTGACTCCCTGGGAAGAGAGGCCAAATGTTACAATGAACTTAATGGATGCACCAAGATA
TATGACCCTGTCTGTGGGACTGATGGAAATACTTATCCCAATGAATGCGTGTTATGTTTTGAAA
ATCGGAAACGCCAGACTTCTATCCTCATTCAAAAATCTGGGCCTTGC

FIG. 7 (Cont.)

SEQ ID NO: 106    DNA sequence of full-length NS-SPIK

GACTCCCTGGGAAGAGAGGCCAAATGTTACAATGAACTTAATGGATGCACCAAGATATATGA
CCCTGTCTGTGGGACTGATGGAAATACTTATCCCAATGAATGCGTGTTATGTTTTGAAAATCG
GAAACGCCAGACTTCTATCCTCATTCAAAAATCTGGGCCTTGC

SEQ ID NO: 107 VH CDR1 structural formula

S $X_1$ $X_2$ $X_3$ $X_4$ S, where $X_1$ is S or A; $X_2$ is Y or N; $X_3$ is A, G, P or V; and $X_4$ is I or V.

SEQ ID NO: 108 VH CDR2 structural formula

$X_5$ I $X_6$ $X_7$ $X_8$ G $X_9$ $X_{10}$ $X_{11}$ Y A S W A K S, where $X_8$ is S, G or Y; and $X_5$, $X_6$, $X_7$, $X_9$, $X_{10}$ and $X_{11}$ are any amino acid.

SEQ ID NO: 109 VH CDR3 structural formula

R $X_{12}$ $X_{13}$ $X_{14}$ $X_{15}$ $X_{16}$ $X_{17}$ $X_{18}$ $X_{19}$ $X_{20}$ $X_{21}$, where $X_{12}$, $X_{13}$, $X_{14}$, $X_{15}$, $X_{16}$, $X_{17}$, $X_{18}$, $X_{19}$, $X_{20}$, and $X_{21}$ are any amino acid.

SEQ ID NO: 110 VL CDR1 structural formula

Q A S $X_{22}$ $X_{23}$ I $X_{24}$ $X_{25}$ $X_{26}$ L $X_{27}$, where $X_{22}$ is Q or E; $X_{23}$ is S, G, D or N; $X_{24}$ is S, N, E or G; $X_{25}$ is any amino acid; $X_{26}$ is Y or A; and $X_{27}$ is any amino acid.

SEQ ID NO: 111 VL CDR2 structural formula

$X_{28}$ A $X_{29}$ $X_{30}$ L $X_{31}$ S, where $X_{28}$ is any amino acid; $X_{29}$ is S or T; $X_{30}$ is T, Y or K; and $X_{31}$ is A, P or V.

SEQ ID NO: 112 VL CDR3 structural formula

$X_{32}$ Q $X_{33}$ Y $X_{34}$ $X_{35}$ $X_{36}$ $X_{37}$ $X_{38}$ $X_{39}$ $X_{40}$ $X_{41}$, wherein $X_{32}$ is Q or H; $X_{33}$ is G or D; $X_{34}$ is any amino acid; $X_{35}$ is any amino acid; $X_{36}$ is S or N; $X_{37}$ is N, D, V or G; $X_{38}$ is V, D or I; $X_{39}$ is D, G or N; $X_{40}$ is N or V; and $X_{41}$ is any amino acid.

SEQUENCE LISTING

```
<160> NUMBER OF SEQ ID NOS: 113

<210> SEQ ID NO 1
<211> LENGTH: 151
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 1

Leu Val Ala Val Leu Lys Gly Val Gln Cys Gln Ser Val Lys Glu Ser
1               5                   10                  15

Glu Gly Gly Leu Phe Lys Pro Thr Asp Thr Leu Thr Leu Thr Cys Thr
                20                  25                  30

Val Ser Gly Phe Ser Leu Ser Ser Asn Ala Ile Ser Trp Val Arg Gln
            35                  40                  45

Ala Pro Gly Asn Gly Leu Glu Trp Ile Gly Ala Ile Gly Ser Ser Gly
        50                  55                  60

Ser Thr Tyr Tyr Ala Ser Trp Ala Lys Ser Arg Ser Thr Val Thr Arg
65                  70                  75                  80

Asn Thr Asn Leu Asn Thr Val Thr Leu Lys Met Thr Ser Leu Thr Ala
```

```
                85                  90                  95
Ala Asp Thr Ala Thr Tyr Phe Cys Ala Arg Trp Glu Asn Ile Gly Tyr
            100                 105                 110

Thr Asn Val Arg Leu Asp Leu Trp Gly Gln Gly Thr Leu Val Thr Val
        115                 120                 125

Ser Ser Gly Gln Pro Lys Ala Pro Ser Val Phe Pro Leu Ala Pro Cys
    130                 135                 140

Cys Gly Asp Thr Pro Ser Ser
145                 150

<210> SEQ ID NO 2
<211> LENGTH: 148
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

Val Ala Val Leu Lys Gly Val Gln Cys Gln Ser Val Lys Glu Ser Glu
1               5                   10                  15

Gly Gly Leu Phe Lys Pro Thr Asp Thr Leu Thr Leu Thr Cys Thr Val
            20                  25                  30

Ser Gly Phe Ser Leu Ser Ser Tyr Ala Ile Ser Trp Val Arg Gln Ala
        35                  40                  45

Pro Gly Asn Gly Leu Glu Trp Ile Gly Arg Ile Asn Ser Gly Gly Ala
    50                  55                  60

Thr Asp Tyr Ala Ser Trp Ala Arg Ser Arg Ser Thr Ile Thr Arg Asp
65                  70                  75                  80

Thr Asn Leu Asn Thr Val Thr Leu Gln Met Thr Ser Leu Thr Ala Ala
                85                  90                  95

Asp Thr Ala Thr Tyr Phe Cys Ala Lys Glu Glu Tyr Ser Tyr Gly Gly
            100                 105                 110

Ala Tyr Gly Met Trp Gly Pro Gly Thr Leu Val Thr Val Ser Ser Gly
        115                 120                 125

Gln Pro Lys Ala Pro Ser Val Phe Pro Leu Ala Pro Cys Cys Gly Asp
    130                 135                 140

Thr Pro Ser Ser
145

<210> SEQ ID NO 3
<211> LENGTH: 135
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 3

Leu Val Ala Val Leu Lys Gly Val Gln Cys Gln Ser Val Lys Glu Ser
1               5                   10                  15

Glu Gly Gly Leu Phe Lys Pro Thr Asp Thr Leu Thr Leu Thr Cys Thr
            20                  25                  30

Val Ser Gly Phe Ser Leu Ser Ser Tyr Gly Val Ser Trp Val Arg Gln
        35                  40                  45

Ala Pro Gly Lys Gly Leu Glu Trp Ile Gly Ser Ile Trp Ser Gly Gly
    50                  55                  60
```

```
Thr Thr Asp Tyr Ala Ser Trp Ala Lys Ser Arg Ser Thr Ile Thr Arg
65                  70                  75                  80

Asn Thr Asn Glu Asn Thr Val Thr Leu Lys Val Thr Ser Leu Thr Ala
                85                  90                  95

Ala Asp Thr Ala Thr Tyr Phe Cys Ala Arg Gly Gly Tyr Asp Tyr Gly
            100                 105                 110

Tyr Ala Ser Asn Ile Trp Gly Pro Gly Thr Leu Val Thr Val Ser Ser
        115                 120                 125

Gly Gln Pro Lys Ala Pro Ser
    130                 135
```

<210> SEQ ID NO 4
<211> LENGTH: 153
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 4

```
Leu Val Ala Val Leu Lys Gly Val Gln Cys Gln Ser Val Lys Glu Ser
1               5                   10                  15

Glu Gly Gly Leu Phe Lys Pro Thr Asp Ala Leu Thr Leu Thr Cys Thr
            20                  25                  30

Val Ser Gly Phe Ser Leu Ser Ser Tyr Ala Ile Ser Trp Val Arg Gln
        35                  40                  45

Ala Pro Gly Ser Gly Leu Glu Trp Ile Gly Ala Ile Asn Thr Tyr Gly
    50                  55                  60

Gly Thr Tyr Tyr Ala Ser Trp Ala Lys Ser Arg Ser Thr Ile Thr Arg
65                  70                  75                  80

Asn Thr Asn Glu Asn Thr Val Thr Leu Lys Met Thr Ser Leu Thr Ala
                85                  90                  95

Ala Asp Thr Ala Thr Tyr Phe Cys Ala Arg Asp Phe Asp Ser Asp Ala
            100                 105                 110

Tyr Thr Ser Ala Ser Gly Gly Met Asp Pro Trp Gly Pro Gly Thr Leu
        115                 120                 125

Val Thr Val Ser Ser Gly Gln Pro Lys Ala Pro Ser Phe Phe Pro Leu
    130                 135                 140

Ala Pro Cys Cys Gly Asp Thr Pro Arg
145                 150
```

<210> SEQ ID NO 5
<211> LENGTH: 149
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 5

```
Val Ala Val Leu Lys Gly Val Gln Cys Gln Ser Val Lys Glu Ser Glu
1               5                   10                  15

Gly Gly Leu Phe Lys Pro Thr Asp Thr Leu Thr Leu Thr Cys Thr Val
            20                  25                  30

Ser Gly Phe Ser Leu Ser Ser Tyr Ala Ile Gly Trp Val Arg Gln Ala
        35                  40                  45
```

```
Pro Gly Asn Gly Leu Glu Trp Ile Gly Thr Ile Val Thr Ser Gly Ile
        50                  55                  60

Pro Tyr Tyr Ala Asn Trp Ala Lys Ser Arg Ser Thr Ile Thr Arg Asn
 65                  70                  75                  80

Thr Asn Leu Asn Thr Val Thr Leu Lys Met Thr Ser Leu Thr Ala Ala
                85                  90                  95

Asp Thr Ala Thr Tyr Phe Cys Ala Arg Asn Leu Asp Pro Ala Tyr Ser
            100                 105                 110

Thr Thr Arg Leu Asp Leu Trp Gly Gln Gly Thr Leu Val Thr Val Ser
            115                 120                 125

Ser Gly Gln Pro Lys Ala Pro Ser Val Phe Pro Leu Ala Pro Cys Cys
    130                 135                 140

Gly Asp Thr Pro Ser
145

<210> SEQ ID NO 6
<211> LENGTH: 149
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6

Val Ala Val Leu Lys Gly Val Gln Cys Gln Ser Val Lys Glu Ser Glu
 1               5                  10                  15

Gly Gly Leu Phe Lys Pro Thr Asp Thr Leu Thr Leu Thr Cys Thr Val
            20                  25                  30

Ser Gly Phe Ser Leu Ser Ser Tyr Ala Ile Ser Trp Val Arg Gln Ala
        35                  40                  45

Pro Gly Asn Gly Leu Glu Trp Ile Gly Ala Ile Gly Lys Ser Gly Ser
        50                  55                  60

Ala Tyr Tyr Ala Ser Trp Ala Lys Ser Arg Ser Thr Ile Thr Arg Asn
 65                  70                  75                  80

Thr Asn Leu Asn Thr Val Ser Leu Lys Met Thr Ser Leu Thr Ala Ala
                85                  90                  95

Asp Thr Ala Thr Tyr Phe Cys Ala Arg Trp Asp Ser Val Gly Trp Thr
            100                 105                 110

Asp Ala Arg Leu Asp Leu Trp Gly Gln Gly Thr Leu Val Thr Val Ser
            115                 120                 125

Ser Gly Gln Pro Lys Ala Pro Ser Val Phe Pro Leu Ala Pro Cys Cys
    130                 135                 140

Gly Asp Thr Pro Ser
145

<210> SEQ ID NO 7
<211> LENGTH: 136
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

Leu Val Ala Val Leu Lys Gly Val Gln Cys Gln Ser Val Lys Glu Ser
 1               5                  10                  15

Glu Gly Gly Leu Phe Lys Pro Thr Asp Thr Leu Thr Leu Thr Cys Thr
```

```
                20                  25                  30
Val Ser Gly Phe Ser Leu Ser Ala Tyr Ala Ile Ser Trp Val Arg Gln
            35                  40                  45
Ala Pro Gly Asn Gly Leu Glu Trp Ile Gly Ala Ile Asn Ser Gly Gly
        50                  55                  60
Ser Ala Tyr Tyr Ala Asn Trp Ala Lys Ser Arg Ser Thr Ile Thr Arg
65                  70                  75                  80
Asn Thr Asn Leu Asn Thr Val Thr Leu Lys Met Thr Ser Leu Thr Ala
                85                  90                  95
Ala Asp Thr Ala Thr Tyr Phe Cys Ala Arg Glu Asp Ile Tyr Asp Tyr
            100                 105                 110
Gly Gly Ala Phe Asp Pro Trp Gly Pro Gly Thr Leu Val Thr Val Ser
        115                 120                 125
Thr Gly Gln Pro Lys Leu His His
    130                 135

<210> SEQ ID NO 8
<211> LENGTH: 147
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

Val Ala Val Leu Lys Gly Val Gln Cys Gln Ser Val Lys Glu Ser Glu
1               5                   10                  15
Gly Gly Leu Phe Lys Pro Thr Asp Thr Leu Thr Leu Thr Cys Thr Val
            20                  25                  30
Ser Gly Phe Ser Leu Ser Ile Tyr Gly Val Ser Trp Val Arg Gln Ala
        35                  40                  45
Pro Gly Asn Gly Leu Glu Trp Ile Gly Ile Ile Tyr Ala Ser Gly Ser
    50                  55                  60
Ala Asp Tyr Ala Ser Trp Ala Lys Ser Arg Ser Thr Ile Thr Arg Asn
65                  70                  75                  80
Thr Asn Leu Asn Thr Val Thr Leu Lys Met Thr Ser Leu Thr Ala Ala
                85                  90                  95
Asp Thr Ala Thr Tyr Phe Cys Ala Arg Glu Asp Asp Thr Tyr Gly Tyr
            100                 105                 110
Thr Ser Ser Ile Trp Gly Pro Gly Thr Leu Val Thr Val Ser Ser Gly
        115                 120                 125
Gln Pro Lys Ala Pro Ser Val Phe Pro Leu Ala Pro Cys Cys Gly Asp
    130                 135                 140
Thr Pro Ser
145

<210> SEQ ID NO 9
<211> LENGTH: 146
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

Leu Val Ala Val Leu Lys Gly Val Gln Cys Gln Ser Val Lys Glu Ser
1               5                   10                  15
```

Glu Gly Gly Leu Phe Lys Pro Thr Asp Thr Leu Thr Leu Thr Cys Thr
            20                  25                  30

Val Ser Gly Phe Ser Leu Ser Ser Tyr Pro Ile Ser Trp Val Arg Gln
        35                  40                  45

Ala Pro Gly Asn Gly Leu Glu Trp Ile Gly Asp Ile Tyr Ala Ser Gly
    50                  55                  60

Ser Ile Leu Tyr Ala Ser Trp Ala Thr Gly Arg Ser Thr Ile Thr Arg
65                  70                  75                  80

Asn Thr Asn Leu Asn Thr Val Thr Leu Lys Met Thr Ser Leu Thr Ala
                85                  90                  95

Ala Asp Thr Ala Thr Tyr Phe Cys Ala Arg Val Ser Tyr Ser Gly Gly
            100                 105                 110

Thr Asp Ile Trp Gly Pro Gly Thr Leu Val Thr Val Ser Ser Gly Gln
            115                 120                 125

Pro Lys Ala Pro Ser Val Phe Pro Leu Ala Pro Cys Cys Gly Asp Thr
        130                 135                 140

Pro Ser
145

<210> SEQ ID NO 10
<211> LENGTH: 148
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Leu Val Ala Val Leu Lys Gly Val Gln Cys Gln Ser Val Lys Glu Ser
1               5                   10                  15

Glu Gly Gly Leu Phe Lys Pro Thr Asp Thr Leu Thr Leu Thr Cys Thr
            20                  25                  30

Val Ser Gly Phe Ser Leu Ser Ser Asn Val Ile Ser Trp Val Arg Gln
        35                  40                  45

Ala Pro Gly Lys Gly Leu Glu Trp Ile Gly Asp Ile Tyr Val Ser Gly
    50                  55                  60

Asn Thr Asp Tyr Ala Ser Trp Ala Lys Ser Arg Ser Thr Ile Thr Arg
65                  70                  75                  80

Asn Ala Asn Leu Asn Thr Val Thr Leu Lys Met Thr Ser Leu Thr Ala
                85                  90                  95

Ala Asp Thr Ala Thr Tyr Phe Cys Ala Arg Tyr Asp Met Ser Ser Asp
            100                 105                 110

Ala Phe Asp Pro Trp Gly Pro Gly Thr Leu Val Thr Val Ser Ser Gly
            115                 120                 125

Gln Pro Lys Ala Pro Ser Val Phe Pro Leu Ala Pro Cys Cys Gly Asp
        130                 135                 140

Thr Pro Ser Ser
145

<210> SEQ ID NO 11
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

```
Trp Leu Pro Gly Ala Arg Cys Ala Tyr Asp Met Thr Gln Thr Pro Ala
1               5                   10                  15

Ser Val Glu Val Ala Val Gly Gly Thr Val Thr Ile Lys Cys Gln Ala
                20                  25                  30

Ser Gln Ser Ile Ser Thr Ala Leu Ala Trp Tyr Gln Gln Lys Pro Gly
            35                  40                  45

Gln Pro Pro Lys Leu Leu Ile Tyr Gly Ala Ser Thr Leu Ala Ser Gly
        50                  55                  60

Val Ser Ser Arg Phe Lys Gly Ser Gly Ser Gly Thr Gln Phe Thr Leu
65                  70                  75                  80

Thr Ile Ser Gly Val Glu Cys Ala Asp Ala Ala Thr Tyr Tyr Cys Gln
                85                  90                  95

Gln Gly Tyr Ser Thr Ser Asp Val Asp Asn Ala Phe Gly Gly Gly Thr
            100                 105                 110

Glu Gly
```

<210> SEQ ID NO 12
<211> LENGTH: 134
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

```
Leu Trp Leu Pro Gly Ala Arg Cys Ala Tyr Asp Met Thr Gln Thr Pro
1               5                   10                  15

Ala Ser Val Ser Ala Ala Val Gly Gly Thr Val Thr Ile Lys Cys Gln
                20                  25                  30

Ala Ser Glu Ser Ile Ser Thr Tyr Leu Ser Trp Leu Gln Gln Lys Pro
            35                  40                  45

Gly Gln Pro Pro Lys Leu Leu Ile Tyr Lys Ala Ser Thr Leu Ala Ser
        50                  55                  60

Gly Val Pro Ser Arg Phe Lys Gly Ser Gly Ser Gly Thr Glu Phe Thr
65                  70                  75                  80

Leu Thr Ile Ser Gly Val Gln Cys Asp Asp Ala Ala Thr Tyr Tyr Cys
                85                  90                  95

Gln Gln Asp Tyr Thr Ile Ser Asn Val Gly Asn Val Phe Gly Gly Gly
            100                 105                 110

Thr Glu Val Val Val Lys Gly Asp Pro Val Ala Pro Thr Val Leu Ile
        115                 120                 125

Phe Pro Pro Ser Ala Asp
        130
```

<210> SEQ ID NO 13
<211> LENGTH: 134
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

```
Leu Trp Leu Pro Gly Ala Arg Cys Ala Tyr Asp Met Thr Gln Thr Pro
1               5                   10                  15
```

-continued

Ala Ser Val Glu Val Ala Val Gly Gly Thr Val Thr Ile Lys Cys Gln
                20                  25                  30

Ala Ser Glu Ser Ile Ser Ser Tyr Leu Ser Trp Tyr Gln Gln Lys Pro
            35                  40                  45

Gly Gln Pro Pro Lys Leu Leu Ile Tyr Arg Ala Ser Thr Leu Ala Ser
 50                  55                  60

Gly Val Pro Ser Arg Phe Ser Gly Ser Gly Ser Gly Thr Glu Phe Thr
 65                  70                  75                  80

Leu Thr Ile Ser Asp Gly Gln Cys Asp Asp Ala Ala Thr Tyr Tyr Cys
                85                  90                  95

Gln Gln Gly Tyr Ser Val Ser Asn Val Asp Asn Ile Phe Gly Gly Gly
                100                 105                 110

Thr Glu Val Val Val Lys Gly Asp Pro Val Ala Pro Thr Val Leu Ile
            115                 120                 125

Phe Pro Pro Ser Ala Asp
        130

<210> SEQ ID NO 14
<211> LENGTH: 132
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

Trp Leu Pro Gly Ala Arg Cys Ala Tyr Asp Met Thr Gln Thr Pro Ala
1               5                   10                  15

Ser Val Glu Val Ala Val Gly Gly Thr Val Thr Ile Lys Cys Gln Ala
                20                  25                  30

Ser Gln Ser Ile Asn Asn Tyr Leu Ser Trp Tyr Gln Gln Ile Pro Gly
            35                  40                  45

Gln Pro Pro Lys Leu Leu Ile Tyr Arg Ala Ser Thr Leu Ala Ser Gly
 50                  55                  60

Val Ser Ser Arg Phe Lys Gly Ser Gly Ser Gly Thr Gln Phe Thr Leu
 65                  70                  75                  80

Thr Ile Ser Gly Val Gln Cys Ala Asp Ala Ala Thr Tyr Tyr Cys Gln
                85                  90                  95

Gln Gly Tyr Thr Ser Asn Val Asp Asn Val Phe Gly Gly Gly Thr Glu
                100                 105                 110

Val Val Val Lys Gly Asp Pro Val Ala Pro Thr Val Leu Ile Phe Pro
            115                 120                 125

Pro Ser Ala Asp
    130

<210> SEQ ID NO 15
<211> LENGTH: 130
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Trp Leu Pro Gly Ala Arg Cys Ala Tyr Asp Met Thr Gln Thr Pro Ala
1               5                   10                  15

```
Ser Val Ser Glu Pro Val Arg Gly Thr Val Thr Ile Lys Cys Gln Ala
            20                  25                  30

Ser Gln Ser Ile Ser Thr Ala Leu Ala Trp Tyr Gln Gln Lys Pro Gly
            35                  40                  45

Gln Pro Pro Lys Leu Leu Ile Tyr Ala Ala Ser Tyr Leu Ala Ser Gly
        50                  55                  60

Val Pro Ser Arg Phe Ser Gly Ser Gly Ser Gly Thr Glu Phe Thr Leu
65                  70                  75                  80

Thr Ile Ser Asp Leu Glu Cys Ala Asp Ala Ala Thr Tyr Tyr Cys His
                85                  90                  95

Gln Gly Tyr Ser Ala Ser Asn Val Asp Asn Thr Phe Gly Gly Gly Thr
            100                 105                 110

Glu Gly Gly Val Lys Gly Asp Pro Val Ala Pro Thr Val Leu Ile Phe
            115                 120                 125

Pro Pro
    130
```

<210> SEQ ID NO 16
<211> LENGTH: 133
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

```
Trp Leu Pro Gly Ala Arg Cys Ala Tyr Asp Met Thr Gln Thr Pro Ala
1               5                   10                  15

Ser Val Glu Val Ala Val Gly Gly Thr Val Thr Ile Lys Cys Gln Ala
            20                  25                  30

Ser Gln Ser Ile Ser Thr Ala Leu Ala Trp Tyr Gln Gln Lys Pro Gly
            35                  40                  45

Gln Arg Pro Lys Leu Leu Ile Tyr Gly Ala Ser Lys Leu Ala Ser Gly
        50                  55                  60

Val Ser Ser Arg Phe Ser Gly Ser Gly Ser Gly Thr Glu Phe Thr Leu
65                  70                  75                  80

Thr Ile Ser Gly Val Glu Cys Ala Asp Ala Ala Thr Tyr Tyr Cys Gln
                85                  90                  95

Gln Gly Tyr Glu Thr Ser Asn Val Asp Asn Ala Phe Gly Gly Gly Thr
            100                 105                 110

Glu Val Val Val Lys Gly Asp Pro Val Ala Pro Thr Val Leu Ile Phe
            115                 120                 125

Pro Pro Ser Ala Asp
    130
```

<210> SEQ ID NO 17
<211> LENGTH: 133
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

```
Trp Leu Pro Gly Ala Arg Cys Ala Tyr Asp Met Thr Gln Thr Pro Ala
1               5                   10                  15

Ser Val Glu Val Thr Val Gly Gly Thr Val Thr Ile Lys Cys Gln Ala
```

```
            20                  25                  30

Ser Gln Gly Ile Ser Ser Tyr Leu Ser Trp Tyr Gln Gln Lys Pro Gly
        35                  40                  45

Gln Pro Pro Lys Leu Leu Ile Tyr Ala Ala Thr Thr Leu Val Ser Gly
    50                  55                  60

Val Ser Ser Arg Phe Lys Gly Ser Gly Ser Gly Thr Gln Phe Thr Leu
65                  70                  75                  80

Thr Ile Ser Gly Val Glu Cys Ala Asp Ala Ala Thr Tyr Tyr Cys Gln
                85                  90                  95

Gln Asp Tyr Thr Thr Ser Asn Val Asp Asn Thr Phe Gly Gly Gly Thr
            100                 105                 110

Glu Val Val Val Lys Gly Asp Pro Val Ala Pro Thr Val Leu Ile Phe
        115                 120                 125

Pro Pro Ser Ala Asp
    130

<210> SEQ ID NO 18
<211> LENGTH: 130
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

Trp Leu Pro Gly Ala Arg Cys Ala Tyr Asp Met Thr Gln Thr Pro Ala
1               5                   10                  15

Ser Val Ser Ala Ala Val Gly Gly Thr Val Thr Ile Lys Cys Gln Ala
            20                  25                  30

Ser Gln Ser Ile Ser Ser Tyr Leu Asn Trp Tyr Gln Gln Lys Pro Gly
        35                  40                  45

Gln Pro Pro Lys Arg Leu Ile Tyr Arg Ala Ser Thr Leu Ala Ser Gly
    50                  55                  60

Val Ser Ser Arg Phe Lys Gly Ser Gly Ser Gly Thr Gln Phe Thr Leu
65                  70                  75                  80

Thr Ile Ser Gly Val Glu Cys Ala Asp Ala Ala Thr Tyr Tyr Cys Gln
                85                  90                  95

Gln Asp Tyr Ser Ser Asn Asn Ile Asp Asn Thr Phe Gly Gly Gly Thr
            100                 105                 110

Glu Val Val Val Lys Gly Asp Pro Val Ala Pro Thr Val Leu Ile Phe
        115                 120                 125

Pro Pro
    130

<210> SEQ ID NO 19
<211> LENGTH: 130
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19

Trp Leu Pro Gly Ala Arg Cys Ala Tyr Asp Met Thr Gln Thr Pro Ala
1               5                   10                  15

Ser Val Glu Val Ala Val Gly Gly Thr Val Thr Ile Lys Cys Gln Ala
            20                  25                  30
```

```
Ser Glu Asp Ile Glu Ser Tyr Leu Ala Trp Tyr Gln Gln Lys Pro Gly
            35                  40                  45

Gln Pro Pro Lys Leu Leu Ile Tyr Arg Ala Ser Thr Leu Pro Ser Gly
    50                  55                  60

Val Pro Ser Arg Phe Lys Gly Ser Gly Ser Gly Thr Glu Phe Thr Leu
65                  70                  75                  80

Thr Ile Ser Asp Leu Glu Cys Ala Asp Ala Ala Thr Tyr Tyr Cys Gln
                85                  90                  95

Gln Asp Tyr Ser Ser Ser Asn Val Asp Asn Thr Phe Gly Gly Gly Thr
                100                 105                 110

Glu Val Val Val Lys Gly Asp Pro Val Ala Pro Thr Val Leu Ile Phe
            115                 120                 125

Pro Pro
    130

<210> SEQ ID NO 20
<211> LENGTH: 133
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

Leu Trp Leu Pro Gly Ala Arg Cys Ala Tyr Asp Met Thr Gln Thr Pro
1               5                   10                  15

Ala Ser Val Glu Val Ala Val Gly Gly Thr Val Thr Ile Lys Cys Gln
            20                  25                  30

Ala Ser Gln Asn Ile Gly Ser Tyr Leu Ser Trp Tyr Gln His Lys Pro
            35                  40                  45

Gly Gln Arg Pro Arg Leu Leu Met Tyr Arg Ala Ser Thr Leu Ala Ser
    50                  55                  60

Gly Val Ser Ser Arg Phe Lys Gly Ser Gly Ser Gly Thr Glu Phe Thr
65                  70                  75                  80

Leu Thr Ile Ser Gly Val Gln Cys Asp Asn Ala Ala Thr Tyr Tyr Cys
                85                  90                  95

Gln Gln Gly Tyr Thr Asn Ser Gly Val Asp Asn Thr Phe Gly Gly Gly
                100                 105                 110

Thr Glu Val Val Val Lys Gly Asp Pro Val Ala Pro Thr Val Leu Ile
            115                 120                 125

Phe Pro Pro Ser Ala
    130

<210> SEQ ID NO 21
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Ser Ser Asn Ala Ile Ser
1               5

<210> SEQ ID NO 22
<211> LENGTH: 6
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Ser Ser Tyr Ala Ile Ser
1               5

<210> SEQ ID NO 23
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Ser Ser Tyr Gly Val Ser
1               5

<210> SEQ ID NO 24
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Ser Ser Tyr Ala Ile Ser
1               5

<210> SEQ ID NO 25
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25

Ser Ser Tyr Ala Ile Gly
1               5

<210> SEQ ID NO 26
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

Ser Ser Tyr Ala Ile Ser
1               5

<210> SEQ ID NO 27
<211> LENGTH: 6
<212> TYPE: PRT
<213> ORGANISM: Artificial Sequence
<220> FEATURE:
<221> NAME/KEY: source
```

<223> OTHER INFORMATION: /note="Description of Artificial Sequence:
      Synthetic peptide"

<400> SEQUENCE: 27

Ser Ala Tyr Ala Ile Ser
1               5

<210> SEQ ID NO 28
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Ser Ile Tyr Gly Val Ser
1               5

<210> SEQ ID NO 29
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Ser Ser Tyr Pro Ile Ser
1               5

<210> SEQ ID NO 30
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 30

Ser Ser Asn Val Ile Ser
1               5

<210> SEQ ID NO 31
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Ala Ile Gly Ser Ser Gly Ser Thr Tyr Tyr Ala Ser Trp Ala Lys Ser
1               5                   10                  15

<210> SEQ ID NO 32
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32

```
Arg Ile Asn Ser Gly Gly Ala Thr Asp Tyr Ala Ser Trp Ala Arg Ser
1               5                   10                  15

<210> SEQ ID NO 33
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 33

Ser Ile Trp Ser Gly Gly Thr Thr Asp Tyr Ala Ser Trp Ala Lys Ser
1               5                   10                  15

<210> SEQ ID NO 34
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

Ala Ile Asn Thr Tyr Gly Gly Thr Tyr Tyr Ala Ser Trp Ala Lys Ser
1               5                   10                  15

<210> SEQ ID NO 35
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 35

Thr Ile Val Thr Ser Gly Ile Pro Tyr Tyr Ala Asn Trp Ala Lys Ser
1               5                   10                  15

<210> SEQ ID NO 36
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 36

Ala Ile Gly Lys Ser Gly Ser Ala Tyr Tyr Ala Ser Trp Ala Lys Ser
1               5                   10                  15

<210> SEQ ID NO 37
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 37

Ala Ile Asn Ser Gly Gly Ser Ala Tyr Tyr Ala Asn Trp Ala Lys Ser
1               5                   10                  15
```

<210> SEQ ID NO 38
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 38

Ile Ile Tyr Ala Ser Gly Ser Ala Asp Tyr Ala Ser Trp Ala Lys Ser
1               5                   10                  15

<210> SEQ ID NO 39
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 39

Asp Ile Tyr Ala Ser Gly Ser Ile Leu Tyr Ala Ser Trp Ala Thr Gly
1               5                   10                  15

<210> SEQ ID NO 40
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 40

Asp Ile Tyr Val Ser Gly Asn Thr Asp Tyr Ala Ser Trp Ala Lys Ser
1               5                   10                  15

<210> SEQ ID NO 41
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 41

Arg Trp Glu Asn Ile Gly Tyr Thr Asn Val Arg Leu Asp Leu
1               5                   10

<210> SEQ ID NO 42
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42

Lys Glu Glu Tyr Ser Tyr Gly Gly Ala Tyr Gly Met
1               5                   10

<210> SEQ ID NO 43
<211> LENGTH: 12
<212> TYPE: PRT

-continued

<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 43

Arg Gly Gly Tyr Asp Tyr Gly Tyr Ala Ser Asn Ile
1               5                   10

<210> SEQ ID NO 44
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Arg Asp Phe Asp Ser Asp Ala Tyr Thr Ser Ala Ser Gly Gly Met Asp
1               5                   10                  15

Pro

<210> SEQ ID NO 45
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45

Arg Asn Leu Asp Pro Ala Tyr Ser Thr Thr Arg Leu Asp Leu
1               5                   10

<210> SEQ ID NO 46
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 46

Arg Trp Asp Ser Val Gly Trp Thr Asp Ala Arg Leu Asp Leu
1               5                   10

<210> SEQ ID NO 47
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 47

Arg Glu Asp Ile Tyr Asp Tyr Gly Gly Ala Phe Asp Pro
1               5                   10

<210> SEQ ID NO 48
<211> LENGTH: 12
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic peptide"

<400> SEQUENCE: 48

Arg Glu Asp Asp Thr Tyr Gly Tyr Thr Ser Ser Ile
1               5                   10

<210> SEQ ID NO 49
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

Arg Val Ser Tyr Ser Gly Gly Thr Asp Ile
1               5                   10

<210> SEQ ID NO 50
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 50

Arg Tyr Asp Met Ser Ser Asp Ala Phe Asp Pro
1               5                   10

<210> SEQ ID NO 51
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 51

Gln Ala Ser Gln Ser Ile Ser Thr Ala Leu Ala
1               5                   10

<210> SEQ ID NO 52
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 52

Gln Ala Ser Glu Ser Ile Ser Thr Tyr Leu Ser
1               5                   10

<210> SEQ ID NO 53
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 53

Gln Ala Ser Glu Ser Ile Ser Ser Tyr Leu Ser
1               5                   10

<210> SEQ ID NO 54
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 54

Gln Ala Ser Gln Ser Ile Asn Asn Tyr Leu Ser
1               5                   10

<210> SEQ ID NO 55
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 55

Gln Ala Ser Gln Ser Ile Ser Thr Ala Leu Ala
1               5                   10

<210> SEQ ID NO 56
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 56

Gln Ala Ser Gln Ser Ile Ser Thr Ala Leu Ala
1               5                   10

<210> SEQ ID NO 57
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 57

Gln Ala Ser Gln Gly Ile Ser Ser Tyr Leu Ser
1               5                   10

<210> SEQ ID NO 58
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 58

Gln Ala Ser Gln Ser Ile Ser Ser Tyr Leu Asn
1               5                   10
```

```
<210> SEQ ID NO 59
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 59

Gln Ala Ser Glu Asp Ile Glu Ser Tyr Leu Ala
1               5                   10

<210> SEQ ID NO 60
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 60

Gln Ala Ser Gln Asn Ile Gly Ser Tyr Leu Ser
1               5                   10

<210> SEQ ID NO 61
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 61

Gly Ala Ser Thr Leu Ala Ser
1               5

<210> SEQ ID NO 62
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 62

Lys Ala Ser Thr Leu Ala Ser
1               5

<210> SEQ ID NO 63
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 63

Arg Ala Ser Thr Leu Ala Ser
1               5

<210> SEQ ID NO 64
<211> LENGTH: 7
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 64

Arg Ala Ser Thr Leu Ala Ser
1               5

<210> SEQ ID NO 65
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 65

Ala Ala Ser Tyr Leu Ala Ser
1               5

<210> SEQ ID NO 66
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 66

Gly Ala Ser Lys Leu Ala Ser
1               5

<210> SEQ ID NO 67
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 67

Ala Ala Thr Thr Leu Val Ser
1               5

<210> SEQ ID NO 68
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 68

Arg Ala Ser Thr Leu Ala Ser
1               5

<210> SEQ ID NO 69
<211> LENGTH: 7
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"

<400> SEQUENCE: 69

Arg Ala Ser Thr Leu Pro Ser
1               5

<210> SEQ ID NO 70
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 70

Arg Ala Ser Thr Leu Ala Ser
1               5

<210> SEQ ID NO 71
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 71

Gln Gln Gly Tyr Ser Thr Ser Asp Val Asp Asn Ala
1               5                   10

<210> SEQ ID NO 72
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 72

Gln Gln Asp Tyr Thr Ile Ser Asn Val Gly Asn Val
1               5                   10

<210> SEQ ID NO 73
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 73

Gln Gln Gly Tyr Ser Val Ser Asn Val Asp Asn Ile
1               5                   10

<210> SEQ ID NO 74
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 74
```

Gln Gln Gly Tyr Thr Ser Asn Val Asp Asn Val Phe
1               5                   10

<210> SEQ ID NO 75
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 75

His Gln Gly Tyr Ser Ala Ser Asn Val Asp Asn Thr
1               5                   10

<210> SEQ ID NO 76
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 76

Gln Gln Gly Tyr Glu Thr Ser Asn Val Asp Asn Ala
1               5                   10

<210> SEQ ID NO 77
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 77

Gln Gln Asp Tyr Thr Thr Ser Asn Val Asp Asn Thr
1               5                   10

<210> SEQ ID NO 78
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 78

Gln Gln Asp Tyr Ser Ser Asn Asn Ile Asp Asn Thr
1               5                   10

<210> SEQ ID NO 79
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 79

Gln Gln Asp Tyr Ser Ser Ser Asn Val Asp Asn Thr
1               5                   10

```
<210> SEQ ID NO 80
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 80

Gln Gln Gly Tyr Thr Asn Ser Gly Val Asp Asn Thr
1               5                   10

<210> SEQ ID NO 81
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 81

Met Lys Val Thr Gly Ile Phe Leu Leu Ser Ala Leu Ala Leu Leu Ser
1               5                   10                  15

Leu Ser Gly Asn Thr Gly Ala
            20

<210> SEQ ID NO 82
<211> LENGTH: 79
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 82

Met Lys Val Thr Gly Ile Phe Leu Leu Ser Ala Leu Ala Leu Leu Ser
1               5                   10                  15

Leu Ser Gly Asn Thr Gly Ala Asp Ser Leu Gly Arg Glu Ala Lys Cys
            20                  25                  30

Tyr Asn Glu Leu Asn Gly Cys Thr Lys Ile Tyr Asp Pro Val Cys Gly
        35                  40                  45

Thr Asp Gly Asn Thr Tyr Pro Asn Glu Cys Val Leu Cys Phe Glu Asn
    50                  55                  60

Arg Lys Arg Gln Thr Ser Ile Leu Ile Gln Lys Ser Gly Pro Cys
65                  70                  75

<210> SEQ ID NO 83
<211> LENGTH: 56
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 83

Asp Ser Leu Gly Arg Glu Ala Lys Cys Tyr Asn Glu Leu Asn Gly Cys
1               5                   10                  15

Thr Lys Ile Tyr Asp Pro Val Cys Gly Thr Asp Gly Asn Thr Tyr Pro
            20                  25                  30

Asn Glu Cys Val Leu Cys Phe Glu Asn Arg Lys Arg Gln Thr Ser Ile
```

```
                    35                  40                  45
Leu Ile Gln Lys Ser Gly Pro Cys
    50                  55
```

<210> SEQ ID NO 84
<211> LENGTH: 453
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 84

```
ctggtcgctg tgctcaaagg tgtccagtgt cagtcggtga aggagtccga gggaggtctc    60
ttcaagccaa cggataccct gacactcacc tgcacagtct ctggattctc cctcagtagc   120
aatgcaataa gctgggtccg ccaggctcca gggaacgggc tggaatggat cggagccatt   180
ggtagtagtg gtagcacata ctacgcgagc tgggcgaaaa gccgatccac cgtcaccaga   240
aacaccaacc tgaacacggt gactctaaag atgaccagtc tgacagccgc ggacacggcc   300
acctatttct gtgcgagatg ggagaatatt ggttatacta atgttcggtt ggatctctgg   360
ggccagggca ccctggtcac cgtctcctca gggcaaccta aggctccatc agtcttccca   420
ctggccccct gctgcgggga cacacccagc tcc                                453
```

<210> SEQ ID NO 85
<211> LENGTH: 343
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 85

```
tggctcccag gtgccagatg tgcctatgat atgacccaga ctccagcctc tgtggaggta    60
gctgtgggag gcacagtcac catcaagtgc caggccagtc agagcattag cactgcatta   120
gcctggtatc agcagaaacc agggcagcct cccaagctcc tgatctatgg tgcatccact   180
ctggcatctg gggtctcatc gcggttcaaa ggcagtggat ctgggacaca gttcactctc   240
accatcagcg gcgtggagtg tgccgatgct gccacttact actgtcaaca gggttatagt   300
actagtgatg ttgataatgc tttcggcgga gggaccgagg gg                      343
```

<210> SEQ ID NO 86
<211> LENGTH: 445
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 86

```
ggtcgctgtg ctcaaaggtg tccagtgtca gtcggtgaag gagtccgagg gaggtctctt    60
caagccaacg ataccctga cactcacctg cacagtctct ggattctccc tcagtagcta   120
tgcaataagt tgggtccgcc aggctccagg gaacgggctg aatggatcg gcgcattaa    180 tagtggtggt gccacagact acgcgagctg ggcgagaagc cgatccacca tcaccagaga   240
caccaacctg aacacggtga ctctgcaaat gaccagtctg accgccgcgg acacggccac   300
```

```
ctatttctgt gcgaaagaag agtatagtta tggtggtgct tatggtatgt ggggcccagg    360
cactctggtc accgtctcct cagggcaacc taaggctcca tcagtcttcc cactggcccc    420
ctgctgcggg gacacaccca gctcc                                          445
```

<210> SEQ ID NO 87
<211> LENGTH: 404
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 87

```
ctctggctcc caggtgccag atgtgcctat gatatgaccc agactccagc ctccgtgtct    60
gcagctgtgg gaggcacagt caccatcaag tgccaggcca gtgagagcat tagtacctac   120
ttatcctggt tgcagcagaa accagggcag cctcccaagc tcctgatcta caaggcttcc   180
actctggcat ctggggtccc atcgcggttc aaaggcagtg gatctgggac agagttcact   240
ctcaccatca gcgtgtgca gtgtgacgat gctgccactt actactgtca acaggattat   300
actattagta atgttggtaa tgttttcggc ggagggaccg aggtggtggt caaaggtgat   360
ccagttgcac ctactgtcct catcttccca ccatcagcgg acca                    404
```

<210> SEQ ID NO 88
<211> LENGTH: 406
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 88

```
cctggtcgct gtgctcaaag gtgtccagtg tcagtcggtg aaggagtccg agggaggtct    60
cttcaagcca acggataccc tgacactcac ctgcacagtc tctggattct ccctcagtag   120
ttatggagtg agctgggtcc gccaggctcc agggaagggg ctggagtgga tcgggtccat   180
ttggagtggt ggtaccacag actacgcgag ctgggcgaaa agccgatcca ccataaccag   240
aaacaccaac gagaacacgg tgactctgaa agtgaccagt ctgacagccg cggacacggc   300
cacctatttc tgtgcgaggg ggggttatga ttatggttat gcctcgaaca tctgggggccc   360 aggcaccctg gtcaccgtct cctcagggca acctaaggct ccatca                 406
```

<210> SEQ ID NO 89
<211> LENGTH: 404
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 89

```
ctctggctcc caggtgccag atgtgcctat gatatgaccc agactccagc ctctgtggag    60
gtagctgtgg gaggcacagt caccatcaag tgccaggcca gtgaaagcat tagcagctac   120
ttatcctggt atcagcagaa accagggcag cctcccaagc tcctgatcta cagggcttcc   180
actctggcat ctggggtccc atcgcggttc agtggcagtg gatctgggac agagttcact   240
ctcaccatca gcgacgggca gtgtgacgat gctgccactt actactgtca acagggttat   300
```

```
agtgttagta atgttgataa tattttcggc ggagggaccg aggtggtggt caaaggtgat    360
ccagttgcac ctactgtcct catcttccca ccatcagcgg acca                    404

<210> SEQ ID NO 90
<211> LENGTH: 459
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 90
cctggtcgct gtgctcaaag gtgtccagtg tcagtcggtg aaggagtccg agggaggtct    60
cttcaagcca acggatgccc tgacactcac ctgcacagtc tctggattct ccctcagtag   120
ctatgcaata agctgggtcc gccaggctcc agggagcggg ctggaatgga tcggagccat   180
taatacttat ggtggcacat actacgcgag ctgggcgaaa agccgatcca ccatcaccag   240
aaacaccaac gagaacacgg tgactctgaa aatgaccagt ctgacagccg cggacacggc   300
cacctatttc tgtgcgagag acttcgatag tgatgcttat acttctgcta gtgggggcat   360
ggacccctgg ggcccaggga ccctcgtcac cgtctcttca gggcaaccta aggctccatc   420
attcttccca ctggcccct gctgcgggga cacacccag                           459

<210> SEQ ID NO 91
<211> LENGTH: 400
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 91
tctggctccc aggtgccaga tgtgcctatg atatgaccca gactccagcc tctgtggagg    60
tagctgtggg aggcacagtc accatcaagt gccaggccag tcagagcatt aacaactact   120
tatcctggta tcagcaaata ccagggcagc ctcccaagct cctgatctac agggcatcca   180
ctctggcatc tggggtctca tcgcggttca aaggcagtgg atctgggaca cagttcactc   240
tcaccatcag cggcgtgcag tgtgccgatg ctgccactta ctactgtcaa cagggttata   300
ctagtaatgt tgataatgtt ttcggcggag ggaccgaggt ggtggtcaaa ggtgatccag   360
ttgcacctac tgtcctcatc ttcccaccat cagcggacca                         400

<210> SEQ ID NO 92
<211> LENGTH: 450
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 92
ggtcgctgtg ctcaaaggtg tccagtgtca gtcggtgaag gagtccgagg gaggtctctt    60
caagccaacg gatacctga cactcacctg cacagtctct ggattctccc tcagtagcta   120
tgcaataggc tgggtccgcc aggctccagg aacgggctg gaatggatcg gaaccattgt   180
tactagtggt atcccatact acgcgaactg ggcgaaaagc cgatccacca tcaccagaaa   240
```

```
caccaacctg aacacggtga ctctgaaaat gaccagtctg acagccgcgg acacggccac    300
ctatttctgt gcgagaaatt tagatcctgc ttatagtacc actcggttgg atctctgggg    360
ccagggcacc ctggtcaccg tctcctcagg gcaacctaag gctccatcag tcttcccact    420
ggccccctgc tgcggggaca cacccagctc                                     450
```

<210> SEQ ID NO 93
<211> LENGTH: 394
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 93

```
tctggctccc aggtgccaga tgtgcctatg atatgaccca gactccagcc tccgtgtctg     60
aacctgtgag aggcacagtc accatcaagt gccaggccag tcagagcatt agcactgcat    120
tagcctggta tcagcagaaa ccagggcagc ctcccaagct cctgatctat gctgcatcct    180
atctggcctc tggggtccca tcgcggttca gcggcagtgg atctgggaca gagttcactc    240
tcaccatcag cgacctggag tgtgccgatg ctgccactta ctactgtcat cagggttata    300
gtgctagtaa tgttgataat actttcggcg agggaccgga gggggggtc aaaggtgatc     360 cagttgcacc tactgtcctc atcttcccac catc                                394
```

<210> SEQ ID NO 94
<211> LENGTH: 450
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 94

```
ggtcgctgtg ctcaaaggtg tccagtgtca gtcagtgaag gagtccgagg gaggtctctt     60
caagccaacg gataccctga cactcacctg cacagtctct ggattctccc tcagtagcta    120
tgcaataagt tgggtccgcc aggctccagg gaacgggctg gaatggatcg gagccattgg    180
taaaagtggt agcgcatact acgcgagctg ggcgaaaagc cgatccacca tcaccagaaa    240
caccaacctg aacacggtgt cgctgaaaat gaccagtctg acagccgcgg acacggccac    300
ctatttctgt gcgagatggg atagtgttgg ttggactgat gctcggttgg atctctgggg    360
ccagggcacc ctggtcaccg tctcctcagg gcaacctaag gctccatcag tcttcccact    420
ggccccctgc tgcggggaca cacccagctc                                     450
```

<210> SEQ ID NO 95
<211> LENGTH: 402
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 95

```
ctggctccca ggtgccagat gtgcctatga tatgacccag actccagcct ctgtggaggt     60
agctgtggga ggcacagtca ccatcaagtg ccaggccagt cagagcatta gcactgcatt    120
agcctggtat cagcagaaac cagggcagcg tcccaagctc ctgatctatg gtgcatcgaa    180
```

```
actggcatct ggggtctcat cgcggttcag tggcagtgga tctgggacag agttcactct    240
caccatcagc ggcgtggagt gtgccgatgc tgccacttac tactgtcaac agggttatga    300
aactagtaat gttgataatg ctttcggcgg agggaccgag gtggtggtca aggtgatcc     360 agttgcacct actgtcctca tcttcccacc atcagcggac ca                       402
```

<210> SEQ ID NO 96
<211> LENGTH: 408
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 96

```
ctggtcgctg tgctcaaagg tgtccagtgt cagtcggtga aggagtccga gggaggtctc     60
ttcaagccaa cggatacccct gacactcacc tgcacagtct ctggattctc cctcagtgcc   120
tatgcaataa gctgggtccg ccaggctcca gggaacgggc tggaatggat cggagccatt    180
aatagtggtg gtagcgcata ctacgcgaac tgggcgaaaa gccgatccac catcaccaga    240
aacaccaacc tgaacacggt gactctgaaa atgaccagtc tgacagccgc ggacacggcc    300
acctatttct gtgcgaggga agatatttat gattatggtg gtgcattcga tccctggggc    360
ccaggcaccc tggtcaccgt ctccacaggg caacctaagc tccatcat                 408
```

<210> SEQ ID NO 97
<211> LENGTH: 401
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 97

```
ctggctccca ggtgccagat gtgcctatga tatgacccag actccagcct ctgtggaggt     60
aactgtggga ggcacagtca ccatcaagtg ccaggccagt caaggcatta gtagttactt    120
atcctggtat cagcagaaac cagggcagcc tcccaagctc ctgatctatg ctgcgaccac    180
tctggtatct ggggtctcat cgcggttcaa aggcagtgga tctgggacac agttcactct    240
caccatcagc ggcgtggagt gtgccgatgc tgccacttac tactgtcagc aggattatac    300
tactagtaat gttgataata ctttcggcgg agggaccgag gtggtggtca aggtgatcc     360 agttgcacct actgtcctca tcttcccacc atcagcggac c                        401
```

<210> SEQ ID NO 98
<211> LENGTH: 443
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 98

```
gtcgctgtgc tcaaaggtgt ccagtgtcag tcggtgaagg agtccgaggg aggtctcttc     60
aagccaacgg ataccctgac actcacctgc acagtctctg gattctccct cagcatctat    120
ggagtgagct gggtccgcca ggctccaggg aacgggctgg aatggatcgg aatcattttat   180
```

```
gctagtggta gcgcagacta cgcgagctgg gcgaaaagcc gatccaccat caccagaaac    240
accaacctga acacggtgac tctgaagatg accagtctga cagccgcgga cacggccacc    300
tatttctgtg cgagagagga cgatacttat ggttatacta gtagtatatg gggcccaggc    360
accctggtca ccgtctcctc agggcaacct aaggctccat cagtcttccc actggccccc    420
tgctgcgggg acacacccag ctc                                            443
```

<210> SEQ ID NO 99
<211> LENGTH: 391
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 99

```
tggctcccag gtgccagatg tgcctatgat atgacccaga ctccagcctc cgtgtctgca     60
gctgtgggag gcacagtcac catcaagtgc caggccagtc agagcattag tagctactta    120
aactggtatc agcagaaacc agggcagcct cccaagcgcc tgatctacag ggcatccact    180
ctggcatctg ggtctcatcg cggttcaaa ggcagtggat ctgggacaca gttcactctc     240
accatcagcg gcgtggagtg tgccgatgct gccacttact actgtcaaca ggattatagt    300
agtaataata ttgataatac tttcggcgga gggaccgagg tggtggtcaa aggtgatcca    360
gttgcaccta ctgtcctcat cttcccacca t                                   391
```

<210> SEQ ID NO 100
<211> LENGTH: 440
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 100

```
ctggtcgctg tgctcaaagg tgtccagtgt cagtcggtga aggagtccga gggaggtctc     60
ttcaagccaa cggataccct gacactcacc tgcacagtct ctggattctc cctcagtagc    120
tatccaataa gctgggtccg ccaggctcca gggaacgggc tggaatggat cggagacatt    180
tatgctagtg gtagtatatt gtacgcgagc tgggcgacag gccgatctac catcaccaga    240
aataccaacc tgaacacggt gactctgaaa atgaccagtc tgacagccgc ggacacggcc    300
acctatttct gtgcgagagt aagttatagt ggtggtaccg acatctgggg cccaggcacc    360
ctggtcaccg tctcctcagg gcaacctaag gctccatcag tcttcccact ggccccctgc    420
tgcggggaca cacccagctc                                                440
```

<210> SEQ ID NO 101
<211> LENGTH: 394
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 101

```
tctggctccc aggtgccaga tgtgcctatg atatgaccca gactccagcc tctgtggagg     60
tagctgtggg aggcacagtc accatcaagt gccaggccag tgaggacatt gaaagctatt    120
```

```
tagcctggta tcagcagaaa ccagggcagc ctcccaagct cctgatctac agggcatcca    180
ctctgccatc tggggtccca tcgcggttca aaggcagtgg atctgggaca gagttcactc    240
tcaccatcag cgacctggag tgtgccgatg ctgccactta ctactgtcaa caggattata    300
gtagtagtaa tgttgataat actttcggcg gagggaccga ggtggtggtc aaaggtgatc    360
cagttgcacc tactgtcctc atcttcccac catc                                394

<210> SEQ ID NO 102
<211> LENGTH: 444
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 102
ctggtcgctg tgctcaaagg tgtccagtgt cagtcggtga aggagtccga gggaggtctc     60
ttcaagccaa cggatacc ct gacactcacc tgcacagtct ctggattctc cctcagtagc    120
aatgtaataa gctgggtccg ccaggctcca gggaaggggc tggagtggat cggagacatt    180
tatgttagtg gtaacacaga ctacgcgagc tgggcgaaaa gccgatccac catcaccaga    240
aacgccaacc tgaacacggt gactctgaaa atgaccagtc tgacagccgc ggacacggcc    300
acctatttct gtgcgagata tgatatgagt agtgatgctt tcgatccctg gggcccaggc    360
accctggtca ccgtctcctc agggcaacct aaggctccat cagtcttccc actggccccc    420
tgctgcgggg acacacccag ctcc                                           444

<210> SEQ ID NO 103
<211> LENGTH: 401
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 103
tctctggctc ccaggtgcca gatgtgccta tgatatgacc cagactccag cctctgtgga     60
ggtagctgtg ggaggcacag tcaccatcaa gtgccaggcc agtcagaaca ttggtagcta    120
cttatcctgg tatcagcaca aaccagggca gcgtcccaga ctcctgatgt acagggcatc    180
cactctggca tctggggtct catcgcggtt caaaggcagt ggatctggga cagagttcac    240
tctcaccatc agcggtgtgc agtgtgacaa tgctgccact tactactgtc aacagggtta    300
tactaatagt ggtgttgata atactttcgg cggagggacc gaggtggtgg tcaaaggtga    360
tccagttgca cctactgtcc tcatcttccc accatcagcg g                        401

<210> SEQ ID NO 104
<211> LENGTH: 69
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 104
atgaaggtaa caggcatctt tcttctcagt gccttggccc tgttgagtct atctggtaac     60
``` actggagct 69

<210> SEQ ID NO 105
<211> LENGTH: 237
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 105
atgaaggtaa caggcatctt tcttctcagt gccttggccc tgttgagtct atctggtaac      60
actggagctg actccctggg aagagaggcc aaatgttaca atgaacttaa tggatgcacc     120
aagatatatg accctgtctg tgggactgat ggaaatactt atcccaatga atgcgtgtta     180
tgttttgaaa tcggaaacg ccagacttct atcctcattc aaaaatctgg gccttgc        237

<210> SEQ ID NO 106
<211> LENGTH: 168
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 106
gactccctgg gaagagaggc caaatgttac aatgaactta atggatgcac caagatatat      60
gaccctgtct gtgggactga tggaaatact tatcccaatg aatgcgtgtt atgttttgaa     120
aatcggaaac gccagacttc tatcctcatt caaaaatctg ggccttgc                  168

<210> SEQ ID NO 107
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (2)..(2)
<223> OTHER INFORMATION: /replace="A"
<220> FEATURE:
<221> NAME/KEY: VARIANT
<222> LOCATION: (3)..(3)
<223> OTHER INFORMATION: /replace="N"
<220> FEATURE:
<221> NAME/KEY: VARIANT
<222> LOCATION: (4)..(4)
<223> OTHER INFORMATION: /replace="G" or "P" or "V"
<220> FEATURE:
<221> NAME/KEY: VARIANT
<222> LOCATION: (5)..(5)
<223> OTHER INFORMATION: /replace="V"
<220> FEATURE:
<221> NAME/KEY: SITE
<222> LOCATION: (1)..(6)
<223> OTHER INFORMATION: /note="Variant residues given in the sequence
      have no preference with respect to those in the annotations
      for variant positions"

<400> SEQUENCE: 107

Ser Ser Tyr Ala Ile Ser
1               5

<210> SEQ ID NO 108

```
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (3)..(4)
<223> OTHER INFORMATION: Any amino acid
<220> FEATURE:
<221> NAME/KEY: VARIANT
<222> LOCATION: (5)..(5)
<223> OTHER INFORMATION: /replace="G" or "Y"
<220> FEATURE:
<221> NAME/KEY: MOD_RES
<222> LOCATION: (7)..(9)
<223> OTHER INFORMATION: Any amino acid
<220> FEATURE:
<221> NAME/KEY: SITE
<222> LOCATION: (1)..(16)
<223> OTHER INFORMATION: /note="Variant residues given in the sequence
      have no preference with respect to those in the annotations
      for variant positions"

<400> SEQUENCE: 108

Xaa Ile Xaa Xaa Ser Gly Xaa Xaa Xaa Tyr Ala Ser Trp Ala Lys Ser
1               5                   10                  15

<210> SEQ ID NO 109
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(11)
<223> OTHER INFORMATION: Any amino acid

<400> SEQUENCE: 109

Arg Xaa Xaa Xaa Xaa Xaa Xaa Xaa Xaa Xaa Xaa
1               5                   10

<210> SEQ ID NO 110
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (4)..(4)
<223> OTHER INFORMATION: /replace="E"
<220> FEATURE:
<221> NAME/KEY: VARIANT
<222> LOCATION: (5)..(5)
<223> OTHER INFORMATION: /replace="G" or "D" or "N"
<220> FEATURE:
<221> NAME/KEY: VARIANT
<222> LOCATION: (7)..(7)
<223> OTHER INFORMATION: /replace="N" or "E" or "G"
<220> FEATURE:
<221> NAME/KEY: MOD_RES
<222> LOCATION: (8)..(8)
<223> OTHER INFORMATION: Any amino acid
```

```
<220> FEATURE:
<221> NAME/KEY: VARIANT
<222> LOCATION: (9)..(9)
<223> OTHER INFORMATION: /replace="A"
<220> FEATURE:
<221> NAME/KEY: MOD_RES
<222> LOCATION: (11)..(11)
<223> OTHER INFORMATION: Any amino acid
<220> FEATURE:
<221> NAME/KEY: SITE
<222> LOCATION: (1)..(11)
<223> OTHER INFORMATION: /note="Variant residues given in the sequence
      have no preference with respect to those in the annotations
      for variant positions"

<400> SEQUENCE: 110

Gln Ala Ser Gln Ser Ile Ser Xaa Tyr Leu Xaa
1               5                   10

<210> SEQ ID NO 111
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Any amino acid
<220> FEATURE:
<221> NAME/KEY: VARIANT
<222> LOCATION: (3)..(3)
<223> OTHER INFORMATION: /replace="T"
<220> FEATURE:
<221> NAME/KEY: VARIANT
<222> LOCATION: (4)..(4)
<223> OTHER INFORMATION: /replace="Y" or "K"
<220> FEATURE:
<221> NAME/KEY: VARIANT
<222> LOCATION: (6)..(6)
<223> OTHER INFORMATION: /replace="P" or "V"
<220> FEATURE:
<221> NAME/KEY: SITE
<222> LOCATION: (1)..(7)
<223> OTHER INFORMATION: /note="Variant residues given in the sequence
      have no preference with respect to those in the annotations
      for variant positions"

<400> SEQUENCE: 111

Xaa Ala Ser Thr Leu Ala Ser
1               5

<210> SEQ ID NO 112
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="H"
<220> FEATURE:
<221> NAME/KEY: VARIANT
<222> LOCATION: (3)..(3)
<223> OTHER INFORMATION: /replace="D"
<220> FEATURE:
<221> NAME/KEY: MOD_RES
<222> LOCATION: (5)..(6)
<223> OTHER INFORMATION: Any amino acid
<220> FEATURE:
```

```
<221> NAME/KEY: VARIANT
<222> LOCATION: (7)..(7)
<223> OTHER INFORMATION: /replace="N"
<220> FEATURE:
<221> NAME/KEY: VARIANT
<222> LOCATION: (8)..(8)
<223> OTHER INFORMATION: /replace="D" or "V" or "G"
<220> FEATURE:
<221> NAME/KEY: VARIANT
<222> LOCATION: (9)..(9)
<223> OTHER INFORMATION: /replace="D" or "I"
<220> FEATURE:
<221> NAME/KEY: VARIANT
<222> LOCATION: (10)..(10)
<223> OTHER INFORMATION: /replace="G" or "N"
<220> FEATURE:
<221> NAME/KEY: VARIANT
<222> LOCATION: (11)..(11)
<223> OTHER INFORMATION: /replace="V"
<220> FEATURE:
<221> NAME/KEY: MOD_RES
<222> LOCATION: (12)..(12)
<223> OTHER INFORMATION: Any amino acid
<220> FEATURE:
<221> NAME/KEY: SITE
<222> LOCATION: (1)..(12)
<223> OTHER INFORMATION: /note="Variant residues given in the sequence
     have no preference with respect to those in the annotations
     for variant positions"

<400> SEQUENCE: 112

Gln Gln Gly Tyr Xaa Xaa Ser Asn Val Asp Asn Xaa
1               5                   10

<210> SEQ ID NO 113
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic peptide"

<400> SEQUENCE: 113

Gly Gly Gly Gly Ser Gly Gly Gly Gly Ser Gly Gly Gly Gly Ser
1               5                   10                  15
```

ANTI-SERINE PROTEASE INHIBITOR KAZAL (SPIK) ANTIBODIES, IMMUNOCONJUGATES, AND METHODS OF USE

CROSS-REFERENCE TO RELATED APPLICATIONS

This application claims priority benefit of the filing date of U.S. Provisional Patent Application Ser. No. 62/871,565, filed on Jul. 8, 2019, the disclosure of which application is herein incorporated by reference in its entirety.

SEQUENCE LISTING

The instant application contains a Sequence Listing which has been submitted electronically in ASCII format and is hereby incorporated by reference in its entirety. Said ASCII copy, created on Sep. 15, 2020, is named IMC-0002-WO-_SL.txt and is 66,023 bytes in size.

GOVERNMENT RIGHTS

This invention was made with government support under grant number 2R44CA165314-02A1 and FAIN number R44CA165314 awarded by the National Institutes of Health (NIH) under the Small Business Innovation Research (SBIR) program. The government has certain rights in the invention.

FIELD OF THE INVENTION

Anti-AS-SPIK antibodies are disclosed, along with methods of making such antibodies, compositions, including pharmaceutical compositions, comprising such antibodies, and their use to diagnose and/or treat disorders characterized by the expression of AS-SPIK (e.g., liver cancer). Diagnostic methods and kits comprising the anti-AS-SPIK antibodies are also disclosed.

BACKGROUND

The liver is one of the largest organs in the body. The liver has many functions, including the production of enzymes and bile required for the digestion of food, regulation of glycogen storage, plasma protein synthesis, hormone production, and detoxification of various metabolites. Liver disorders include liver cancers, such as Hepatocellular Carcinoma (HCC) and intrahepatic Cholangiocarcinoma (ICC), viral infections, cirrhosis, and other inflammatory disorders of the liver, which affect millions of people worldwide. For example, over 5 million individuals in the U.S. and over 450 million individuals worldwide suffer from hepatitis B virus (HBV) and hepatitis C virus (HCV) infections, and over 30% of these infected individuals are at a high risk of developing liver cancer. Kew et al., *Pathologie-biologie* 2010; 58(4):273-277; Saraswat et al., *J Viral Hepat.* 2015; 22 Suppl 1:6-25; El-Serag et al., *Hepatology* 2014; 60(5): 1767-1775; Kanwal et al., *Clinical gastroenterology and hepatology* 2015; 13(4):805-807. Despite advances in diagnosis and treatment, liver cancer remains an important cause of both morbidity and mortality. El-Serag, *The New England journal of medicine* 2011; 365(12):1118-1127. Primary liver cancer, or cancer that originates in the liver, has a five-year survival rate of less than 10%. However, if liver cancer is detected early and during its most treatable stages, the survival rate increases to almost 40%. El-Serag et al., *Therapeutic advances in gastroenterology* 2011; 4(1):5-10. Patients with early-stage liver cancer may have few or no symptoms. Current detection methods, such as serological methods, ultrasound, computed tomography (CT) scans, magnetic resonance imaging (MRI), and angiography, can be unreliable due to low sensitivity and the potential for operator error. Imaging techniques, which are costly, may be less accurate for the detection of smaller, early stage tumors. Yu et al., *Clinical gastroenterology and hepatology* 2011; 9 (2):161-167; Bruix et al., *Hepatology* 2011; 53(3):1020-1022. Liver biopsy, which is still considered the most reliable method for distinguishing benign from malignant tumors, is invasive and requires surgery. Lok et al., *Gastroenterology* 2001; 122 (7):2092-2093. There is a continuing need for new methods of diagnosing and treating liver cancer, especially for those affected by liver cirrhosis, viral infections, and inflammatory disorders of the liver.

SUMMARY OF THE INVENTION

Aspects of the invention include an antibody, or antigen-binding fragment thereof, that specifically binds to AS-SPIK, wherein the antibody or antigen-binding fragment comprises: (a) a heavy chain variable region comprising: (i) a CDRH1 having two or fewer substitutions in any of the amino acid sequences of SEQ ID NOs: 21 to 30; and/or (ii) a CDRH2 having two or fewer substitutions in any of the amino acid sequences of SEQ ID NOs: 31 to 40; and/or (iii) a CDRH3 having two or fewer substitutions in any of the amino acid sequences of SEQ ID NOs: 41 to 50; and (b) a light chain variable region comprising: (i) a CDRL1 having two or fewer substitutions in any of the amino acid sequences of SEQ ID NOs: 51 to 60; and/or (ii) a CDRL2 having two or fewer substitutions in any of the amino acid sequences of SEQ ID NOs: 61 to 70; and/or (iii) a CDRL3 having two or fewer substitutions in any of the amino acid sequences of SEQ ID NOs: 71 to 80.

In some embodiments, the CDRH1, CDRH2, and CDRH3 sequences are present within a framework sequence, and wherein the CDRL1, CDRL2, and CDRL3 sequences are present within a framework sequence. In some embodiments, at least a portion of the framework sequence comprises a human consensus framework sequence.

In some embodiments, an antibody or antigen-binding fragment comprises: (a) a CDRH1 sequence selected from the group consisting of SEQ ID NOs: 21 to 30; and/or (b) a CDRH2 sequence selected from the group consisting of SEQ ID NOs: 31 to 40; and/or (c) a CDRH3 sequence selected from the group consisting of SEQ ID NOs: 41 to 50; and/or (d) a CDRL1 sequence selected from the group consisting of SEQ ID NOs: 51 to 60; and/or (e) a CDRL2 sequence selected from the group consisting of SEQ ID NOs: 61 to 70; and/or (f) a CDRL3 sequence selected from the group consisting of SEQ ID NOs: 71 to 80.

In some embodiments, an antibody or antigen-binding fragment comprises: (a) a CDRH1 sequence selected from the group consisting of SEQ ID NOs: 21 to 30; (b) a CDRH2 sequence selected from the group consisting of SEQ ID NOs: 31 to 40; (c) a CDRH3 sequence selected from the group consisting of SEQ ID NOs: 41 to 50; (d) a CDRL1 sequence selected from the group consisting of SEQ ID NOs: 51 to 60; (e) a CDRL2 sequence selected from the group consisting of SEQ ID NOs: 61 to 70; and (f) a CDRL3 sequence selected from the group consisting of SEQ ID NOs: 71 to 80.

In some embodiments, an antibody or antigen-binding fragment comprises: (a) a CDRH1 sequence of SEQ ID NO:

21, a CDRH2 sequence of SEQ ID NO: 31, a CDRH3 sequence of SEQ ID NO: 41, a CDRL1 sequence of SEQ ID NO: 51, a CDRL2 sequence of SEQ ID NO: 61, and a CDRL3 sequence of SEQ ID NO: 71; or (b) a CDRH1 sequence of SEQ ID NO: 22, a CDRH2 sequence of SEQ ID NO: 32, a CDRH3 sequence of SEQ ID NO: 42, a CDRL1 sequence of SEQ ID NO: 52, a CDRL2 sequence of SEQ ID NO: 62, and a CDRL3 sequence of SEQ ID NO: 72; or (c) a CDRH1 sequence of SEQ ID NO: 23, a CDRH2 sequence of SEQ ID NO: 33, a CDRH3 sequence of SEQ ID NO: 43, a CDRL1 sequence of SEQ ID NO: 53, a CDRL2 sequence of SEQ ID NO: 63, and a CDRL3 sequence of SEQ ID NO: 73; or (d) a CDRH1 sequence of SEQ ID NO: 24, a CDRH2 sequence of SEQ ID NO: 34, a CDRH3 sequence of SEQ ID NO: 44, a CDRL1 sequence of SEQ ID NO: 54, a CDRL2 sequence of SEQ ID NO: 64, and a CDRL3 sequence of SEQ ID NO: 74; or (e) a CDRH1 sequence of SEQ ID NO: 25, a CDRH2 sequence of SEQ ID NO: 35, a CDRH3 sequence of SEQ ID NO: 45, a CDRL1 sequence of SEQ ID NO: 55, a CDRL2 sequence of SEQ ID NO: 65, and a CDRL3 sequence of SEQ ID NO: 75; or (f) a CDRH1 sequence of SEQ ID NO: 26, a CDRH2 sequence of SEQ ID NO: 36, a CDRH3 sequence of SEQ ID NO: 46, a CDRL1 sequence of SEQ ID NO: 56, a CDRL2 sequence of SEQ ID NO: 66, and a CDRL3 sequence of SEQ ID NO: 76; or (g) a CDRH1 sequence of SEQ ID NO: 27, a CDRH2 sequence of SEQ ID NO: 37, a CDRH3 sequence of SEQ ID NO: 47, a CDRL1 sequence of SEQ ID NO: 57, a CDRL2 sequence of SEQ ID NO: 67, and a CDRL3 sequence of SEQ ID NO: 77; or (h) a CDRH1 sequence of SEQ ID NO: 28, a CDRH2 sequence of SEQ ID NO: 38, a CDRH3 sequence of SEQ ID NO: 48, a CDRL1 sequence of SEQ ID NO: 58, a CDRL2 sequence of SEQ ID NO: 68, and a CDRL3 sequence of SEQ ID NO: 78; or (i) a CDRH1 sequence of SEQ ID NO: 29, a CDRH2 sequence of SEQ ID NO: 39, a CDRH3 sequence of SEQ ID NO: 49, a CDRL1 sequence of SEQ ID NO: 59, a CDRL2 sequence of SEQ ID NO: 69, and a CDRL3 sequence of SEQ ID NO: 79; or (j) a CDRH1 sequence of SEQ ID NO: 30, a CDRH2 sequence of SEQ ID NO: 40, a CDRH3 sequence of SEQ ID NO: 50, a CDRL1 sequence of SEQ ID NO: 60, a CDRL2 sequence of SEQ ID NO: 70, and a CDRL3 sequence of SEQ ID NO: 80.

In some embodiments, an antibody or antigen-binding fragment comprises a heavy chain variable region having at least 95% sequence identity to any one of the sequences of SEQ ID NOs: 1 to 10 and/or a light chain variable region having at least 95% sequence identity to any one of the sequences of SEQ ID NOs: 11 to 20. In some embodiments, an antibody or antigen-binding fragment comprises a heavy chain variable region sequence selected from the group consisting of SEQ ID NOs: 1 to 10 and/or a light chain variable region sequence selected from the group consisting of SEQ ID NOs: 11 to 20. In some embodiments, an antibody or antigen-binding fragment comprises: (a) a heavy chain variable region sequence of SEQ ID NO: 1 and a light chain variable region sequence of SEQ ID NO: 11; or (b) a heavy chain variable region sequence of SEQ ID NO: 2 and a light chain variable region sequence of SEQ ID NO: 12; or (c) a heavy chain variable region sequence of SEQ ID NO: 3 and a light chain variable region sequence of SEQ ID NO: 13; or (d) a heavy chain variable region sequence of SEQ ID NO: 4 and a light chain variable region sequence of SEQ ID NO: 14; or (e) a heavy chain variable region sequence of SEQ ID NO: 5 and a light chain variable region sequence of SEQ ID NO: 15; or (f) a heavy chain variable region sequence of SEQ ID NO: 6 and a light chain variable region sequence of SEQ ID NO: 16; or (g) a heavy chain variable region sequence of SEQ ID NO: 7 and a light chain variable region sequence of SEQ ID NO: 17; or (h) a heavy chain variable region sequence of SEQ ID NO: 8 and a light chain variable region sequence of SEQ ID NO: 18; or (i) a heavy chain variable region sequence of SEQ ID NO: 9 and a light chain variable region sequence of SEQ ID NO: 19; or (j) a heavy chain variable region sequence of SEQ ID NO: 10 and a light chain variable region sequence of SEQ ID NO: 20.

Aspects of the invention include an isolated anti-AS-SPIK antibody, or an antigen-binding fragment thereof, that specifically binds to AS-SPIK, and does not bind to NS-SPIK, comprising: (a) a heavy chain variable region comprising CDRH1, CDRH2 and CDRH3 sequences in a human VH framework, wherein the CDRH sequences are a sequence having two or fewer substitutions in a CDR sequence selected from the group consisting of SEQ ID NOs: 21-50; and (b) a light chain variable region comprising CDRL1, CDRL2 and CDRL3 sequences in a human VL framework, wherein the CDRL sequences are a sequence having two or fewer substitutions in a CDR sequence selected from the group consisting of SEQ ID NOs: 51-80. In some embodiments, an antibody or antigen-binding fragment comprises: (a) a heavy chain variable region comprising CDRH1, CDRH2 and CDRH3 sequences in a human VH framework wherein the CDRH sequences are selected from the group consisting of SEQ ID NOs: 21 to 50; and (b) a light chain variable region comprising CDRL1, CDRL2 and CDRL3 sequences in a human VL framework, wherein the CDRL sequences are selected from the group consisting of SEQ ID NOs: 51 to 80.

Aspects of the invention include an isolated anti-AS-SPIK antibody, or an antigen-binding fragment thereof, that specifically binds to AS-SPIK, and does not bind to NS-SPIK, comprising: (a) a CDRH1 sequence of SEQ ID NO: 21, a CDRH2 sequence of SEQ ID NO: 31, and a CDRH3 sequence of SEQ ID NO: 41, in a human VH framework, and a CDRL1 sequence of SEQ ID NO: 51, a CDRL2 sequence of SEQ ID NO: 61, and a CDRL3 sequence of SEQ ID NO: 71, in a human VL framework; or (b) a CDRH1 sequence of SEQ ID NO: 22, a CDRH2 sequence of SEQ ID NO: 32, and a CDRH3 sequence of SEQ ID NO: 42, in a human VH framework, and a CDRL1 sequence of SEQ ID NO: 52, a CDRL2 sequence of SEQ ID NO: 62, and a CDRL3 sequence of SEQ ID NO: 72, in a human VL framework; or (c) a CDRH1 sequence of SEQ ID NO: 23, a CDRH2 sequence of SEQ ID NO: 33, and a CDRH3 sequence of SEQ ID NO: 43, in a human VH framework, and a CDRL1 sequence of SEQ ID NO: 53, a CDRL2 sequence of SEQ ID NO: 63, and a CDRL3 sequence of SEQ ID NO: 73, in a human VL framework; or (d) a CDRH1 sequence of SEQ ID NO: 24, a CDRH2 sequence of SEQ ID NO: 34, and a CDRH3 sequence of SEQ ID NO: 44, in a human VH framework, and a CDRL1 sequence of SEQ ID NO: 54, a CDRL2 sequence of SEQ ID NO: 64, and a CDRL3 sequence of SEQ ID NO: 74, in a human VL framework; or (e) a CDRH1 sequence of SEQ ID NO: 25, a CDRH2 sequence of SEQ ID NO: 35, and a CDRH3 sequence of SEQ ID NO: 45, in a human VH framework, and a CDRL1 sequence of SEQ ID NO: 55, a CDRL2 sequence of SEQ ID NO: 65, and a CDRL3 sequence of SEQ ID NO: 75, in a human VL framework; or (f) a CDRH1 sequence of SEQ ID NO: 26, a CDRH2 sequence of SEQ ID NO: 36, and a CDRH3 sequence of SEQ ID NO: 46, in a human VH framework, and a CDRL1 sequence of SEQ ID NO: 56, a CDRL2 sequence of SEQ ID NO: 66, and a CDRL3 sequence of SEQ ID NO: 76, in a human VL framework; or (g) a CDRH1 sequence of SEQ ID NO: 27, a CDRH2 sequence of SEQ ID NO: 37, and a CDRH3 sequence of SEQ ID NO: 47, in a human VH framework, and a CDRL1 sequence of SEQ ID NO: 57, a CDRL2 sequence of SEQ ID NO: 67, and a CDRL3 sequence of SEQ ID NO: 77, in a human VL framework; or (h) a CDRH1 sequence of SEQ ID NO: 28, a CDRH2 sequence of SEQ ID NO: 38, and a CDRH3 sequence of SEQ ID NO: 48, in a human VH framework, and a CDRL1 sequence of SEQ ID NO: 58, a CDRL2 sequence of SEQ ID NO: 68, and a CDRL3 sequence of SEQ ID NO: 78, in a human VL framework; or (i) a CDRH1 sequence of SEQ ID NO: 29, a CDRH2 sequence of SEQ ID NO: 39, and a CDRH3 sequence of SEQ ID NO: 49, in a human VH framework, and a CDRL1 sequence of SEQ ID NO: 59, a CDRL2 sequence of SEQ ID NO: 69, and a CDRL3 sequence of SEQ ID NO: 79, in a human VL framework; or (j) a CDRH1 sequence of SEQ ID NO: 30, a CDRH2 sequence of SEQ ID NO: 40, and a CDRH3 sequence of SEQ ID NO: 50, in a human VH framework, and a CDRL1 sequence of SEQ ID NO: 60, a CDRL2 sequence of SEQ ID NO: 70, and a CDRL3 sequence of SEQ ID NO: 80, in a human VL framework.

In some embodiments, an antibody or antigen-binding fragment is multi-specific. In some embodiments, an antibody or antigen-binding fragment is bispecific. In some embodiments, an antibody or antigen-binding fragment has binding affinity to an effector cell. In some embodiments, an antibody or antigen-binding fragment has binding affinity to a T-cell antigen. In some embodiments, an antibody or antigen-binding fragment has binding affinity to CD3.

In some embodiments, an antibody or antigen-binding fragment is monoclonal. In some embodiments, an antibody or antigen-binding fragment is in a CAR-T format.

Aspects of the invention include an immunoconjugate comprising an antibody as described herein, covalently attached to a cytotoxic agent. In some embodiments, the cytotoxic agent is selected from the group consisting of a toxin, a chemotherapeutic agent, a drug moiety, an antibiotic, a radioactive isotope and a nucleolytic enzyme.

Aspects of the invention include an immunoconjugate having the formula Ab-(L-D)p, wherein: (a) Ab is an antibody as described herein; (b) L is a linker; (c) D is a drug moiety; and (d) p is an integer that ranges from 1 to 8. In some embodiments, D is selected from the group consisting of: a maytansinoid, an auristatin and dolostatin. In some embodiments, L comprises one or more linkers selected from the group consisting of 6-maleimidocaproyl (MC), maleimidopropanoyl (MP), valine-citrulline (val-cit), alanine-phenylalanine (ala-phe), p-aminobenzyloxycarbonyl (PAB), N-Succinimidyl 4-(2-pyridylthio)pentanoate (SPP), N-succinimidyl 4-(N-maleimidomethyl)cyclohexane-1 carboxylate (SMCC), 4-(2-Pyridyldithio)butyric acid-N-hydroxysuccinimide ester (SPDB), and N-Succinimidyl (4-iodo-acetyl)aminobenzoate (SIAB).

Aspects of the invention include a pharmaceutical composition comprising an antibody, antigen-binding fragment, or immunoconjugate as described herein.

Aspects of the invention include a method for the treatment of a disorder characterized by expression of AS-SPIK, comprising administering to a subject with said disorder an antibody, antigen-binding fragment, or immunoconjugate as described herein, or a pharmaceutical composition as described herein.

Aspects of the invention include use of an antibody, antigen-binding fragment, or immunoconjugate as described herein, in the preparation of a medicament for the treatment of a disorder characterized by expression of AS-SPIK.

Aspects of the invention include an antibody, antigen-binding fragment, or immunoconjugate as described herein for use in the treatment of a disorder characterized by expression of AS-SPIK.

In some embodiments, the disorder is a liver disorder. In some embodiments, the liver disorder is hepatocellular carcinoma. In some embodiments, the liver disorder is intrahepatic cholangiocarcinoma. In some embodiments, the liver disorder is a viral infection. In some embodiments, the liver disorder is an inflammatory liver disorder. In some embodiments, the inflammatory liver disorder is cirrhosis of the liver.

Aspects of the invention include a polynucleotide encoding an antibody or antigen-binding fragment as described herein; a vector comprising the polynucleotide, or a host cell comprising the vector.

Aspects of the invention include a method of producing an antibody, antigen-binding fragment, or immunoconjugate as described herein, comprising growing a host cell as described herein under conditions permissive for expression of the antibody or antigen-binding fragment, and isolating the antibody or antigen-binding fragment from the cell.

Aspects of the invention include a diagnostic method for determining whether a subject has or is at risk of developing a disorder characterized by expression of AS-SPIK, the method comprising: (a) contacting a biological test sample from the subject with an AS-SPIK antibody or antigen-binding fragment as described herein to generate an AS-SPIK-antibody complex; (b) detecting a concentration of the AS-SPIK-antibody complex in the biological test sample; and (c) comparing the concentration of the AS-SPIK-antibody complex to a reference value to determine whether the subject has or is at risk of developing the disorder.

Aspects of the invention include a diagnostic method for determining whether a subject has or is at risk of developing a disorder characterized by expression of AS-SPIK, the method comprising: (a) contacting a biological test sample from the subject with a first antibody or antigen-binding fragment that specifically binds to SPIK to form a SPIK-antibody complex; (b) contacting the SPIK-antibody complex with an AS-SPIK antibody or antigen-binding fragment as described herein to generate an AS-SPIK-antibody complex; (c) detecting a concentration of the AS-SPIK-antibody complex in the biological test sample; and (d) comparing the concentration of the AS-SPIK-antibody complex to a reference value to determine whether the subject has or is at risk of developing the disorder.

In some embodiments, the antibody or antigen-binding fragment comprises a detectable label. In some embodiments, the disorder is a liver disorder. In some embodiments, the liver disorder is selected from the group consisting of: hepatocellular carcinoma, intrahepatic cholangiocarcinoma, viral infection of the liver, inflammatory disorder of the liver, and cirrhosis of the liver.

Aspects of the invention include a kit comprising an antibody, antigen-binding fragment, or immunoconjugate as described herein. In some embodiments, the kit further comprises an antibody or antigen-binding fragment that specifically binds to SPIK.

BRIEF DESCRIPTION OF THE DRAWINGS

FIG. 1 shows the results of an ELISA showing relative binding activity of various monoclonal antibodies to AS-SPIK and NS-SPIK.

FIG. 2 shows the results of detection of antibody-antigen complexes in samples with antibody IM-E2.

FIG. 3 provides an alignment of the VH regions of 10 antibodies: IM-A1, IM-A6, IM-B10, IM-C6, IM-D3, IM-D5, IM-E2, IM-F5, IM-G6 and IM-G7. The consensus sequence of all antibodies is listed. Antibodies as provided herein may be called by their long name that includes the letters "IM", such as IM-A1, IM-A6 and so on, or may be referred to in an abbreviated form by leaving the "IM" off, such as A1 or A6 and so on.

FIG. 4 provides an alignment of the VL regions of 10 antibodies A1, A6, B10, C6, D3, D5, E2, F5, G6 and G7. The consensus sequence of all antibodies is listed.

FIG. 5 provides an alignment of the VH CDRs of 10 antibodies A1, A6, B10, C6, D3, D5, E2, F5, D3 and D5. The consensus sequence of each CDR is listed.

FIG. 6 provides an alignment of VL CDRs of 10 antibodies A1, A6, B10, C6, D3, D5, E2, F5, G6 and G7. The consensus sequence of each CDR is listed.

FIG. 7 provides amino acid and nucleic acid sequence information.

DETAILED DESCRIPTION

The practice of the present invention will employ, unless otherwise indicated, conventional techniques of molecular biology (including recombinant techniques), microbiology, cell biology, biochemistry, and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., ed., 1994); "A Practical Guide to Molecular Cloning" (Perbal Bernard V., 1988); "Phage Display: A Laboratory Manual" (Barbas et al., 2001); Harlow, Lane and Harlow, Using Antibodies: A Laboratory Manual: Portable Protocol No. I, Cold Spring Harbor Laboratory (1998); and Harlow and Lane, Antibodies: A Laboratory Manual, Cold Spring Harbor Laboratory; (1988).

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the invention.

Unless indicated otherwise, antibody residues herein are numbered according to the Kabat numbering system (e.g., Kabat et al., Sequences of Immunological Interest. 5th Ed. Public Health Service, National Institutes of Health, Bethesda, Md. (1991)).

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

All references cited throughout the disclosure, including patent applications and publications, are incorporated by reference herein in their entirety.

Definitions

For purposes of interpreting this specification, the following definitions will apply and whenever appropriate, terms used in the singular will also include the plural and vice versa. In the event that any definition set forth conflicts with any document incorporated herein by reference, the definition set forth below shall control.

An "epitope" is the site on the surface of an antigen molecule to which a single antibody molecule binds. Generally, an antigen has several or many different epitopes and reacts with many different antibodies. The term specifically includes linear epitopes and conformational epitopes. The term includes any molecular determinant capable of specific binding to an antibody. In certain embodiments, an epitope determinant includes chemically active surface groupings of molecules such as amino acids, sugar side chains, phosphoryl, or sulfonyl, and, in certain embodiments, may have specific three dimensional structural characteristics, and/or specific charge characteristics. An epitope is a region of an antigen that is bound by an antibody. A "binding region" is a region on a binding target bound by a binding molecule.

"Epitope mapping" is the process of identifying the binding sites, or epitopes, of antibodies on their target antigens. Antibody epitopes may be linear epitopes or conformational epitopes. Linear epitopes are formed by a continuous sequence of amino acids in a protein. Conformational epitopes are formed of amino acids that are discontinuous in the protein sequence, but which are brought together upon folding of the protein into its three-dimensional structure.

"Epitope binning", as defined herein, is the process of grouping antibodies based on the epitopes they recognize. More particularly, epitope binning comprises methods and systems for discriminating the epitope recognition properties of different antibodies, combined with computational processes for clustering antibodies based on their epitope recognition properties and identifying antibodies having distinct binding specificities.

An antibody binds "essentially the same epitope" as a reference antibody when the two antibodies recognize identical or sterically overlapping epitopes. The most widely used and rapid methods for determining whether two epitopes bind to identical or sterically overlapping epitopes are competition assays, which can be configured in any number of different formats, using either labeled antigen or labeled antibody. Usually, the antigen is immobilized on a 96-well plate, and the ability of unlabeled antibodies to block the binding of labeled antibodies is measured using radioactive or enzyme labels.

A "modification" of an amino acid residue/position, as used herein, refers to a change of a primary amino acid sequence as compared to a starting amino acid sequence, wherein the change results from a sequence alteration involving said amino acid residue/positions. For example, typical modifications include substitution of the residue (or at said position) with another amino acid (e.g., a conservative or non-conservative substitution), insertion of one or more (generally fewer than 5 or 3) amino acids adjacent to said residue/position, and deletion of said residue/position. An "amino acid substitution" or variation thereof, refers to the replacement of an existing amino acid residue in a predetermined (starting) amino acid sequence with a different amino acid residue. Generally and preferably, a modification results in an alteration in at least one physical or biochemical activity of the variant polypeptide compared to a polypeptide comprising the starting (or "wild type") amino acid sequence. For example, in the case of an antibody, a physical or biochemical activity that is altered can be binding affinity, binding capability and/or binding effect upon a target molecule.

The term "antibody" includes monoclonal antibodies (including full length antibodies which have an immunoglobulin Fc region), single-chain molecules, as well as antibody fragments (e.g., Fab, F(ab')2, and Fv). The term "immunoglobulin" (Ig) is used interchangeably with "antibody" herein. The basic 4-chain antibody unit is a heterotetrameric glycoprotein composed of two identical light (L) chains and two identical heavy (H) chains. Unless noted otherwise, the term "antibody" is used herein in the broadest sense and specifically includes all isotypes, sub-classes and forms of antibodies, including IgG, IgM, IgA, IgD, and IgE antibodies and their fragments, preferably antigen-binding fragments.

Unless stated otherwise, the term "antibody" specifically includes native human and non-human IgG1, IgG2 (IgG2a, IgG2b), IgG3, IgG4, IgE, IgA, IgD and IgM antibodies, including naturally occurring variants.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) Nature 256:495, or may be made by recombinant DNA methods (see, e.g., U.S. Pat. No. 4,816,567). The "monoclonal antibodies" may also be isolated from phage antibody libraries using the techniques described in Clackson et al. (1991) Nature 352:624-628 and Marks et al. (1991) J. Mol. Biol. 222:581-597, for example.

The monoclonal antibodies herein specifically include "chimeric" antibodies (immunoglobulins) in which a portion of the heavy and/or light chain is identical with or homologous to corresponding sequences in antibodies derived from a particular species, while the remainder of the chain(s) is identical with or homologous to corresponding sequences in antibodies derived from another species, as well as fragments of such antibodies, so long as they exhibit the desired biological activity (U.S. Pat. No. 4,816,567; and Morrison et al. (1984) Proc. Natl. Acad. Sci. USA 81:6851-6855).

"Humanized" forms of non-human (e.g., murine) antibodies are antibodies which contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are also replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. For further details, see Jones et al. (1986) Nature 321:522-525; Riechmann et al. (1988) Nature 332:323-329; and Presta (1992) Curr. Op. Struct. Biol. 2:593-596.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2.

As used herein, the term "percent sequence homology" refers to the degree of homology between any given query sequence and a subject sequence. For example, a naturally occurring AS-SPIK polypeptide or NS-SPIK polypeptide can be the query sequence and a fragment of an AS-SPIK polypeptide or an NS-SPIK polypeptide can be the subject sequence. Similarly, a fragment of an AS-SPIK polypeptide or an NS-SPIK polypeptide can be the query sequence and a biologically active variant thereof can be the subject sequence.

The term "consensus sequence" as used herein means a sequence of amino acid or nucleotide residues that represent the most frequent residues found at each position in a sequence alignment, after aligning the sequences and introducing gaps, if necessary, to achieve the maximum sequence match, and not considering any conservative substitutions as part of the sequence identity.

An "isolated" antibody herein is one which has been identified and separated and/or recovered from a component of its natural environment in a recombinant host cell. Contaminant components of its natural environment are materials which would interfere with diagnostic or therapeutic uses for the antibody, and may include enzymes, hormones, and other proteinaceous or non-proteinaceous solutes, as well as undesired byproducts of the production. In a preferred embodiment, an isolated antibody herein will be purified (1) to greater than 95% by weight, or greater than 98% by weight, or greater than 99% by weight, as determined by SDS-PAGE or SEC-HPLC methods, (2) to a degree sufficient to obtain at least 15 residues of N-terminal or internal amino acid sequence by use of an amino acid sequencer, or (3) to homogeneity by SDS-PAGE under reducing or non-reducing conditions using Coomassie blue or, preferably, silver stain. Ordinarily, an isolated antibody will be prepared by at least one purification step.

In the case of IgGs, the 4-chain unit is generally about 150,000 Daltons. Each L chain is linked to an H chain by one covalent disulfide bond, while the two H chains are linked to each other by one or more disulfide bonds depending on the H chain isotype. Each H and L chain also has regularly spaced intra-chain disulfide bridges. Each H chain has at the N-terminus, a variable domain (VH) followed by three constant domains (CH) for each of the α and γ chains and four CH domains for μ and ε isotypes. Each L chain has at the N-terminus, a variable domain (VL) followed by a constant domain at its other end. The VL is aligned with the VH and the CL is aligned with the first constant domain of the heavy chain (CH1). Particular amino acid residues are believed to form an interface between the light chain and heavy chain variable domains. The pairing of a VH and VL together forms a single antigen-binding site.

The term "polypeptide" is used herein in the broadest sense and includes peptide sequences. The term "peptide" generally describes linear molecular chains of amino acids containing up to about 60, preferably up to about 30 amino acids covalently linked by peptide bonds.

The term "specific binding" or "specifically binds to" or is "specific for" refers to the binding of an antibody to a target antigen, e.g., an epitope on a particular polypeptide, peptide, or other target (e.g., a glycoprotein target), and means binding that is measurably different from a non-specific interaction (e.g., a non-specific interaction may be binding to bovine serum albumin or casein). Specific binding can be measured, for example, by determining binding of an antibody to a target molecule compared to binding to a control molecule. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a Kd for the target of at least about 200 nM, alternatively at least about 150 nM, alternatively at least about 100 nM, alternatively at least about 60 nM, alternatively at least about 50 nM, alternatively at least about 40 nM, alternatively at least about 30 nM, alternatively at least about 20 nM, alternatively at least about 10 nM, alternatively at least about 8 nM, alternatively at least about 6 nM, alternatively at least about 4 nM, alternatively at least about 2 nM, alternatively at least about 1 nM, or greater. In certain instances, the term "specific binding" refers to binding where a molecule binds to a particular polypeptide or epitope on a particular polypeptide without substantially binding to any other polypeptide or polypeptide epitope.

"Binding affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). For example, the Kd can be about 200 nM, 150 nM, 100 nM, 60 nM, 50 nM, 40 nM, 30 nM, 20 nM, 10 nM, 8 nM, 6 nM, 4 nM, 2 nM, 1 nM, or stronger. Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art.

As used herein, the "Kd" or "Kd value" refers to a dissociation constant measured by a technique appropriate for the antibody and target pair, for example using surface plasmon resonance assays, for example, using a BIAcore™-2000 or a BIAcore™-3000 (BIAcore, Inc., Piscataway, N.J.) at 25° C. with immobilized antigen CM5 chips at about 10 response units (RU).

The term "valent" as used herein denotes the presence of a specified number of binding sites in an antibody. As such, the term "bivalent" denotes the presence of two binding sites.

"Polyepitopic specificity" refers to the ability to specifically bind to two or more different epitopes on the same or different target(s). "Monospecific" refers to the ability to bind only one epitope. In some embodiments, an antibody binds to each epitope with an affinity of at least 10−7 M, or 10−8 M or better.

The term "target" or "binding target" is used in the broadest sense and specifically includes, without limitation, polypeptides, nucleic acids, carbohydrates, lipids, cells, and other molecules with or without biological function as they exist in nature.

The term "antigen" refers to an entity or fragment thereof, which can bind to an antibody or trigger a cellular immune response. An immunogen refers to an antigen, which can elicit an immune response in an organism, particularly an animal, more particularly a mammal including a human. The term antigen includes regions known as antigenic determinants or epitopes, as defined above.

As used herein, the term "immunogenic" refers to substances that elicit the production of antibodies, and/or activate T-cells and/or other reactive immune cells directed against an antigen of the immunogen.

An "antigen-binding site" or "antigen-binding region" of an antibody of the present invention typically contains six hypervariable regions (HVRs) which contribute in varying degrees to the affinity of the binding site for antigen. The term "complementarity determining region" or "CDR" is used interchangeably herein with the term "hypervariable region" or "HVR". There are three heavy chain variable domain HVRs (HVR-H1, HVR-H2 and HVR-H3) and three light chain variable domain HVRs (HVR-L1, HVR-L2 and HVR-L3). The extent of HVR and framework regions (FRs) is determined by comparison to a compiled database of amino acid sequences in which those regions have been defined according to variability among the sequences and/or structural information from antibody/antigen complexes. Also included within the scope of the invention are functional antigen binding sites comprised of fewer HVRs (i.e., where binding specificity is determined by three, four or five HVRs). Less than a complete set of 6 HVRs may be sufficient for binding to some binding targets. Thus, in some instances, the HVRs of a VH or a VL domain alone will be sufficient. Furthermore, certain antibodies might have non-HVR-associated binding sites for an antigen. Such binding sites are specifically included within the present definition.

A "naked antibody" for the purposes herein is an antibody that is not conjugated to a cytotoxic moiety or radiolabel.

An "antibody-drug conjugate" (ADC) or immunoconjugate means an antibody, or antigen-binding fragment thereof, conjugated to a cytotoxic agent, such as a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate).

The term "host cell" as used herein denotes any kind of cellular system which can be engineered to generate the antibodies according to the current invention. In one embodiment, Chinese hamster ovary (CHO) cells are used as host cells.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Variant progeny that have the same function or biological activity as screened for in the originally transformed cell are included.

A nucleic acid is "operably linked" when it is placed in a functional relationship with another nucleic acid sequence. For example, DNA for a pre-sequence or secretory leader is operably linked to DNA for a polypeptide if it is expressed as a pre-protein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors or linkers are used in accordance with conventional practice.

The terms "anti-AS-SPIK antibody", "AS-SPIK antibody", or "an antibody that binds to AS-SPIK" all refer to an antibody that is capable of binding AS-SPIK with sufficient affinity such that the antibody is useful as a diagnostic and/or therapeutic agent in targeting AS-SPIK.

In one embodiment, an "AS-SPIK antibody" is used herein to specifically refer to an anti-AS-SPIK monoclonal antibody that (i) comprises a heavy chain variable domain sequence as provided in any one of SEQ ID NOs: 1-10 and/or a light chain variable domain sequence as provided in any one of SEQ ID NOs: 11-20; or (ii) comprises one, two, three, four, five, or six of the CDRs provided in SEQ ID NOS: 21-80.

The term "variable" refers to the fact that certain segments of the variable domains differ extensively in sequence among antibodies. The "variable" or "V" domain mediates antigen binding and defines specificity of a particular antibody for its particular antigen. However, the variability is not evenly distributed across the 110-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, MD (1991)).

An "intact" antibody is one which comprises an antigen-binding site as well as a light chain constant domain (CL) and at least heavy chain constant domains of the particular antibody class. For example, an intact IgG antibody comprises an antigen-binding site, a light chain constant domain CL, and at least heavy chain constant domains CH1 (Cγ1), CH2 (Cγ2) and CH3 (Cγ3). An intact IgM antibody comprises an antigen-binding site, a light chain constant domain CL, and at least heavy chain constant domains CM1 (Cμ1), CM2 (Cμ2), CM3 (Cμ3) and CM4 (Cμ4). An intact IgA antibody comprises an antigen-binding site, a light chain constant domain CL, and at least heavy chain constant domains CA1 (Cα1), CA2 (Cα2) and CA3 (Cα3). An intact IgD antibody comprises an antigen-binding site, a light chain constant domain CL, and at least heavy chain constant domains CD1 (Cδ1), CD2 (Cδ2) and CD3 (Cδ3). An intact IgE antibody comprises an antigen-binding site, a light chain constant domain CL, and at least heavy chain constant domains CE1 (Cε1), CE2 (Cε2), CE3 (Cε3) and CE4 (Cε4). The constant domains can be native sequence constant domains (e.g., human native sequence constant domains) or amino acid sequence variants thereof. Preferably, an intact antibody has one or more effector functions.

"Antibody fragments" or "antigen-binding fragments" of antibodies comprise a portion of an intact antibody, preferably the antigen binding or variable region, of the intact antibody. Non-limiting examples of antibody fragments include Fab, Fab', F(ab')2, and Fv fragments; diabodies; linear antibodies (see U.S. Pat. No. 5,641,870, Example 2; Zapata et al., Protein Eng. 8(10): 1057-1062 (1995)); single-chain antibody molecules; and multi-specific antibodies formed from antibody fragments. In one embodiment, an antibody fragment comprises an antigen binding site of an intact antibody and thus retains the ability to bind antigen. Those of ordinary skill in the art will understand that an antibody fragment can be generated from any intact antibody, e.g., from an IgG, IgM, IgA, IgD, or IgE antibody, by separating at least an antigen-binding portion of the antibody from the remainder of its light and heavy chains to create an antigen-binding fragment. In certain embodiments, an antibody fragment can comprise an antigen-binding region of an antibody, as well as one or more additional domains of a light and/or heavy chain of the antibody. For example, in some embodiments, an antibody fragment can comprise an antigen-binding region comprising a VH and a VL domain, a light chain constant domain CL, and one or more heavy chain constant domains, e.g., a CH1 (Cγ1) domain, a CM1 (Cμ1) domain, a CA1 (Cα1) domain, a CD1 (Cδ1) domain, or a CE1 (Cε1) domain.

In the case of IgG antibody fragments, papain digestion produces two identical antigen-binding fragments, called "Fab" fragments, and a residual "Fc" fragment, a designation reflecting the ability to crystallize readily. The Fab fragment consists of an entire L chain along with the variable region domain of the H chain (VH), and the first constant domain of one heavy chain (CH1). Each Fab fragment is monovalent with respect to antigen binding, i.e., it has a single antigen-binding site. Pepsin treatment of an IgG antibody yields a single large F(ab')2 fragment which roughly corresponds to two disulfide linked Fab fragments having divalent antigen-binding activity and is still capable of cross-linking antigen. Fab' fragments differ from Fab fragments by having additional few residues at the carboxy terminus of the CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

The Fc fragment of an IgG antibody comprises the carboxy-terminal portions of both H chains held together by disulfides. The effector functions of antibodies are determined by sequences in the Fc region, which region is also the part recognized by Fc receptors (FcR) found on certain types of cells.

A "native-sequence Fc region" comprises an amino acid sequence identical to the amino acid sequence of an Fc region found in nature. Native-sequence human Fc regions include, for example, a native-sequence human IgG1 Fc region (non-A and A allotypes); native-sequence human IgG2 Fc region; native-sequence human IgG3 Fc region; and native-sequence human IgG4 Fc region, as well as naturally occurring variants thereof.

A "variant Fc region" comprises an amino acid sequence that differs from that of a native-sequence Fc region by virtue of at least one amino acid modification, preferably one or more amino acid substitution(s). Preferably, a variant Fc region has at least one amino acid substitution compared to a native-sequence Fc region or to the Fc region of a parent polypeptide, e.g., from about one to about ten amino acid substitutions, and preferably from about one to about five amino acid substitutions in a native-sequence Fc region or in the Fc region of the parent polypeptide. A variant Fc region herein will preferably possess at least about 80% homology with a native-sequence Fc region and/or with an Fc region of a parent polypeptide, and most preferably at least about 90% homology therewith, more preferably at least about 95% homology therewith.

The human IgG1 amino acid sequence is provided by UniProtKB No. P01857, which is incorporated by reference herein in its entirety. The human IgG2 amino acid sequence is provided by UniProtKB No. P01859, which is incorporated by reference herein in its entirety. The human IgG3 amino acid sequence is provided by UniProtKB No. P01860, which is incorporated by reference herein in its entirety. The human IgG4 amino acid sequence is provided by UniProtKB No. P01861, which is incorporated by reference herein in its entirety.

"Fv" is the minimum antibody fragment which contains a complete antigen-recognition and binding site. This fragment consists of a dimer of one heavy- and one light-chain variable region domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three HVRs specific for an antigen) has the ability to recognize and bind antigen, although at a lower affinity than the entire binding site.

"Single-chain Fv" also abbreviated as "sFv" or "scFv" are antibody fragments that comprise the VH and VL antibody domains connected into a single polypeptide chain. Preferably, the sFv polypeptide further comprises a polypeptide linker between the VH and VL domains which enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994); Borrebaeck 1995, infra.

The term "chimeric antigen receptor" or "CAR" is used herein in the broadest sense to refer to an engineered receptor, which grafts a desired binding specificity (e.g., the antigen-binding region of a monoclonal antibody or other ligand) to membrane-spanning and intracellular-signaling domains. Typically, the receptor is used to graft the specificity of a monoclonal antibody onto a T cell to create a chimeric antigen receptor (CAR). (Dai et al., J Natl Cancer Inst, 2016; 108(7):djv439; and Jackson et al., Nature Reviews Clinical Oncology, 2016; 13:370-383).

As used herein, the term "effector cell" refers to an immune cell which is involved in the effector phase of an immune response, as opposed to the cognitive and activation phases of an immune response. Some effector cells express specific Fc receptors and carry out specific immune functions. In some embodiments, an effector cell such as a natural killer cell is capable of inducing antibody-dependent cellular cytotoxicity (ADCC). For example, monocytes and macrophages, which express FcR, are involved in specific killing of target cells and presenting antigens to other components of the immune system, or binding to cells that present antigens. In some embodiments, an effector cell may phagocytose a target antigen or target cell.

"Human effector cells" are leukocytes which express receptors such as T cell receptors or FcRs and perform effector functions. Preferably, the cells express at least FcγRIII and perform ADCC effector function. Examples of human leukocytes which mediate ADCC include natural killer (NK) cells, monocytes, cytotoxic T cells and neutrophils; with NK cells being preferred. The effector cells may be isolated from a native source thereof, e.g., from blood or PBMCs as described herein.

The term "immune cell" is used herein in the broadest sense, including, without limitation, cells of myeloid or lymphoid origin, for instance lymphocytes (such as B cells and T cells including cytolytic T cells (CTLs)), killer cells, natural killer (NK) cells, macrophages, monocytes, eosinophils, polymorphonuclear cells, such as neutrophils, granulocytes, mast cells, and basophils.

Antibody "effector functions" refer to those biological activities attributable to the Fc region (a native sequence Fc region or amino acid sequence variant Fc region) of an antibody. Examples of antibody effector functions include C1q binding; complement dependent cytotoxicity; Fc receptor binding; antibody-dependent cell-mediated cytotoxicity (ADCC); phagocytosis; down regulation of cell surface receptors (e.g., B cell receptor; BCR), etc.

"Antibody-dependent cell-mediated cytotoxicity" and "ADCC" refer to a cell-mediated reaction in which nonspecific cytotoxic cells that express Fc receptors (FcRs) (e.g., Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Annu. Rev. Immunol 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. PNAS (USA) 95:652-656 (1998).

"Complement dependent cytotoxicity" or "CDC" refers to the ability of a molecule to lyse a target in the presence of complement. The complement activation pathway is initiated by the binding of the first component of the complement system (C1q) to a molecule (e.g., an antibody) complexed with a cognate antigen. To assess complement activation, a CDC assay, e.g., as described in Gazzano-Santoro et al., J. Immunol. Methods 202:163 (1996), may be performed.

A "blocking" antibody or an "antagonist" or "antagonistic" antibody is one which inhibits or reduces a biological activity of an antigen to which it binds. Preferred blocking antibodies or antagonist antibodies are capable of substantially or completely inhibiting a biological activity of an antigen.

An antibody "which binds" an antigen of interest, e.g., an AS-SPIK or NS-SPIK polypeptide, is one that binds the antigen with sufficient affinity such that the antibody is useful as a therapeutic agent in targeting a cell or tissue expressing the antigen, and does not significantly cross-react with other proteins. With regard to the binding of an antibody to a target molecule, the term "specific binding" or "specifically binds to" or is "specific for" a particular polypeptide or an epitope on a particular polypeptide target means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labeled target. In this case, specific binding is indicated if the binding of the labeled target to a probe is competitively inhibited by excess unlabeled target. In one embodiment, the term "specific binding" refers to binding where a molecule binds to a particular polypeptide or epitope on a particular polypeptide without substantially binding to any other polypeptide or polypeptide epitope.

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), skin cancer, melanoma, lung cancer, including small-cell lung cancer, non-small cell lung cancer ("NSCLC"), adenocarcinoma of the lung and squamous carcinoma of the lung, cancer of the peritoneum, gastric or stomach cancer including gastrointestinal cancer, pancreatic cancer (e.g., pancreatic ductal adenocarcinoma), glioblastoma, cervical cancer, ovarian cancer (e.g., high grade serous ovarian carcinoma), liver cancer (e.g., hepatocellular carcinoma (HCC), intrahepatic cholangiocarcinoma (ICC)), bladder cancer (e.g., urothelial bladder cancer), testicular (germ cell tumor) cancer, hepatoma, breast cancer, brain cancer (e.g., astrocytoma), colon cancer, rectal cancer, colorectal cancer, endometrial or uterine carcinoma, salivary gland carcinoma, kidney or renal cancer (e.g., renal cell carcinoma, nephroblastoma or Wilms' tumour), prostate cancer, vulval cancer, thyroid cancer, hepatic carcinoma, anal carcinoma, penile carcinoma, as well as head and neck cancer. Additional examples of cancer include, without limitation, retinoblastoma, thecomas, arrhenoblastomas, hepatoma, hematologic malignancies including non-Hodgkin's lymphoma (NHL), multiple myeloma and acute hematologic malignancies, endometrial or uterine carcinoma, endometriosis, fibrosarcomas, choriocarcinoma, salivary gland carcinoma, vulval cancer, thyroid cancer, esophageal carcinomas, hepatic carcinoma, anal carcinoma, penile carcinoma, nasopharyngeal carcinoma, laryngeal carcinomas, Kaposi's sarcoma, melanoma, skin carcinomas, Schwannoma, oligodendroglioma, neuroblastomas, rhabdomyosarcoma, osteogenic sarcoma, leiomyosarcomas, and urinary tract carcinomas.

The term "metastatic cancer" means the state of cancer where the cancer cells of a tissue of origin are transmitted from the original site to one or more sites elsewhere in the body, by the blood vessels or lymphatics, to form one or more secondary tumors in one or more organs besides the tissue of origin.

As used herein, an "AS-SPIK-associated disorder" of a "disorder that is characterized by expression of AS-SPIK" is a disorder that is associated with expression or over-expression of an AS-SPIK gene or gene product (an AS-SPIK polypeptide), which can be any disorder that is characterized by cells that express normal or elevated levels of AS-SPIK, relative to suitable control cells. Suitable control cells can be cells from an individual who is not affected with an AS-SPIK-expressing or over-expressing cancer, or they may be non-cancerous cells from either the subject in need, or they may be non-cancerous cells from another individual who is affected with an AS-SPIK-expressing or over-expressing cancer. One prominent example of an AS-SPIK-associated disorder is liver cancer.

The terms "cell proliferative disorder" and "proliferative disorder" refer to disorders that are associated with some degree of abnormal cell proliferation. In one embodiment, the cell proliferative disorder is cancer.

"Tumor", as used herein, refers to all neoplastic cell growth and proliferation, whether malignant or benign, and all pre-cancerous and cancerous cells and tissues.

The terms "predictive" and "prognostic" as used herein are also interchangeable, in the sense of meaning that the methods for prediction or prognostication are to allow the person practicing the method to select patients that are deemed (usually in advance of treatment, but not necessarily) more likely to respond to treatment with an anti-cancer agent, including an anti-AS-SPIK antibody.

The terms "treat", "treatment" or "treating" as used herein refer to both therapeutic treatment and prophylactic of preventative measures, wherein the object is to prevent or slow down (lessen) a targeted pathological condition or disorder. A subject in need of treatment includes those already having a particular condition or disorder, as well as those prone to having the disorder or those in whom the disorder is to be prevented.

DETAILED DESCRIPTION OF THE INVENTION

The present invention is based, at least in part, on the discovery that certain disorders are characterized by expression of a unique form or serine protease inhibitor Kazal (SPIK). Once prominent example is liver cancer, which includes, without limitation, hepatocellular carcinoma (HCC) and intrahepatic cholangiocarcinoma (ICC). More specifically, the inventors have found that certain cancers, such as liver cancer, express a form of SPIK that includes an additional 23 amino acids at the N-terminus of the secreted SPIK polypeptide. This 23 amino acid segment (SEQ ID NO: 81) is not found in the SPIK polypeptide secreted from normal cells, such as pancreatic cells. This is consistent with our previous report that the first 9 amino acids of this 23 amino acid segment may exist in unprocessed SPIK secreted by a liver cancer cell line. Lu et al., Immunology 2011; 134(4):398-408. We may refer to the longer form of SPIK as AS-SPIK or Abnormal Secreted SPIK. We may also refer to AS-SPIK produced by liver cancer cells as LC-SPIK or Liver Cancer Secreted SPIK. The terms AS-SPIK and LC-SPIK are used interchangeably herein. An exemplary AS-SPIK polypeptide can have the amino acid sequence of SEQ ID NO: 82. We may refer to the form of SPIK secreted by normal cells, such as pancreas cells, as NS-SPIK or Normal Secreted SPIK. An exemplary NS-SPIK polypeptide can have the amino acid sequence of SEQ ID NO: 83. We have also found that the conformation (e.g., 3D structure) of AS-SPIK differs from that of NS-SPIK.

Accordingly, aspects of the invention include compositions, such as antibodies, that specifically or preferentially bind to AS-SPIK, and that do not bind to NS-SPIK. Also provided are AS-SPIK complexes. AS-SPIK complexes in accordance with embodiments of the invention comprise an antibody that specifically or preferentially binds to AS-SPIK, and an AS-SPIK polypeptide, or fragment thereof.

Aspects of the invention include antibody-drug conjugates (ADCs) that comprise an antibody as described herein (Ab), a linker (L), and a drug moiety (D). In some embodiments, an ADC has the formula Ab-(L-D)p, where p is an integer that ranges from 1 to 8.

Aspects of the invention also include methods of using the subject antibodies for the detection of a disorder characterized by expression of AS-SPIK, e.g., a liver disorder, such as a liver cancer, for example, HCC or ICC.

While we believe we understand certain events that occur during the expression of AS-SPIK, the compositions and methods of the present invention are not limited to those that work by affecting any particular cellular mechanism. Without being held to theory, the inventors hypothesize that because SPIK is a protease inhibitor, over-expression of SPIK in cancer cells suppresses the activity of signal peptide peptidase, one kind of protease, resulting in un-attenuated, full-length protein being secreted from cancer cells.

Compositions

The compositions provided herein include antibodies that specifically or preferentially bind to AS-SPIK and that do not bind to NS-SPIK.

Serine protease inhibitor Kazal (SPIK), also known as SPINK1, PSTI, and TATI, is a small protein that has been shown to broadly regulate the activity of many cellular proteases, such as trypsin-like proteases and chymotrypsin-like proteases. Greene, LJ, J Surg Oncol. 1975; 7(2):151-154; Horii et al., Biochemical and biophysical research communications 1987; 149(2):635-641; Stenman, UH, Clin Chem. 2002; 48(8):1206-1209. SPIK may also play a role in inhibition of apoptosis. Lu et al., Immunology 2011; 134 (4):398-408. Exemplary human SPIK amino acid sequences include GenBank Accession Number: M11949, GI Number: 190687; GenBank Accession Number: NM003122, GI: 657940887; and GeneBank Accession Number: BC025790, GI: 19343607.

Antibodies

The antibodies provided herein can include an antibody that specifically or preferentially binds to an epitope within amino acids 1-23 of SEQ ID NO: 82, or an epitope containing at least one amino-acid within this region. The epitope can be a conformational epitope (conformation-specific epitope) or a linear epitope. In some embodiments, an antibody specifically or preferentially binds to an epitope in the AS-SPIK protein sequence shown in SEQ ID NO: 81. In some embodiments, an antibody specifically or preferentially binds to a conformation-specific epitope comprising at least one amino acid of SEQ ID NO: 81.

Antibodies in accordance with embodiments of the invention may be polyclonal or monoclonal, particularly monoclonal, and may be produced by human, mouse, rabbit, sheep or goat cells, or by hybridomas derived from these cells. In some embodiments, an antibody can be humanized, or chimeric.

Antibodies in accordance with embodiments of the invention can assume various configurations and encompass proteins consisting of one or more polypeptides substantially encoded by immunoglobulin genes. Any one of a variety of antibody structures can be used, including the intact antibody, antibody multimers, or antibody fragments or other variants thereof that include functional, antigen-binding regions of the antibody. The term "immunoglobulin" may be used synonymously with "antibody." The antibodies may be monoclonal or polyclonal in origin. Regardless of the source of the antibody, suitable antibodies include intact antibodies, for example, IgG tetramers having two heavy (H) chains and two light (L) chains, single chain antibodies, chimeric antibodies, humanized antibodies, complementary determining region (CDR)-grafted antibodies as well as antibody fragments, e.g., Fab, Fab', F(ab')2, scFv, Fv, and recombinant antibodies derived from such fragments, e.g., camelbodies, microantibodies, diabodies and bispecific antibodies.

An intact antibody is one that comprises an antigen-binding variable region (VH and VL) as well as a light chain constant domain (CL) and heavy chain constant domains, CH1, CH2 and CH3. The constant domains may be native sequence constant domains (e.g. human native sequence constant domains) or amino acid sequence variants thereof. As is well known in the art, the VH and VL regions are further subdivided into regions of hypervariability, termed "complementarity determining regions" (CDRs), interspersed with the more conserved framework regions (FRs). The CDR of an antibody typically includes amino acid sequences that together define the binding affinity and specificity of the natural Fv region of a native immunoglobulin binding site.

An anti-AS-SPIK antibody can be from any class of immunoglobulin, for example, IgA, IgG, IgE, IgD, IgM (as well as subtypes thereof (e.g., IgG1, IgG2, IgG3, and IgG4)), and the light chains of the immunoglobulin may be of types kappa or lambda. The recognized human immunoglobulin genes include the kappa, lambda, alpha (IgA1 and IgA2), gamma (IgG1, IgG2, IgG3, IgG4), delta, epsilon, and mu constant region genes, as well as the myriad immunoglobulin variable region genes.

The term "antigen-binding portion" of an immunoglobulin or antibody refers generally to a portion of an immunoglobulin that specifically or preferentially binds to a target, in this case, an epitope comprising amino acid residues on AS-SPIK (SEQ ID NO:81), but not NS-SPIK. An antigen-binding portion of an immunoglobulin is therefore a molecule in which one or more immunoglobulin chains are not full length, but which specifically or preferentially binds to a cellular target. Examples of antigen-binding portions or fragments include: (i) an Fab fragment, a monovalent fragment consisting of the VLC, VHC, CL and CH1 domains; (ii) a F(ab')2 fragment, a bivalent fragment comprising two Fab fragments linked by a disulfide bridge at the hinge region; (iii) a Fv fragment consisting of the VLC and VHC domains of a single arm of an antibody, and (v) an isolated CDR having sufficient framework to specifically or preferentially bind, e.g., an antigen binding portion of a variable region. An antigen-binding portion of a light chain variable region and an antigen binding portion of a heavy chain variable region, e.g., the two domains of the Fv fragment, VLC and VHC, can be joined, using recombinant methods, by a synthetic linker that enables them to be made as a single protein chain in which the VLC and VHC regions pair to form monovalent molecules (known as single chain Fv (scFv). Such scFvs are encompassed by the term "antigen-binding portion" of an antibody.

An "Fv" fragment is the minimum antibody fragment that contains a complete antigen-recognition and binding site. This region consists of a dimer of one heavy chain and one light chain variable domain in tight, con-covalent association. It is in this configuration that three hypervariable regions of each variable domain interact to define an antigen-binding site on the surface of the VH-VL dimer. While six hypervariable regions confer antigen-binding specificity, even a single variable domain (or half of an Fv comprising only three hypervariable regions specific for an antigen) has the ability to recognize and bind antigen, although at a lower affinity than the entire binding site. To improve stability, the VH-VL domains may be connected by a flexible peptide linker such as (Gly4Ser)3 (SEQ ID NO: 113) to form a single chain Fv or scFV antibody fragment or may be engineered to form a disulfide bond by introducing two cysteine residues in the framework regions to yield a disulfide stabilized Fv (dsFv).

Fragments of antibodies are suitable for use in the methods provided so long as they retain the desired specificity of the full-length antibody and/or sufficient specificity to bind AS-SPIK and not NS-SPIK.

The antigen-binding domains of the antibodies described herein can be utilized in the production of T-cell engager molecules (e.g., bispecific T-cell engagers, aka BiTE molecules) as well as CAR-T structures. T-cell engager molecules are described, for example, in Huehls et al., Bispecific T cell engagers for cancer immunotherapy, Immunol Cell Biol. 2015 March; 93(3):290-296. CAR-T structures comprising single-domain antibodies as a binding (targeting) domain are described, for example, in Iri-Sofia et al., 2011, Experimental Cell Research 317:2630-2641 and Jamnani et al., 2014, Biochim Biophys Acta, 1840:378-386.

Methods for preparing antibody fragments encompass both biochemical methods (e.g. proteolytic digestion of intact antibodies which may be followed by chemical cross-linking) and recombinant DNA-based methods in which immunoglobulin sequences are genetically engineered to direct the synthesis of the desired fragments. Antibody fragments can be obtained by proteolysis of the whole immunoglobulin by the non-specific thiolprotease, papain. Papain digestion yields two identical antigen-binding fragments, termed "Fab fragments," each with a single antigen-binding site, and a residual "Fc fragment." The various fractions can be separated by protein A-Sepharose or ion exchange chromatography. The usual procedure for preparation of F(ab')2 fragments from IgG of rabbit and human origin is limited proteolysis by the enzyme pepsin. Pepsin treatment of intact antibodies yields an F(ab')2 fragment that has two antigen-combining sites and is still capable of cross-linking antigen. A Fab fragment contains the constant domain of the light chain and the first constant domain (CH1) of the heavy chain. Fab' fragments differ from Fab fragments by the addition of a few residues at the carboxyl terminus of the heavy chain CH1 domain including one or more cysteine(s) from the antibody hinge region. F(ab')2 antibody fragments were originally produced as pairs of Fab' fragments that have hinge cysteines between them.

Also within the scope of the present invention are methods of making an anti-AS-SPIK antibody. For example, variable regions can be constructed using PCR mutagenesis methods to alter DNA sequences encoding an immunoglobulin chain (e.g., using methods employed to generate humanized immunoglobulins.

Monoclonal antibodies are homogeneous antibodies of identical antigenic specificity produced by a single clone of antibody-producing cells, and polyclonal antibodies generally recognize different epitopes on the same antigen and are produced by more than one clone of antibody producing cells. Each monoclonal antibody is directed against a single determinant on the antigen. The modifier, monoclonal, indicates the character of the antibody as being obtained from a substantially homogeneous population of antibodies, and is not to be construed as requiring production of the antibody by any particular method.

The monoclonal antibodies herein can include chimeric antibodies, i.e., antibodies that typically have a portion of the heavy and/or light chain identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity. Chimeric antibodies of interest include primatized antibodies comprising variable domain antigen-binding sequences derived from a non-human primate (e.g. apes, Old World monkeys, New World monkeys, prosimians) and human constant region sequences.

Murine and rabbit monoclonal antibodies were generated through the immunization of a mouse or a rabbit with specifically designed recombinant proteins, that has the extra 23 amino acid sequence found in AS-SPIK (SEQ ID NO: 81) that is not found in NS-SPIK, in addition to the common region (SEQ ID NO: 83), which is the amino acid sequence found both in NS-SPIK and AS-SPIK. In some embodiments, the recombinant proteins may not need to have the entire 23 amino acid sequence (SEQ ID NO: 81) to generate an antibody being effective at binding only to AS-SPIK but not to NS-SPIK. The method for screening and selecting an antibody which specifically or preferentially binds to AS-SPIK is described in Example 1.

Figure 1:
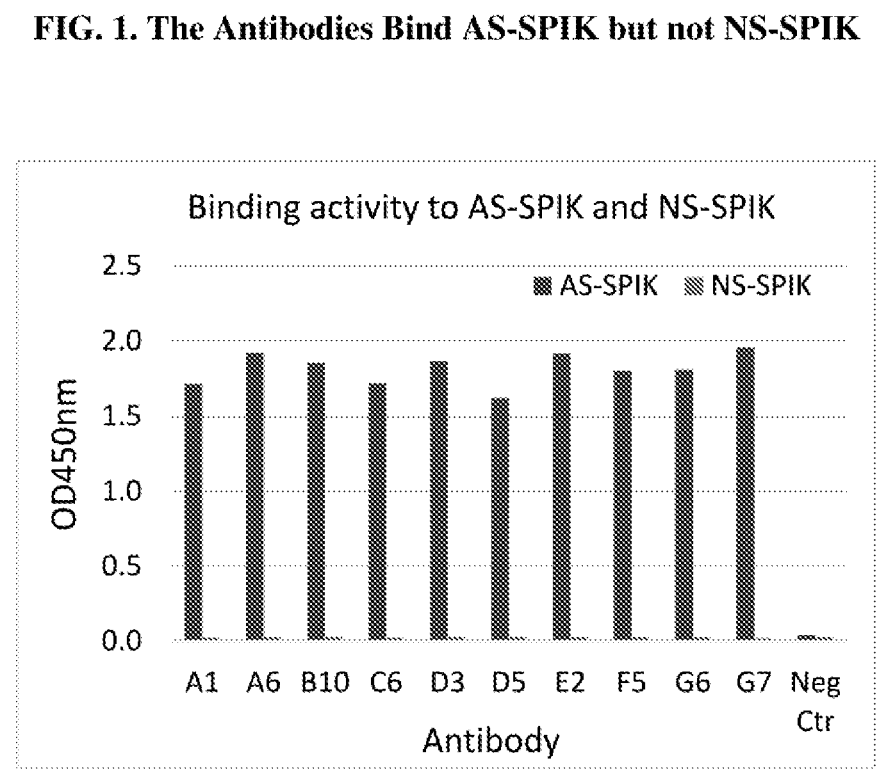

In FIG. 1 the test results of monoclonal antibodies are provided, which show that antibodies of the invention are able to specifically or preferentially recognize AS-SPIK but not NS-SPIK; these include but are not limited to IM-A1, IM-A6, IM4-B10, IM-C6, IM-D3, IM-D5, IM-E2, IM-F5, IM-G6 and IM-G7. See Example 1 for description of the tests.

The sequences of the variable region of the light chain (VL) and the heavy chain (VH) of monoclonal antibodies, which specifically or preferentially bind to AS-SPIK (and not to NS-SPIK), were determined (SEQ ID NOs: 1-20). All CDRs of these antibodies were also determined (SEQ ID NOs: 21-80). FIGS. 3-6 provide the consensus amino acid sequences of these regions. Tables 1-3 provide the SEQ ID NO: for the various VH and VL regions of ten exemplary antibodies of the invention.

For example, the IM-A1 antibody has the VH region shown in SEQ ID NO: 1 and has the VL region shown in SEQ ID NO: 11. The VH region has three CDR regions corresponding to SEQ ID NOs: 21, 31 and 41. The VL region has three CDRs corresponding to SEQ ID NOs: 51, 61 and 71.

The IM-A6 antibody has the VH region shown in SEQ ID NO: 2 and has the VL region shown in SEQ ID NO: 12. The VH region has three CDR regions corresponding to SEQ ID NOs: 22, 32 and 42. The VL region has three CDR regions corresponding to SEQ ID NOs: 52, 62 and 72.

The IM-B10 antibody has the VH region shown in SEQ ID NO: 3 and has the VL region shown in SEQ ID NO: 13. The VH region has three CDR regions corresponding to SEQ ID NOs: 23, 33 and 43. The VL region has three CDR regions corresponding to SEQ ID NOs: 53, 63 and 73.

The IM-C6 antibody has the VH region shown in SEQ ID NO: 4 and has the VL region shown in SEQ ID NO: 14. The VH region has three CDR regions corresponding to SEQ ID NOs: 24, 34 and 44. The VL region has three CDR regions corresponding to SEQ ID NOs: 54, 64 and 74.

The IM-D3 antibody has the VH region shown in SEQ ID NO: 5 and has the VL region shown in SEQ ID NO: 15. The VH region has three CDR regions corresponding to SEQ ID NOs: 25, 35 and 45. The VL region has three CDR regions corresponding to SEQ ID NOs: 55, 65 and 75.

The IM-D5 antibody has the VH region shown in SEQ ID NO: 6 and has the VL region shown in SEQ ID NO: 16. The VH region has three CDR regions corresponding to SEQ ID NOs: 26, 36 and 46. The VL region has three CDR regions corresponding to SEQ ID NOs: 56, 66 and 76.

The IM-E2 antibody has the VH region shown in SEQ ID NO: 7 and has the VL region shown in SEQ ID NO: 17. The VH region has three CDR regions corresponding to SEQ ID NOs: 27, 37 and 47. The VL region has three CDR regions corresponding to SEQ ID NOs: 57, 67 and 77.

The IM-F5 antibody has the VH region shown in SEQ ID NO: 8 and has the VL region shown in SEQ ID NO: 18. The VH region has three CDR regions corresponding to SEQ ID NOs: 28, 38 and 48. The VL region has three CDR regions corresponding to SEQ ID NOs: 58, 68 and 78.

The IM-G6 antibody has the VH region shown in SEQ ID NO: 9 and has the VL region shown in SEQ ID NO: 19. The VH region has three CDR regions corresponding to SEQ ID NOs: 29, 39 and 49. The VL region has three CDR regions corresponding to SEQ ID NOs: 59, 69 and 79.

The IM-G7 antibody has the VH region shown in SEQ ID NO: 10 and has the VL region shown in SEQ ID NO: 20. The VH region has three CDR regions corresponding to SEQ ID NOs: 30, 40 and 50. The VL region has three CDR regions corresponding to SEQ ID NOs: 60, 70 and 80.

In addition, antibodies in accordance with embodiments of the invention can be any non-naturally occurring (man-made) antibody that binds specifically or preferentially to AS-SPIK and does not bind to NS-SPIK.

In some embodiments, an antibody comprises a VH region having a sequence provided in any one of SEQ ID NOs: 1-10, or has a VH region comprising a sequence having at least about 80%, at least about 85%, at least about 90%, at least about 95%, or at least about 99% percent identity to the heavy chain variable region sequence in any one of SEQ ID NOs: 1-10, provided the resulting antibody or antigen-binding fragment specifically or preferentially binds to AS-SPIK and does not bind NS-SPIK.

In some embodiments, an antibody comprises a VL region having a sequence provided in any one of SEQ ID NOs: 11-20, or has a VL comprising a sequence having at least about 80%, at least about 85%, at least about 90%, at least about 95%, or at least about 99% percent identity to the heavy chain variable region sequence in any one of SEQ ID NOs: 11-20, provided the resulting antibody or antigen-binding fragment specifically or preferentially binds to AS-SPIK and does not bind NS-SPIK.

In some embodiments, an antibody comprises a VH CDR1 region having a sequence provided in any one of SEQ ID NOs: 21-30, or comprising two or fewer amino acid mutations in any one of SEQ ID NOs: 21-30, as long as the resulting antibody specifically or preferentially binds to AS-SPIK and does not bind NS-SPIK. In some embodiments, a VH CDR1 region may comprise the following structural formula, where an X indicates a variable amino acid, which may be any of the identified amino acids: S $X_1$ $X_2$ $X_3$ $X_4$ S (SEQ ID NO: 107), where $X_1$ is S or A; $X_2$ is Y or N; $X_3$ is A, G, P or V; and $X_4$ is I or V.

In some embodiments, an antibody comprises a VH CDR2 region having a sequence provided in any one of SEQ ID NOs: 31-40, or comprising two or fewer amino acid mutations in any one of SEQ ID NOs: 31-40, as long as the resulting antibody specifically or preferentially binds to AS-SPIK and does not bind NS-SPIK. In some embodiments, a VH CDR2 region may comprise the following structural formula, where an X indicates a variable amino acid, which may be any of the identified amino acids: $X_5$ I $X_6$ $X_7$ $X_8$ G $X_9$ $X_{10}$ $X_{11}$ Y A S W A K S (SEQ ID NO: 108), where $X_8$ is S, G or Y; and $X_5$, $X_6$, $X_7$, $X_9$, $X_{10}$ and $X_{11}$ are any amino acid.

In some embodiments, an antibody comprises a VH CDR3 region having a sequence provided in any one of SEQ ID NOs: 41-50, or comprising two or fewer amino acid mutations in any one of SEQ ID NOs: 41-50, as long as the resulting antibody specifically or preferentially binds to AS-SPIK and does not bind NS-SPIK. In some embodiments, a VH CDR3 region may comprise the following structural formula, where an X indicates a variable amino acid, which may be any of the identified amino acids: R $X_{12}$ $X_{13}$ $X_{14}$ $X_{15}$ $X_{16}$ $X_{17}$ $X_{18}$ $X_{19}$ $X_{20}$ $X_{21}$ (SEQ ID NO: 109), where $X_{12}$, $X_{13}$, $X_{14}$, $X_{15}$, $X_{16}$, $X_{17}$, $X_{18}$, $X_{19}$, $X_{20}$, and $X_{21}$ are any amino acid.

In some embodiments, an antibody comprises a VL CDR1 region having a sequence provided in any one of SEQ ID NOs: 51-60, or comprising two or fewer amino acid mutations in any one of SEQ ID NOs: 51-60, as long as the resulting antibody specifically or preferentially binds to AS-SPIK and does not bind NS-SPIK. In some embodiments, a VL CDR1 region may comprise the following structural formula, where an X indicates a variable amino acid, which may be any of the identified amino acids: Q A S $X_{22}$ $X_{23}$ I $X_{24}$ $X_{25}$ $X_{26}$ L $X_{27}$ (SEQ ID NO: 110), where $X_{22}$ is Q or E; $X_{23}$ is S, G, D or N; $X_{24}$ is S, N, E or G; $X_{25}$ is any amino acid; $X_{26}$ is Y or A; and $X_{27}$ is any amino acid.

In some embodiments, an antibody comprises a VL CDR2 region having a sequence provided in any one of SEQ ID NOs: 61-70, or comprising two or fewer amino acid mutations in any one of SEQ ID NOs: 61-70, as long as the resulting antibody specifically or preferentially binds to AS-SPIK and does not bind NS-SPIK. In some embodiments, a VL CDR2 region may comprise the following structural formula, where an X indicates a variable amino acid, which may be any of the identified amino acids: $X_{28}$ A $X_{29}$ $X_{30}$ L $X_{31}$ S (SEQ ID NO: 111), where $X_{28}$ is any amino acid; $X_{29}$ is S or T; $X_{30}$ is T, Y or K; and $X_{31}$ is A, P or V.

In some embodiments, an antibody comprises a VL CDR3 region having a sequence provided in any one of SEQ ID NOs: 71-80, or comprising two or fewer amino acid mutations in any one of SEQ ID NOs: 71-80, as long as the resulting antibody specifically or preferentially binds to AS-SPIK and does not bind NS-SPIK. In some embodiments, a VL CDR3 region may comprise the following structural formula, where an X indicates a variable amino acid, which may be any of the identified amino acids: $X_{32}$ Q $X_{33}$ Y $X_{34}$ $X_{35}$ $X_{36}$ $X_{37}$ $X_{38}$ $X_{39}$ $X_{40}$ $X_{41}$ (SEQ ID NO: 112), wherein $X_{32}$ is Q or H; $X_{33}$ is G or D; $X_{34}$ is any amino acid; $X_{35}$ is any amino acid; $X_{36}$ is S or N; $X_{37}$ is N, D, V or G; $X_{38}$ is V, D or I; $X_{39}$ is D, G or N; $X_{40}$ is N or V; and $X_{41}$ is any amino acid.

Antibodies in accordance with embodiments of the invention can comprise any of the herein described VH, VL, VH CDR1, VH CDR2 or VH CDR3, or VL CDR1, VL CDR2, or VL CDR3 regions or any combination of these regions, including sequences with the recited homologies or percent identities provided above, so long as the antibodies bind to AS-SPIK and not to NS-SPIK.

The structural formulae and consensus sequences described herein were determined using the software program "BioEdit", which was developed by North Carolina State University.

The high binding activity of all these antibodies to AS-SPIK was studied. The results are described in Example 1.

Methods for producing monoclonal antibodies can include purification steps. For example, the antibodies can generally be further purified, for example, using filtration, centrifugation and various chromatographic methods, such as HPLC or affinity chromatography, all of which are techniques well known to one of ordinary skill in the art. These purification techniques each involve fractionation to separate the desired antibody from other components of a mixture. Analytical methods particularly suited to the preparation of antibodies include, for example, protein A-Sepharose and/or protein G-Sepharose chromatography.

The anti-AS-SPIK antibodies of the invention may include CDRs from a human or non-human source. "Humanized" antibodies are generally chimeric or mutant monoclonal antibodies from mouse, rat, hamster, rabbit or other species, bearing human constant and/or variable region domains or specific changes. The framework of the immunoglobulin can be human, humanized, or non-human (e.g., a murine framework modified to decrease antigenicity in humans), or a synthetic framework (e.g., a consensus sequence). Humanized immunoglobulins are those in which the framework residues correspond to human germline sequences and the CDRs result from V(D)J recombination and somatic mutations. However, humanized immunoglobulins may also comprise amino acid residues not encoded in human germline immunoglobulin nucleic acid sequences (e.g., mutations introduced by random or site-specific mutagenesis ex vivo). An antibody variable domain gene based on germline sequence but possessing framework mutations introduced by, for example, an in vivo somatic mutational process is termed "human."

Humanized antibodies may be engineered by a variety of methods known in the art including, for example: (1) grafting the non-human complementarity determining regions (CDRs) onto a human framework and constant region (a process referred to in the art as humanizing), or, alternatively, (2) transplanting the entire non-human variable domains, but providing them with a human-like surface by replacement of surface residues (a process referred to in the art as veneering). Humanized antibodies can include both humanized and veneered antibodies. Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire.

In addition to chimeric and humanized antibodies, fully human antibodies can be derived from transgenic mice having human immunoglobulin genes. In some embodiments, antibodies may be produced and identified by scFv-phage display libraries.

The anti-AS-SPIK antibodies may be modified to modulate their antigen binding affinity, their effector functions, or their pharmacokinetics. In particular, random mutations can be made in the CDRs and products screened to identify antibodies with higher affinities and/or higher specificities. Typically, the CDRs may differ in 1 or 2 amino acids.

CDR shuffling and implantation technologies can be used with the antibodies provided herein, for example. CDR shuffling inserts CDR sequences into a specific framework region. CDR implantation techniques permit random combination of CDR sequences into a single master framework. Using such techniques, CDR sequences of the anti-AS-SPIK antibody, for example, can be mutagenized to create a plurality of different sequences, which can be incorporated into a scaffold sequence and the resultant antibody variants screened for desired characteristics, e.g., higher affinity.

Our study of the function of SPIK shows that SPIK can bind Granzyme A (GzmA) and inhibit it from inducing apoptosis. Lu et al., Immunology 2011; 134(4):398-408. GzmA is a cytotoxic serine protease secreted by activated CTLs and NK cells to kill target cells during immune surveillance. The role of GzmA-induced apoptosis in removal of malignant cells, such as tumor precursor/tumor germ cells, has been confirmed. Pardo et al., Eur J Immunol 2002; 32(10):2881-2887. Therefore, it is possible that over-expression of AS-SPIK in liver cancer cells will cause the cell to be resistant to the apoptosis induced by GzmA during immune-clearance. This results in the escape of these cancer cells from killing by the immune pathways. Lu et al., Immunology 2011; 134(4):398-408. Based on this hypothesis, and without being held to theory, we conclude that suppression of the over-expression of AS-SPIK, or the inhibition of the activity of over-expressed AS-SPIK, may restore the immuno-killing of cancer cells induced by GzmA during the human body's immune clearance.

Anti-AS-SPIK antibodies in accordance with embodiments of the invention can inhibit the activity of AS-SPIK, as demonstrated by the disclosure of PCT Application No. PCT/US19/20999, the disclosure of which is incorporated herein by reference in its entirety. Therefore, it is possible to use an anti-AS-SPIK antibody to block the binding of AS-SPIK with GzmA, free the GzmA, and restore the apoptotic killing of these cancer cells via immune-clearance. For this purpose, an anti-SPIK antibody may be used in the treatment of disorders characterized by the expression of AS-SPIK, including, but not limited to, cancer, viral infection, and inflammation.

One therapeutic use of antibodies is through humanization. Therapy with humanized monoclonal antibodies is an area that is being developed rapidly and their specificity and efficiency are well studied. Rothernberg, M E, Cell 2016; 165(3):509. The subject anti-AS-SPIK monoclonal antibodies, including but not limited to IM-A1, IM-A6, IM-B10, IM-C6, IM-D3, IM-D5, IM-E2, IM-F5, IM-G6 and IM-G7, and other antibodies of the invention, which are able to inhibit the activity of SPIK, can also be humanized and used for treatment of disease.

Recombinant technology using, for example phagemid technology, allows for preparation of antibodies having a desired specificity from recombinant genes encoding a range of antibodies. Certain recombinant techniques involve isolation of antibody genes by immunological screening of combinatorial immunoglobulin phage expression libraries prepared from RNA isolated from spleen of an immunized animal. For such methods, combinatorial immunoglobulin phagemid libraries can be prepared from RNA isolated from spleen of an immunized animal, and phagemids expressing appropriate antibodies can be selected by panning using cells expressing antigen and control cells.

In addition to the combinatorial immunoglobulin phage expression libraries disclosed above, one molecular cloning approach is to prepare antibodies from transgenic mice containing human antibody libraries. Such transgenic animals can be employed to produce human antibodies of a single isotype, more specifically an isotype that is essential for B cell maturation, such as IgM and possibly IgD.

The anti-AS-SPIK immunoglobulins may be modified to reduce or abolish glycosylation. An immunoglobulin that lacks glycosylation may be an immunoglobulin that is not glycosylated at all; that is not fully glycosylated; or that is atypically glycosylated (i.e., the glycosylation pattern for the mutant differs from the glycosylation pattern of the corresponding wild type immunoglobulin). The IgG polypeptides include one or more (e.g., 1, 2, or 3 or more) mutations that attenuate glycosylation, i.e., mutations that result in an IgG CH2 domain that lacks glycosylation, or is not fully glycosylated or is atypically glycosylated. The oligosaccharide structure can also be modified, for example, by eliminating the fucose moiety from the N-linked glycan.

Antibodies can also be modified to increase their stability and or solubility in vivo by conjugation to non-protein polymers, e.g., polyethylene glycol. Any PEGylation method can be used as long as the anti-AS-SPIK antibody retains the ability to selectively bind AS-SPIK and not NS-SPIK.

A wide variety of antibody/immunoglobulin frameworks or scaffolds can be employed so long as the resulting polypeptide includes at least one binding region that is specific for the target, i.e., AS-SPIK. Such frameworks or scaffolds include the five main idiotypes of human immunoglobulins, or fragments thereof (such as those disclosed elsewhere herein), and include immunoglobulins of other animal species, preferably having humanized aspects. Single heavy-chain antibodies such as those identified in camelids are of particular interest in this regard.

The anti-AS-SPIK antibodies of the invention specifically or preferentially bind to an epitope on AS-SPIK and do not bind to an epitope on NS-SPIK. An epitope refers to an antigenic determinant on a target that is specifically bound by the paratope, i.e., the binding site of an antibody. Epitopic determinants usually consist of chemically active surface groupings of molecules such as amino acids or sugar side chains, and typically have specific three-dimensional structural characteristics, as well as specific charge characteristics. Epitopes generally have between about 4 to about 10, preferably 4 to 8, contiguous amino acids (a linear or continuous epitope), or alternatively can be a set of non-contiguous amino acids that define a particular structure (e.g., a conformational epitope). Thus, an epitope can consist of at least 4, at least 6, at least 8, at least 10, and at least 12 such amino acids. Methods of determining the spatial conformation of amino acids are known in the art, and include, for example, x-ray crystallography, 2-dimensional nuclear magnetic resonance, and Precision Epitope Mapping with CLIPS (Chemically Linked Peptides on Scaffolds) Peptide Array (Timmerman, Puijk et al., J Mol Recognit, 20(5), 283-299, (2007).

Methods of predicting other potential epitopes to which an antibody can bind can include but are not limited to, Kyte-Doolittle Analysis (Kyte and Dolittle, J. Mol. Biol. 157:105-132 (1982)), Hopp and Woods Analysis (Hopp and Woods, Proc. Natl. Acad. Sci. USA 78:3824-3828 (1981); Hopp and Woods, Mol. Immunol. 20:483-489 (1983); Hopp, J. Immunol. Methods 88:1-18 (1986)), Jameson-Wolf Analysis (Jameson and Wolf, Comput. Appl. Biosci. 4:181-186 (1988)), and Emini Analysis (Emini et al., Virology 140:13-20 (1985)), Chou and Fasman analysis (Ponomarenko & Regenmortel, Structural Bioinformatics, 2009), Karplus and Schulz Analysis (Kolaskar and Tongaonkar Analysis Kolaskar & Tongaonkar, FEBS Letters, 172-174 (1990)), and Parker analysis. In some embodiments potential epitopes are determined through correlations with known antigenic sites from other studies and these predictive techniques can be combined with structural data, such as X-ray crystallographic data. Epitope prediction may also include techniques that predict both continuous and discontinuous epitopes. Methods of predicting discontinuous epitopes includes but are not limited to the following: DiscoTope, BEpro, ElliPro, SEPPA, EPITOPIA, EPCES, Bpredictor, and EPMeta (Yao et al., PLOS ONE, (2013)). In some embodiments, potential epitopes are identified by determining theoretical extracellular domains. Analysis algorithms such as TMpred (see Hofmann and Stoffel, Biol. Chem. 374:166 (1993)) or TMHMM (Krogh et al., J. Mol. Biol., 305(3):567-580 (2001)) can be used to make such predictions. Other algorithms, such as SignalP 3.0 (Bednsten et al., J. Mol. Biol. 340(4):783-795 (2004)) can be used to predict the presence of signal peptides and to predict where those peptides would be cleaved from the full-length protein. The portions of the proteins on the outside of the cell can serve as targets for antibody interaction.

The compositions of the present invention include antibodies described herein that (1) exhibit a threshold level of binding activity; (2) do not significantly cross-react with known related polypeptide molecules; (3) bind to AS-SPIK and (4) do not bind to NS-SPIK. The binding affinity of an antibody can be readily determined by one of ordinary skill in the art, for example, by Scatchard analysis (Scatchard, Ann. NY Acad, Sci. 51:660-672 (1949)).

In some embodiments, the anti-AS-SPIK antibodies can bind to their target epitopes or mimetic decoys at least 1.5-fold, 2-fold, 5-fold, 10-fold, 100-fold, 103-fold, 104-fold, 105-fold, 106-fold or greater for the target AS-SPIK than to other proteins predicted to have some homology to AS-SPIK, for example, NS-SPIK.

In some embodiments, the anti-AS-SPIK antibodies bind with high affinity of 10−4 M or less, $10^{-7}$ M or less, $10^{-9}$ M or less or with subnanomolar affinity (0.9, 0.8, 0.7, 0.6, 0.5, 0.4, 0.3, 0.2, 0.1 nM or even less). In some embodiments, the binding affinity of the anti-AS-SPIK antibodies for their respective targets is at least $1\times10^{6}$ Ka. In some embodiments the binding affinity of the anti-AS-SPIK antibodies for AS-SPIK is at least $5\times10^{6}$ Ka, at least $1\times10^{7}$ Ka, at least $2\times10^{7}$ Ka, at least $1\times10^{8}$ Ka, or greater. Antibodies may also be described or specified in terms of their binding affinity to AS-SPIK. In some embodiments binding affinities include those with a Kd less than $5\times10^{-2}$ M, $10^{-2}$ M, $5\times10^{-3}$ M, $10^{-3}$ M, $5\times10^{-3}$ M, $10^{-4}$ M, $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M, or less. That is, the term “specific binding,” “specifically binding,” or “specifically bind,” e.g. to AS-SPIK, as used herein refers to an antibody that binds to AS-SPIK and does not bind to NS-SPIK. While not being bound by theory, it is believed that antibodies of the invention that specifically bind to AS-SPIK bind to an epitope that is only within the first 1-23 amino acids present in AS-SPIK (see SEQ ID NO: 82) but not present in NS-SPIK. It could be that the antibodies of the invention bind to epitopes that span the 1-23 amino acids of the AS-SPIK but also include some amino acids in the common region (SEQ ID NO: 83). Or it could be that the antibody binds at least one amino acid in the first 1-23 amino acids of AS-SPIK (SEQ ID NO: 82) but also binds at least one amino acid in the common region (SEQ ID NO: 83). In these instances, the antibodies may also bind to NS-SPIK, but the level of binding is at or below background levels. This is referred to herein as "preferentially binding" or "preferential bind." The antibodies that preferentially bind AS-SPIK are still useful in diagnostic methods because the assays can be developed so as to discount the background levels of binding as "noise." As such, the assay would indicate that only certain levels of binding (above a certain threshold level and above the background noise) are acceptable to result in a diagnosis of the patient having a disorder characterized by expression of AS-SPIK, e.g., a liver disorder, such as liver cancer.

The antibodies of the invention may bind with an affinity of $10^{-4}$ M or less, $10^{-7}$ M or less, $10^{-9}$ M or less or with sub-nanomolar affinity (0.9, 0.8, 0.7, 0.6, 0.5, 0.4, 0.3, 0.2, 0.1 nM or even less). In some embodiments, the binding affinity of the anti-AS-SPIK antibodies for their respective targets is at least $1 \times 10^6$ Ka. In some embodiments, the binding affinity of the anti-AS-SPIK antibodies for AS-SPIK is at least $5 \times 10^6$ Ka, at least $1 \times 10^7$ Ka, at least $2 \times 10^7$ Ka, at least $1 \times 10^8$ Ka, or greater. In some embodiments, the binding affinities include those with a Kd less than $5 \times 10^{-2}$ M, $10^{-2}$ M, $5 \times 10^3$ M, $10^{-3}$ M, $5 \times 10^{-3}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{15}$ M, or $10^{-15}$ M, or less. In contrast thereto, the term "non-specifically binding", e.g. to NS-SPIK, as used herein refers to a binding affinity that is by a factor of at least 1.5, 2, 5, 10, 100, $10^3$, $10^4$, $10^5$, $10^6$ or greater less than that determined for the "specific binding", e.g. to AS-SPIK. Affinities, such as Kd, may be measured by a radiolabeled antigen-binding assay (radioimmuno assay, RIA) performed with a Fab-version of an antibody of interest and its antigen. According to another embodiment, Kd may be measured using surface plasmon resonance assays with immobilized antigen. In a preferred embodiment, the antibody of the invention specifically or preferentially binds to AS-SPIK and does not specifically bind to NS-SPIK, wherein the affinity of the antibody to AS-SPIK is at least 1.5-fold, 2-fold, 5-fold, 10-fold, 100-fold, $10^3$-fold, $10^4$-fold, $10^5$-fold or $10^6$-fold greater than to NS-SPIK.

In some embodiments, the antibodies do not bind to known related polypeptide molecules; for example, they bind AS-SPIK but not known related polypeptides, for example, NS-SPIK. Antibodies may be screened against known related polypeptides to isolate an antibody population that specifically or preferentially binds AS-SPIK. For example, antibodies specific for AS-SPIK will flow through a column comprising NS-SPIK adhered to insoluble matrix under appropriate buffer conditions. Such screening allows isolation of polyclonal and monoclonal antibodies non-cross-reactive to closely related polypeptides. Other methods of screening and isolation of specific antibodies include, without limitation, for example, concurrent immunoelectrophoresis, radioimmunoassay (RIA), radioimmunoprecipitation, enzyme-linked immunosorbent assay (ELISA), dot blot or Western blot assay, inhibition or competition assay, and sandwich assay.

Antibodies in accordance with embodiments of the invention can include a detectable label, which may also be referred to as a reporter (e.g., a detectable reporter). In some embodiments, a detectable label can be any molecule that is covalently linked to an antibody (e.g., an anti-AS-SPIK antibody) or a biologically-active fragment thereof that allows for qualitative and/or quantitative assessment of the expression or activity of the tagged peptide. The activity can include a biological activity, a physico-chemical activity, or a combination thereof. Both the form and position of the detectable label can vary, as long as the labeled antibody retains biological activity. Many different labels can be used, and the choice of a particular label will depend upon the desired application. Labeled anti-AS-SPIK antibodies can be used, for example, for assessing the levels of AS-SPIK in a biological sample, e.g., urine, saliva, cerebrospinal fluid, blood or a biopsy sample.

Detectable labels can include enzymes, photo-affinity ligands, radioisotopes, and fluorescent or chemiluminescent compounds. Exemplary enzymatic labels can include horseradish peroxidase, alkaline phosphatase, β-galactosidase, and urease. The covalent linkage of an anti-AS-SPIK antibody to an enzyme may be performed by different methods, for example, the coupling with glutaraldehyde via free amino groups. Alternatively, anti-AS-SPIK antibody can be coupled to the enzyme via sugar residues. Other enzyme containing carbohydrates can also be coupled to the antibody in this manner. Enzyme coupling may also be performed by interlinking the amino groups of the antibody with free thiol groups of an enzyme, such as β-galactosidase, using a heterobifunctional linker, such as succinimidyl 6-(N-maleimido) hexanoate. The horseradish-peroxidase detection system can be used, for example, with the chromogenic substrate tetramethylbenzidine (TMB), which yields a soluble product in the presence of hydrogen peroxide that is detectable at 450 nm. The alkaline phosphatase detection system can be used with the chromogenic substrate p-nitrophenyl phosphate, for example, which yields a soluble product readily detectable at 405 nm. Similarly, the β-galactosidase detection system can be used with the chromogenic substrate o-nitrophenyl-P-D-galactopyranoxide (ONPG), which yields a soluble product detectable at 410 nm. A urease detection system can be used with a substrate, such as urea-bromocresol purple.

A detectable label can be a fluorescent label, including, but not limited to, fluorescein isothiocyanate, rhodamine, phycoerytherin, phycocyanin, allophycocyanin, o-phthaldehyde and fluorescamine; a chemiluminescent compound selected from the group consisting of luminol, isoluminol, an aromatic acridinium ester, an imidazole, an acridinium salt and an oxalate ester; a liposome or dextran; or a bioluminescent compound such as luciferin, luciferase and aequorin. Alternatively or in addition, detectable labels include, but are not limited to, a radiopaque or contrast agent such as barium, diatrizoate, ethiodized oil, gallium citrate, iocarmic acid, iocetamic acid, iodamide, iodipamide, iodoxamic acid, iogulamide, iohexol, iopamidol, iopanoic acid, ioprocemic acid, iosefamic acid, ioseric acid, iosulamide meglumine, iosemetic acid, iotasul, iotetric acid, iothalamic acid, iotroxic acid, ioxaglic acid, ioxotrizoic acid, ipodate, meglumine, metrizamide, metrizoate, propyliodone, and thallous chloride.

Labels can be added during synthesis or post-synthetically. Recombinant anti-AS-SPIK antibodies or biologically active variants thereof can also be labeled by the addition of labeled precursors (e.g., radiolabeled amino acids) to the culture medium in which the transformed cells are grown. In some embodiments, analogues or variants of peptides can be used in order to facilitate incorporation of detectable markers. For example, any N-terminal phenylalanine residue can be replaced with a closely related aromatic amino acid, such as tyrosine, that can be easily labeled with $^{125}$I. In some embodiments, additional functional groups that support effective labeling can be added to the fragments of an anti-AS-SPIK antibody or biologically active variants thereof. For example, a 3-tributyltinbenzoyl group can be added to the N-terminus of the native structure; subsequent displacement of the tributyltin group with $^{125}$I will generate a radiolabeled iodobenzoyl group.

Antibody Drug Conjugates (ADCs)

Aspects of the invention include immunoconjugates, or antibody-drug conjugates (ADC), comprising an antibody conjugated to a cytotoxic agent such as a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate). In another aspect, the invention further provides methods of using the immunoconjugates. In one aspect, an immunoconjugate comprises any of the above anti-AS-SPIK antibodies covalently attached to a cytotoxic agent or a detectable agent. ADCs are described, for example, in U.S. Pat. No. 8,362,213, the disclosure of which is incorporated by reference herein in its entirety.

The use of ADCs for the local delivery of cytotoxic or cytostatic agents, i.e., drugs to kill or inhibit tumor cells in the treatment of cancer (Lambert, J. (2005) Curr. Opinion in Pharmacology 5:543-549; Wu et al (2005) Nature Biotechnology 23(9):1137-1146; Payne, G. (2003) Cancer Cell 3:207-212; Syrigos and Epenetos (1999) Anticancer Research 19:605-614; Niculescu-Duvaz and Springer (1997) Adv. Drug Del. Rev. 26:151-172; U.S. Pat. No. 4,975,278) allows targeted delivery of the drug moiety to tumors, and intracellular accumulation therein, where systemic administration of these unconjugated drug agents may result in unacceptable levels of toxicity to normal cells as well as the tumor cells sought to be eliminated (Baldwin et al (1986) Lancet pp. (Mar. 15, 1986):603-05; Thorpe, (1985) "Antibody Carriers Of Cytotoxic Agents In Cancer Therapy: A Review," in Monoclonal Antibodies '84: Biological And Clinical Applications, A. Pinchera et al (ed.s), pp. 475-506). Efforts to improve the therapeutic index, i.e., maximal efficacy and minimal toxicity of ADC have focused on the selectivity of polyclonal (Rowland et al (1986) Cancer Immunol. Immunother., 21:183-87) and monoclonal antibodies (mAbs) as well as drug-linking and drug-releasing properties (Lambert, J. (2005) Curr. Opinion in Pharmacology 5:543-549). Drug moieties used in ADCs include bacterial protein toxins such as diphtheria toxin, plant protein toxins such as ricin, small molecules such as auristatins, geldanamycin (Mandler et al (2000) J. of the Nat. Cancer Inst. 92(19):1573-1581; Mandler et al (2000) Bioorganic & Med. Chem. Letters 10:1025-1028; Mandler et al (2002) Bioconjugate Chem. 13:786-791), maytansinoids (EP 1391213; Liu et al (1996) Proc. Natl. Acad. Sci. USA 93:8618-8623), calicheamicin (Lode et al (1998) Cancer Res. 58:2928; Hinman et al (1993) Cancer Res. 53:3336-3342), daunomycin, doxorubicin, methotrexate, and vindesine (Rowland et al (1986) supra). The drug moieties may affect cytotoxic and cytostatic mechanisms including tubulin binding, DNA binding, or topoisomerase inhibition. Some cytotoxic drugs tend to be inactive or less active when conjugated to large antibodies or protein receptor ligands.

The auristatin peptides, auristatin E (AE) and monomethylauristatin (MMAE), synthetic analogs of dolastatin (WO 02/088172), have been conjugated as drug moieties to: (i) chimeric monoclonal antibodies cBR96 (specific to Lewis Y on carcinomas); (ii) cAC10 which is specific to CD30 on hematological malignancies (Klussman, et al (2004), Bioconjugate Chemistry 15(4):765-773; Doronina et al (2003) Nature Biotechnology 21(7):778-784; Francisco et al (2003) Blood 102(4):1458-1465; US 2004/0018194; (iii) anti-CD20 antibodies such as rituxan (WO 04/032828) for the treatment of CD20-expressing cancers and immune disorders; (iv) anti-EphB2R antibody 2H9 for treatment of colorectal cancer (Mao et al (2004) Cancer Research 64(3): 781-788); (v) E-selectin antibody (Bhaskar et al (2003) Cancer Res. 63:6387-6394); (vi) trastuzumab (HERCEPTIN®, US 2005/0238649), and (vi) anti-CD30 antibodies (WO 03/043583). Variants of auristatin E are disclosed in U.S. Pat. Nos. 5,767,237 and 6,124,431. Monomethyl auristatin E conjugated to monoclonal antibodies are disclosed in Senter et al, Proceedings of the American Association for Cancer Research, Volume 45, Abstract Number 623, presented Mar. 28, 2004. Auristatin analogs MMAE and MMAF have been conjugated to various antibodies (US 2005/0238649).

Conventional means of attaching, i.e., linking through covalent bonds, a drug moiety to an antibody generally leads to a heterogeneous mixture of molecules where the drug moieties are attached at a number of sites on the antibody. For example, cytotoxic drugs have typically been conjugated to antibodies through the often-numerous lysine residues of an antibody, generating a heterogeneous antibody-drug conjugate mixture. Depending on reaction conditions, the heterogeneous mixture typically contains a distribution of antibodies with from 0 to about 8, or more, attached drug moieties. In addition, within each subgroup of conjugates with a particular integer ratio of drug moieties to antibody, is a potentially heterogeneous mixture where the drug moiety is attached at various sites on the antibody. Analytical and preparative methods may be inadequate to separate and characterize the antibody-drug conjugate species molecules within the heterogeneous mixture resulting from a conjugation reaction. Antibodies are large, complex and structurally diverse biomolecules, often with many reactive functional groups. Their reactivities with linker reagents and drug-linker intermediates are dependent on factors such as pH, concentration, salt concentration, and co-solvents. Furthermore, the multistep conjugation process may be non-reproducible due to difficulties in controlling the reaction conditions and characterizing reactants and intermediates.

Cysteine thiols are reactive at neutral pH, unlike most amines which are protonated and less nucleophilic near pH 7. Since free thiol (RSH, sulfhydryl) groups are relatively reactive, proteins with cysteine residues often exist in their oxidized form as disulfide-linked oligomers or have internally bridged disulfide groups. Extracellular proteins generally do not have free thiols (Garman, 1997, Non-Radioactive Labelling: A Practical Approach, Academic Press, London, at page 55). Antibody cysteine thiol groups are generally more reactive, i.e. more nucleophilic, towards electrophilic conjugation reagents than antibody amine or hydroxyl groups. Cysteine residues have been introduced into proteins by genetic engineering techniques to form covalent attachments to ligands or to form new intramolecular disulfide bonds (Better et al (1994) J. Biol. Chem. 13:9644-9650; Bernhard et al (1994) Bioconjugate Chem.

5:126-132; Greenwood et al (1994) Therapeutic Immunology 1:247-255; Tu et al (1999) Proc. Natl. Acad. Sci. USA 96:4862-4867; Kanno et al (2000) J. of Biotechnology, 76:207-214; Chmura et al (2001) Proc. Nat. Acad. Sci. USA 98(15):8480-8484; U.S. Pat. No. 6,248,564). However, engineering in cysteine thiol groups by the mutation of various amino acid residues of a protein to cysteine amino acids is potentially problematic, particularly in the case of unpaired (free Cys) residues or those which are relatively accessible for reaction or oxidation. In concentrated solutions of the protein, whether in the periplasm of E. coli, culture supernatants, or partially or completely purified protein, unpaired Cys residues on the surface of the protein can pair and oxidize to form intermolecular disulfides, and hence protein dimers or multimers. Disulfide dimer formation renders the new Cys unreactive for conjugation to a drug, ligand, or other label. Furthermore, if the protein oxidatively forms an intramolecular disulfide bond between the newly engineered Cys and an existing Cys residue, both Cys thiol groups are unavailable for active site participation and interactions. Furthermore, the protein may be rendered inactive or non-specific, by misfolding or loss of tertiary structure (Zhang et al (2002) Anal. Biochem. 311:1-9).

Cysteine-engineered antibodies have been designed as FAB antibody fragments (thioFab) and expressed as full-length, IgG monoclonal (thioMab) antibodies (Junutula, J. R. et al. (2008) J Immunol Methods 332:41-52; US 2007/0092940, the contents of which are incorporated by reference). ThioFab and ThioMab antibodies have been conjugated through linkers at the newly introduced cysteine thiols with thiol-reactive linker reagents and drug-linker reagents to prepare antibody drug conjugates (Thio ADC).

All references cited herein, including patent applications and publications, are incorporated by reference in their entirety.

Polypeptides

Aspects of the invention include compositions that comprise a SPIK polypeptide, for example, an AS-SPIK polypeptide encoded by any one of the nucleic acid sequences of SEQ ID NOs: 104 and 105. The terms "peptide," "polypeptide," and "protein" are used interchangeably herein, although typically they refer to peptide sequences of varying sizes. We may refer to the amino acid-based compositions of the invention as "polypeptides" to convey that they are linear polymers of amino acid residues, and to help distinguish them from full-length proteins. A polypeptide in accordance with embodiments of the invention can "constitute" or "include" a fragment of an AS-SPIK polypeptide or an NS-SPIK polypeptide, and the invention encompasses polypeptides that constitute or include biologically active variants of an AS-SPIK polypeptide or an NS-SPIK polypeptide. It will be understood that the polypeptides can therefore include only a fragment of an AS-SPIK polypeptide or an NS-SPIK polypeptide (or a biologically active variant thereof) but may include additional residues as well. Biologically active variants will retain sufficient activity to inhibit proteases.

The bonds between the amino acid residues can be conventional peptide bonds or another covalent bond (such as an ester or ether bond), and the polypeptides can be modified by amidation, phosphorylation or glycosylation. A modification can affect the polypeptide backbone and/or one or more side chains. Chemical modifications can be naturally occurring modifications made in vivo following translation of an mRNA encoding the polypeptide (e.g., glycosylation in a bacterial host) or synthetic modifications made in vitro. A biologically active variant of an AS-SPIK polypeptide or an NS-SPIK polypeptide can include one or more structural modifications resulting from any combination of naturally occurring (i.e., made naturally in vivo) and with synthetic modifications (i.e., naturally occurring or non-naturally occurring modifications made in vitro). Examples of modifications include, but are not limited to, amidation (e.g., replacement of the free carboxyl group at the C-terminus by an amino group); biotinylation (e.g., acylation of lysine or other reactive amino acid residues with a biotin molecule); glycosylation (e.g., addition of a glycosyl group to either asparagines, hydroxylysine, serine or threonine residues to generate a glycoprotein or glycopeptide); acetylation (e.g., the addition of an acetyl group, typically at the N-terminus of a polypeptide); alkylation (e.g., the addition of an alkyl group); isoprenylation (e.g., the addition of an isoprenoid group); lipoylation (e.g. attachment of a lipoate moiety); and phosphorylation (e.g., addition of a phosphate group to serine, tyrosine, threonine or histidine).

One or more of the amino acid residues in a biologically active variant may be a non-naturally occurring amino acid residue. Naturally occurring amino acid residues include those naturally encoded by the genetic code as well as non-standard amino acids (e.g., amino acids having the D-configuration instead of the L-configuration). The present peptides can also include amino acid residues that are modified versions of standard residues (e.g. pyrrolysine can be used in place of lysine and selenocysteine can be used in place of cysteine). Non-naturally occurring amino acid residues are those that have not been found in nature, but that conform to the basic formula of an amino acid and can be incorporated into a peptide. These include D-alloisoleucine (2R,3S)-2-amino-3-methylpentanoic acid and L-cyclopentyl glycine (S)-2-amino-2-cyclopentyl acetic acid. For other examples, one can consult textbooks or the worldwide web (a site is currently maintained by the California Institute of Technology and displays structures of non-natural amino acids that have been successfully incorporated into functional proteins).

Alternatively, or in addition, one or more of the amino acid residues in a biologically active variant can be a naturally occurring residue that differs from the naturally occurring residue found in the corresponding position in a wildtype sequence. In other words, biologically active variants can include one or more, particularly one or two, amino acid substitutions. We may refer to a substitution, addition, or deletion of amino acid residues as a mutation of the wildtype sequence. As noted, the substitution can replace a naturally occurring amino acid residue with a non-naturally occurring residue or just a different naturally occurring residue. Further the substitution can constitute a conservative or non-conservative substitution. Conservative amino acid substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine.

The polypeptides that are biologically active variants of AS-SPIK can be characterized in terms of the extent to which their sequence is similar to or homologous to the corresponding wild-type polypeptide. For example, the sequence of a biologically active variant can be at least or about 80% homologous to (or identical to) corresponding residues in the wild-type polypeptide. For example, a biologically active variant of an AS-SPIK polypeptide or an NS-SPIK polypeptide can have an amino acid sequence with at least or about 80% sequence homology (e.g., at least or about 85%, 90%, 95%, 96%, 97%, 98%, or 99% sequence homology) (or the recited percentage identity) to an AS-SPIK or NS-SPIK polypeptide (SEQ ID NOs: 81, 82, 83) or to a homolog or ortholog thereof.

A biologically active variant of an AS-SPIK polypeptide or an NS-SPIK polypeptide will retain sufficient biological activity to be useful in the present methods. The biologically active variants will retain sufficient activity to function as an inhibitor of protease activity. The biological activity can be assessed in ways known to one of ordinary skill in the art and includes, without limitation, in vitro cleavage assays or functional assays.

Polypeptides can be generated by a variety of methods including, for example, recombinant techniques or chemical synthesis. Once generated, polypeptides can be isolated and purified to any desired extent. For example, one can use lyophilization following, for example, reversed phase (preferably) or normal phase HPLC, or size exclusion or partition chromatography on polysaccharide gel media such as Sephadex G-25. The composition of the final polypeptide may be confirmed by amino acid analysis after degradation of the peptide by standard means, by amino acid sequencing, or by FAB-MS techniques. Salts, including acid salts, esters, amides, and N-acyl derivatives of an amino group of a polypeptide may be prepared using methods known in the art, and such peptides are useful in the context of the present invention.

Also provided are AS-SPIK complexes. AS-SPIK complexes in accordance with embodiments of the invention comprise an antibody of the invention, as described herein, that specifically or preferentially binds to AS-SPIK, and an AS-SPIK polypeptide or fragment thereof. The fragment particularly has a length of at least 23 amino acids (SEQ ID NO: 81), preferably at least 10 amino acids, more preferred has at least the 7th through (and including) the 23th amino acids of SEQ ID NO: 81, even more preferred has at least the 8th through (and including) the 17th amino acids of SEQ ID NO: 81. The antibody can be any of the anti-AS-SPIK antibodies described above. The AS-SPIK polypeptide or fragment thereof can be AS-SPIK polypeptides or fragments thereof described above. In some embodiments, the antibody is an anti-AS-SPIK monoclonal antibody, IM-A1, IM-A6, IM-B10, IM-C6, IM-D3, IM-D5, IM-E2, IM-F5, IM-G6 and IM-G7 (VL and VH sequences listed in sequence data). In some embodiments, the AS-SPIK polypeptide is a polypeptide with an amino acid sequence having at least 98% homology to (or identity to) the amino acid sequence of SEQ ID NO: 82 or SEQ ID NO: 81. In some embodiments, the AS-SPIK polypeptide is a polypeptide having the amino acid sequence of SEQ ID NO: 82.

The specific binding of an anti-AS-SPIK antibody such as IM-A1, IM-A6, IM-B10, IM-C6, IM-D3, IM-D5, IM-E2, IM-F5, IM-G6 and IM-G7 can form an immune-complex with AS-SPIK or AS-SPIK peptide under certain conditions. The complex can be precipitated from solution for further analysis, for example, with a sandwich ELISA test. Using a 96-well plate immobilized with a second anti-SPIK antibody as a carrier, the immune complex can be caught by plate. The amount of AS-SPIK immune-complex formed can then be determined, if the antibodies in the complex are labeled with a reporter such as horseradish peroxidase (HPR). The AS-SPIK immune-complex also can be caught by agarose beads linking with protein A or G for western blot analysis.

Nucleic Acids

The terms "nucleic acid" and "polynucleotide" are used interchangeably herein to refer to both RNA and DNA, including cDNA, genomic DNA, synthetic DNA, and DNA (or RNA) containing nucleic acid analogs, any of which may encode a polypeptide of the invention and all of which are encompassed by the invention. Polynucleotides can have essentially any three-dimensional structure. A nucleic acid can be double-stranded or single-stranded (i.e., a sense strand or an antisense strand). Non-limiting examples of polynucleotides include genes, gene fragments, exons, introns, messenger RNA (mRNA) and portions thereof, transfer RNA, ribosomal RNA, siRNA, micro-RNA, ribozymes, cDNA, recombinant polynucleotides, branched polynucleotides, plasmids, vectors, isolated DNA of any sequence, isolated RNA of any sequence, nucleic acid probes, and primers, as well as nucleic acid analogs. In the context of the present invention, nucleic acids can encode a fragment of a naturally occurring AS-SPIK polypeptide or NS-SPIK polypeptide or a biologically active variant thereof. Non-limiting examples of nucleic acid sequences in accordance with embodiments of the invention include SEQ ID NOs: 104, 105 and 106, or a biologically active fragment or variant thereof. In some embodiments, a fragment can have a length of at least about 66 nucleotides, preferably at least about 54 nucleotides. In one preferred embodiment, a nucleic acid sequence comprises nucleotide residues 28-105 of SEQ ID NO: 105. In one preferred embodiment, a nucleic acid sequence comprises nucleotide residues 49-105 of SEQ ID NO: 105. Lu et al., Immunology 2011; 134(4):398-408.

An "isolated" nucleic acid can be, for example, a naturally-occurring DNA molecule or a fragment thereof, provided that at least one of the nucleic acid sequences normally found immediately flanking that DNA molecule in a naturally-occurring genome is removed or absent. Thus, an isolated nucleic acid includes, but is not limited to, a DNA molecule that exists as a separate molecule, independent of other sequences (e.g., a chemically synthesized nucleic acid, or a cDNA or genomic DNA fragment produced by the polymerase chain reaction (PCR) or restriction endonuclease treatment). An isolated nucleic acid also refers to a DNA molecule that is incorporated into a vector, an autonomously replicating plasmid, a virus, or into the genomic DNA of a prokaryote or eukaryote. In addition, an isolated nucleic acid can include an engineered nucleic acid such as a DNA molecule that is part of a hybrid or fusion nucleic acid. A nucleic acid existing among many (e.g., dozens, or hundreds to millions) of other nucleic acids within, for example, cDNA libraries or genomic libraries, or gel slices containing a genomic DNA restriction digest, is not an isolated nucleic acid.

Isolated nucleic acid molecules can be produced, for example, by polymerase chain reaction (PCR) techniques, which can be used to obtain an isolated nucleic acid containing a nucleotide sequence described herein, including nucleotide sequences encoding a polypeptide described herein. PCR can be used to amplify specific sequences from DNA as well as RNA, including sequences from total genomic DNA or total cellular RNA. Generally, sequence information from the ends of the region of interest or beyond is employed to design oligonucleotide primers that are identical or similar in sequence to opposite strands of the template to be amplified. Various PCR strategies also are available by which site-specific nucleotide sequence modifications can be introduced into a template nucleic acid.

Isolated nucleic acids also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >50-100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector. Isolated nucleic acids of the invention also can be obtained by mutagenesis of, e.g., a naturally occurring portion of an AS-SPIK- or NS-SPIK-encoding DNA (in accordance with, for example, the formula above).

Two nucleic acids or the polypeptides they encode may be described as having a certain degree of homology or identity to one another. For example, AS-SPIK polypeptide or an NS-SPIK polypeptide and a biologically active variant thereof may be described as exhibiting a certain degree of homology or identity. Alignments may be assembled by locating short AS-SPIK polypeptide or an NS-SPIK polypeptide sequences in the Protein Information Research (PIR) site (http://pir.georgetown.edu), followed by analysis with the "short nearly identical sequences" Basic Local Alignment Search Tool (BLAST) algorithm on the NCBI website (http://www.ncbi.nlm.nih.gov/blast).

To determine sequence homology or identity, a query nucleic acid or amino acid sequence can be aligned to one or more subject nucleic acid or amino acid sequences, respectively, using a computer program, such as, for example, BioEdit (version 4.8.5, North Carolina State University), which allows alignments of nucleic acid or protein sequences to be carried out across their entire length (global alignment), or ALIGN-2, as described above.

BioEdit calculates the best match between a query and one or more subject sequences and aligns them so that identities, similarities and differences can be determined. Gaps of one or more residues can be inserted into a query sequence, a subject sequence, or both, to maximize sequence alignments. For fast pair wise alignment of nucleic acid sequences, the following default parameters are used: word size: 2; window size: 4; scoring method: percentage; number of top diagonals: 4; and gap penalty: 5. For multiple alignments of nucleic acid sequences, the following parameters are used: gap opening penalty: 10.0; gap extension penalty: 5.0; and weight transitions: yes. For fast pair wise alignment of protein sequences, the following parameters are used: word size: 1; window size: 5; scoring method: percentage; number of top diagonals: 5; gap penalty: 3. For multiple alignment of protein sequences, the following parameters are used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; residue-specific gap penalties: on. The output is a sequence alignment that reflects the relationship between sequences.

To determine a percent homology between a query sequence and a subject sequence, BioEdit divides the number of identities in the best alignment by the number of residues compared (gap positions are excluded), and multiplies the result by 100. The output is the percent homology of the subject sequence with respect to the query sequence. It is noted that the percent homology value can be rounded to the nearest tenth. For example, 78.11, 78.12, 78.13, and 78.14 are rounded down to 78.1, while 78.15, 78.16, 78.17, 78.18, and 78.19 are rounded up to 78.2.

The nucleic acids and polypeptides described herein may be referred to as "exogenous." The term "exogenous" indicates that the nucleic acid or polypeptide is part of, or encoded by, a recombinant nucleic acid construct, or is not in its natural environment. For example, an exogenous nucleic acid can be a sequence from one species introduced into another species, i.e., a heterologous nucleic acid. Typically, such an exogenous nucleic acid is introduced into the other species via a recombinant nucleic acid construct. An exogenous nucleic acid can also be a sequence that is native to an organism and that has been reintroduced into cells of that organism. An exogenous nucleic acid that includes a native sequence can often be distinguished from the naturally occurring sequence by the presence of non-natural sequences linked to the exogenous nucleic acid, e.g., non-native regulatory sequences flanking a native sequence in a recombinant nucleic acid construct. In addition, stably transformed exogenous nucleic acids typically are integrated at positions other than the position where the native sequence is found.

Recombinant constructs are also provided herein and can be used to transform cells in order to express AS-SPIK. A recombinant nucleic acid construct comprises a nucleic acid encoding an AS-SPIK or NS-SPIK sequence operably linked to a regulatory region suitable for expressing the AS-SPIK or NS-SPIK in the particular cell. It will be appreciated that a number of nucleic acids can encode a polypeptide having a particular amino acid sequence. The degeneracy of the genetic code is well known in the art. For many amino acids, there is more than one nucleotide triplet that serves as the codon for the amino acid. For example, codons in the coding sequence for AS-SPIK or NS-SPIK can be modified such that optimal expression in a particular organism is obtained, using appropriate codon bias tables for that organism.

Vectors containing nucleic acids such as those described herein also are provided. A "vector" is a replicon, such as a plasmid, phage, or cosmid, into which another DNA segment may be inserted so as to bring about the replication of the inserted segment. Generally, a vector is capable of replication when associated with the proper control elements. Suitable vector backbones include, for example, those routinely used in the art such as plasmids, viruses, artificial chromosomes, BACs, YACs, or PACs. The term "vector" includes cloning and expression vectors, as well as viral vectors and integrating vectors. An "expression vector" is a vector that includes a regulatory region. A wide variety of host/expression vector combinations may be used to express the nucleic acid sequences described herein. Suitable expression vectors include, but are not limited to, plasmids and viral vectors derived from, for example, bacteriophage, baculoviruses, and retroviruses.

The vectors provided herein also can include, for example, origins of replication, scaffold attachment regions (SARs), and/or markers. A marker gene can confer a selectable phenotype on a host cell. For example, a marker can confer biocide resistance, such as resistance to an antibiotic (e.g., kanamycin, G418, bleomycin, or hygromycin). As noted above, an expression vector can include a tag sequence designed to facilitate manipulation or detection (e.g., purification or localization) of the expressed polypeptide. Tag sequences, such as green fluorescent protein (GFP), glutathione S-transferase (GST), polyhistidine, c-myc, hemagglutinin, or Flag™ tag (Kodak, New Haven, CT) sequences typically are expressed as a fusion with the encoded polypeptide. Such tags can be inserted anywhere within the polypeptide, including at either the carboxyl or amino terminus.

Additional expression vectors also can include, for example, segments of chromosomal, non-chromosomal and synthetic DNA sequences. Suitable vectors include derivatives of SV40 and known bacterial plasmids, e.g., *E. coli* plasmids col El, pCR1, pBR322, pMal-C2, pET, pGEX, pMB9 and their derivatives, plasmids such as RP4; phage DNAs, e.g., the numerous derivatives of phage 1, e.g., NM989, and other phage DNA, e.g., M13 and filamentous single stranded phage DNA; yeast plasmids such as the 2μ plasmid or derivatives thereof, vectors useful in eukaryotic cells, such as vectors useful in insect or mammalian cells; vectors derived from combinations of plasmids and phage DNAs, such as plasmids that have been modified to employ phage DNA or other expression control sequences.

The vector can also include a regulatory region. The term "regulatory region" refers to nucleotide sequences that influence transcription or translation initiation and rate, and stability and/or mobility of a transcription or translation product. Regulatory regions include, but are not limited to, promoter sequences, enhancer sequences, response elements, protein recognition sites, inducible elements, protein binding sequences, 5' and 3' untranslated regions (UTRs), transcriptional start sites, termination sequences, polyadenylation sequences, nuclear localization signals, and introns.

As used herein, the term "operably linked" refers to positioning of a regulatory region and a sequence to be transcribed in a nucleic acid so as to influence transcription or translation of such a sequence. For example, to bring a coding sequence under the control of a promoter, the translation initiation site of the translational reading frame of the polypeptide is typically positioned between one and about fifty nucleotides downstream of the promoter. A promoter can, however, be positioned as much as about 5,000 nucleotides upstream of the translation initiation site or about 2,000 nucleotides upstream of the transcription start site. A promoter typically comprises at least a core (basal) promoter. A promoter also may include at least one control element, such as an enhancer sequence, an upstream element or an upstream activation region (UAR). The choice of promoters to be included depends upon several factors, including, but not limited to, efficiency, selectability, inducibility, desired expression level, and cell- or tissue-preferential expression. It is a routine matter for one of skill in the art to modulate the expression of a coding sequence by appropriately selecting and positioning promoters and other regulatory regions relative to the coding sequence.

A vector comprising an AS-SPIK or NS-SPIK nucleic acid sequence can be formulated in such a way as to promote uptake by a cell, i.e., a prokaryotic or eukaryotic cell, for example, a mammalian cell. Useful vector systems and formulations are described above. In some embodiments the vector can deliver the compositions to a specific cell type. The invention is not so limited however, and other methods of DNA delivery such as chemical transfection, using, for example calcium phosphate, DEAE dextran, liposomes, lipoplexes, surfactants, and perfluoro chemical liquids are also contemplated, as are physical delivery methods, such as electroporation, micro injection, ballistic particles, and "gene gun" systems. In some embodiments, the polynucleotides of the invention may also be used with a microdelivery vehicle such as cationic liposomes, other lipid-containing complexes, and other macromolecular complexes capable of mediating delivery of a polynucleotide to a host cell. Another delivery method is to use single stranded DNA producing vectors which can produce the expressed products intracellularly.

Methods of Use

The compositions disclosed herein are generally and variously useful for the diagnosis and/or treatment of disorders that are characterized by the expression of AS-SPIK. Such disorders include, but are not limited to, cancers, viral infections, and inflammatory disorders. One prominent example is liver cancer. Other non-limiting examples include those cancers described herein in connection with the definition of the term "cancer". Accordingly, aspects of the invention involve methods for diagnosing and/or treating a cancer (e.g., a liver cancer) in a subject having a said cancer, or who is at risk for developing said cancer. The terms "subject", "patient", and "individual" are used interchangeably herein.

In some embodiments, the methods involve contacting a biological test sample from a subject with an AS-SPIK antibody or antigen-binding fragment to generate an AS-SPIK-antibody complex; detecting a concentration of the AS-SPIK-antibody complex in the biological test sample; and comparing the concentration of the AS-SPIK-antibody complex to a reference value to determine whether the subject has or is at risk of developing the disorder. In certain embodiments, the methods comprise contacting a biological test sample with a first antibody or antigen-binding fragment that binds to SPIK to generate a SPIK-antibody complex; contacting the SPIK-antibody complex with an AS-SPIK antibody or antigen-binding fragment to generate an AS-SPIK-antibody complex in the biological test sample; and comparing the concentration of the AS-SPIK-antibody complex to a reference value to determine whether the subject has or is at risk of developing the disorder. Several non-limiting examples of antibodies that can be utilized in such methods are described herein.

In some embodiments, the methods involve administering a therapeutically effective amount of an antibody, or antigen-binding fragment thereof, or antibody-drug conjugate, as described herein, to a patient suffering from a disease or disorder characterized by the expression of AS-SPIK.

Liver Cancer

One prominent example of a disorder that is characterized by expression of AS-SPIK is liver cancer. Liver cancer encompasses a wide range of conditions that result in damage to the liver or impaired liver function. Liver cancer can result, for example, from infectious agents, disease, trauma, or genetic conditions or a combination of infectious agents, disease, trauma, and genetic conditions.

Liver cancer can include diseases which involve abnormal cell growth, such as primary liver cancer, for example, hepatocellular carcinoma, cholangiocarcinoma, angiosarcoma, and hepatoblastoma. Such cancers can include cancers at any stage of disease progression, such as HCC from very early stages (Barcelona Clinic Liver Cancer system (BCLC) stages 0 and tumor size <2 cm), early stages (BCLC stage A, tumor size between 2 cm and 5 cm), middle stages (BCLC stage B, intermediate tumor size >5 cm), late stages (BCLC stage C and D, advanced stage), or metastatic stages, (Pons et al., *HPB* 2005; 7(1):35-41 and ICC from ICC early stages (Stage I, II and IIIa, tumor size <2 cm), middle stages (Stage IIIb and IIIc, tumor size ≥2 cm), and late stage (stage IV) (Farges et al., *Cancer* 2011; 117(10):2170-2177).

Liver cancer can also be induced by infectious diseases caused by viruses, such as Hepatitis B, Hepatitis C, and Hepatitis D. Regardless of the specific hepatitis virus, such infections can be either acute or chronic.

Liver cancer can also arise from liver damage, for example, liver cirrhosis. Cirrhosis, a late stage scarring or fibrosis of the liver, can be caused by many forms of liver diseases and conditions. Cirrhosis can occur as the result of genetic conditions, for example hemochromatosis, cystic fibrosis, Wilson's disease, and autoimmune disorders. Cirrhosis can also arise from hepatitis viral infections and alcohol consumption.

Liver cancer also can be caused by other diseases including, but are not limited to alcoholic liver disease, disorders related to abnormal fat content in the liver such as fatty liver, non-alcoholic fatty liver disease, non-alcoholic steatosis, and liver fibrosis.

Biological Samples

A "biological sample", "test sample" or "sample" refers to a sample obtained or derived from a patient. The sample can be, for example, a body fluid sample. Exemplary body fluid samples include blood, serum, plasma, urine, saliva, semen, stool, sputum, cerebral spinal fluid, tears, mucus, amniotic fluid, or any combination thereof. In some embodiments, a biological sample can be a tissue sample. Exemplary tissue samples include a biopsy specimen, such as a liver biopsy specimen, or a primary cell culture specimen prepared from a patient's cells, or supernatant from the primary culture.

Immunoassays

Aspects of the invention include diagnostic assay methods, e.g., diagnostic immunoassays, which can be used to detect the presence or absence of AS-SPIK in a test sample. The immunoassay format used for the detection of AS-SPIK can be configured in a variety of ways. The immunoassays can include both homogeneous and heterogeneous assays, competitive and non-competitive assays, direct and indirect assays, and "sandwich" assays. Useful formats include, but are not limited to, enzyme immunoassays, for example, enzyme linked immunosorbent assays (ELISA), chemiluminescent immune-assays (CLIA), electrochemiluminescent assays, radioimmunoassay, immunofluorescence, fluorescence anisotropy, immunoprecipitation, equilibrium dialysis, immunodiffusion, immunoblotting, agglutination, luminescent proximity assays, and nephelometry.

Regardless of the format, the biological sample is contacted with an anti-AS-SPIK antibody of the present invention. In some embodiments, the biological sample can be immobilized on a solid support. In some embodiments, the biological sample is contacted with an anti-SPIK antibody of the invention that has been immobilized on a solid support. The solid support can be, for example, a plastic surface, a glass surface, a paper or fibrous surface, or the surface of a particle. More specifically, the support can include a microplate, a bead, a polyvinylidene difluoride (PVDF) membrane, nitrocellulose membrane, nylon membrane, porous membranes, non-porous membranes. The composition of the substrate can be varied. For example, substrates or support can comprise glass, cellulose-based materials, thermoplastic polymers, such as polyethylene, polypropylene, or polyester, sintered structures composed of particulate materials (e.g., glass or various thermoplastic polymers), or cast membrane film composed of nitrocellulose, nylon, or polysulfone. In general embodiments, the substrate may be any surface or support upon which an antibody or a polypeptide can be immobilized, including one or more of a solid support (e.g., glass such as a glass slide or a coated plate, silica, plastic or derivatized plastic, paramagnetic or non-magnetic metal), a semi-solid support (e.g., a polymeric material, a gel, agarose, or other matrix), and/or a porous support (e.g., a filter, a nylon or nitrocellulose membrane or other membrane). In some embodiments, synthetic polymers can be used as a substrate, including, e.g., polystyrene, polypropylene, polyglycidylmethacrylate, aminated or carboxylated polystyrenes, polyacrylamides, polyamides, and polyvinyl-chlorides.

In some embodiments, the immunoassay format can be a two antibody "sandwich" assay. The biological sample is contacted with an anti-SPIK antibody of the invention that has been immobilized on a solid support, for example, microtiter plate. The sample and the first antibody are incubated under conditions that favor specific binding and the formation of a SPIK-antibody complex. Following the contacting step, unbound constituents of the biological sample are removed. Then, the complex is contacted with a second anti-SPIK antibody. The second antibody binds to a different SPIK epitope than the epitope bound by the first antibody. Thus, the first and second antibodies do not competitively inhibit one another for binding to SPIK. In some embodiments, the first antibody can recognize an epitope, i.e., an antigenic determinant, present on both AS-SPIK and NS-SPIK. We may refer to such an antibody as a "pan-SPIK" antibody. Alternatively, the first antibody can recognize an epitope present only on AS-SPIK. In some embodiments, the second antibody can recognize an epitope, i.e., an antigenic determinant, present on both AS-SPIK and NS-SPIK. Alternatively, the second antibody can recognize an epitope present only on AS-SPIK or NS-SPIK. Thus, the sandwich assay can be configured such that the first antibody is a pan-SPIK antibody and the second antibody specifically or preferentially binds to AS-SPIK and does not specifically bind to NS-SPIK. Alternatively, the sandwich assay can be configured such that both the first and second antibodies specifically or preferentially bind to AS-SPIK and do not specifically bind to NS-SPIK.

Antibody binding can be measured in a variety of ways. The signal, for example, generated by a detectable label, can be analyzed and, if applicable, quantified using an optical scanner or other image acquisition device and software that permits the measurement of the signal, for example a fluorescent signal a luminescent signal, or a phosphorescent signal, or a radioactive signal, associated with complex formation. Exemplary instrumentation for measuring a detectable signal can include, but is not limited to microplate readers, fluorimeters, spectrophotometers, and gamma counters.

Reference Samples

The level of AS-SPIK in a biological sample can be compared with that of a reference sample. Standard reference levels typically represent the average AS-SPIK levels derived from a population of individuals. The reference population may include individuals of similar age, body size, ethnic background or general health as the individual in question. Thus, the AS-SPIK levels in a patient's sample can be compared to values derived from: 1) individuals who are known to have a liver cancer and who express AS-SPIK and whose bodily fluids contain AS-SPIK; 2) individuals who do not have a liver cancer and whose bodily fluids contain low levels of AS-SPIK.

In general, an elevated level of AS-SPIK can be any level of AS-SPIK that is greater, preferably at least 1, 2, 3, 4 or 5% greater, more preferably at least 5% greater, than either the level of AS-SPIK found in a control sample or greater than the average level of AS-SPIK found in samples from a population of normal healthy individuals who do not have a liver cancer (reference value). A reduced level of AS-SPIK can be any level of AS-SPIK that is less than either the level of AS-SPIK found in a control sample or less than the average level of AS-SPIK found in samples from a population of individuals having a liver cancer. Any population size can be used to determine the average level of AS-SPIK found in samples from a population of normal healthy individuals. For example, a population of between 2 and 250, e.g., 2, 3, 4, 5, 10, 15, 20, 25, 30, 40, 50, 100, 150, 200, 250 or more individuals can be used to determine the average level of AS-SPIK in samples from a population of normal healthy individuals, with greater accuracy in the measurement coming from larger sample populations.

In some embodiments, a reference chart can be used to determine whether or not a particular level of AS-SPIK in a sample is elevated relative to a control sample or a larger population. For example, a reference chart can contain the normal range of AS-SPIK found in healthy individuals of the same age, ethnic background or general health as the individual in question. Using this reference chart, any level of AS-SPIK measured in a sample can be classified as being low, normal, or elevated relative to a control sample or relative to an average value derived from a larger population. The term "elevated level" is defined as a level, which is higher, preferably at least 2% higher, more preferably at least 5% higher, than a reference level.

Alternatively, or in addition, the level of AS-SPIK in a biological sample can be "normalized" against the level of one or more additional biological markers, for example another marker whose expression is independent of AS-SPIK expression. That is, the levels of the additional marker can be evaluated in parallel with those of AS-SPIK, either at the same time or on a separate occasion. The additional marker can serve as an internal control for sample preparation, handling and storage as well as day-to-day assay variability. The values for the level AS-SPIK and the additional marker may be expressed as a ratio and the ratio may be compared to similar ratio obtained for a reference sample or population. A useful second marker can be alpha-fetoprotein.

In some embodiments, the methods can include the use of a standard reference set. The reference set can include one or more samples of a purified SPIK polypeptide or fragment thereof. When multiple samples are used, these can be of different concentrations. In one embodiment, the reference set can include 6 samples of recombinant AS-SPIK at concentrations of 50 ng/ml, 30 ng/ml, 8 ng/ml, 3 ng/ml, 1 ng/ml and 0 ng/ml of AS-SPIK. The recombinant AS-SPIK can be purified with affinity chromatography (HPLC) using either anti-AS-SPIK antibody such as IM-CA22 or anti-tag antibodies. The reference value in blood or other body fluids can vary. However, the skilled person is in a position to determine the average level of AS-SPIK in the different body fluids of the respective populations and to determine a respective reference value, which assures that the level of AS-SPIK in patients having the liver cancer to be determined is well above the reference value, whereas the level of patients not suffering from a liver cancer to be detected or of healthy individuals is well below the respective reference value. In a preferred embodiment, the reference value is about 5%, more preferably about 7%, even more preferably about 10%, higher than the average level of AS-SPIK found in samples from a population of normal healthy individuals. It is noted that the levels of AS-SPIK in the biological sample and in the control sample are to be determined via the same method, so that comparability is given. The absolute values of e.g. AS-SPIK levels can be determined via calibration curves using recombinant AS-SPIK as described above.

Control Samples

In some embodiments, a positive control can include a sample of AS-SPIK produced by a eukaryotic cell or cell line. For example, a useful control can be medium containing 100 ng/ml of AS-SPIK from a stable cell line S2-3. This was created by the inventors by inserting the DNA sequence of AS-SPIK into the chromosomes of the HCC cells under the control of an artificial promotor which over-expressed AS-SPIK.

Methods disclosed herein are useful in the detection of a liver cancer in a patient suspected of having or at risk for a liver cancer. The methods can also be used in the analysis of samples from a patient who has been treated for a liver cancer, for example, hepatocellular carcinoma, in order to determine whether the patient is at risk for experiencing a remission of hepatocellular carcinoma. The methods can also be used for monitoring the course of the treatment, for example treatment with a therapeutic agent such as a small molecule drug or therapeutic antibody, chemotherapy, radiation therapy or surgery, to determine efficacy of the treatment and to allow to managing clinician to alter the treatment if needed. The methods may also be used in the detection, monitoring, or analysis of a patient suffering from or at risk for any disorder that is associated with a modulation, for example an increase, in the level of AS-SPIK in a biological sample, for example, a blood or serum sample, obtained from the patient.

The methods disclosed herein can be used in conjunction with other standard diagnostic methods, for example serological analyses of liver enzymes or alpha-fetoprotein, ultrasound (sonography), computed tomography (CT scan), magnetic resonance imaging (MRI), angiography, laparoscopy, or biopsy.

Articles of Manufacture

The compositions described herein can be packaged in suitable containers labeled, for example, for use in the detection, identification, and quantification of AS-SPIK in a biological sample. The articles of manufacture, also referred to as "kits", may include antibodies, antigen-binding fragments of antibodies, and/or antibody-drug conjugates of the present invention, media, purified samples of antigen for use as positive controls, or any combination thereof. The containers included in the kits can include a composition comprising an antibody of the present invention that specifically or preferentially binds to AS-SPIK but not to NS-SPIK. A kit can also include an antibody that binds to both AS-SPIK and NS-SPIK. Suitable buffers for diluting or reconstituting test samples and antibodies may also be provided. Some of the components may be provided in dry form, and may require reconstitution. The anti-SPIK antibody can be pre-bound to an assay device, for example, a microplate. Thus, in one embodiment, a kit for the detection, identification and quantification of AS-SPIK comprises an anti-AS-SPIK antibody and a pan-SPIK antibody. The kit may optionally comprise a detectable label.

Accordingly, packaged products (e.g., sterile containers containing one or more of the compositions described herein and packaged for storage, shipment, or sale at concentrated or ready-to-use concentrations) and kits, including at least one composition of the invention, e.g., an anti-AS-SPIK antibody, are also within the scope of the invention. A product can include a container (e.g., a vial, jar, bottle, bag, or the like) containing one or more compositions of the invention. In addition, an article of manufacture further may include, for example, packaging materials, instructions for use, syringes, delivery devices, buffers or other control reagents for treating or monitoring the condition for which diagnosis or treatment is required.

Reagents for particular types of assays can also be provided in kits of the invention. Thus, the kits can include a population of beads (e.g., suitable for an agglutination assay or a lateral flow assay), or a plate (e.g., a plate suitable for an ELISA assay). In other embodiments, the kits comprise a device, such as a lateral flow immunoassay device, an analytical rotor, or an electrochemical, optical, or opto-electronic sensor. The population of beads, the plate, and the devices are useful for performing an immunoassay. For example, they can be useful for detecting formation of a first agent-analyte-second agent complex.

In addition, the kits can include various diluents and buffers, labeled conjugates or other agents for the detection of specifically bound antigens or antibodies, and other signal-generating reagents, such as enzyme substrates, cofactors and chromogens. The kits can include one or more reference samples of varying concentrations, for example, purified recombinant AS-SPIK. The kits can also include a positive control, for example a cell supernatant from a cell line that over expresses AS-SPIK. Other components of a kit can include coating reagents, polyclonal or monoclonal capture antibodies specific for an antigen or analyte to be tested, or a cocktail of two or more of the antibodies, purified or semi-purified extracts of these antigens as standards, monoclonal antibody detector antibodies, an anti-mouse, anti-dog, anti-chicken, or anti-human antibody with indicator molecule conjugated thereto, indicator charts for colorimetric comparisons, disposable gloves, decontamination instructions, applicator sticks or containers, a sample preparatory cup, etc. In one embodiment, a kit comprises buffers or other reagents appropriate for constituting a reaction medium allowing the formation of a peptide-antibody complex.

Such kits provide a convenient, efficient way for a clinician to determine whether subject has or is at risk for a liver cancer. Thus, in certain embodiments, the kits further comprise instructions for use. The product may also include a legend (e.g., a printed label or insert or other medium describing the product's use (e.g., an audio- or videotape)). The legend can be associated with the container (e.g., affixed to the container) and can describe the manner in which the assay should be performed, indications therefor, and other uses.

The following examples are offered for illustrative purposes only, and are not intended to limit the scope of the present invention in any way. While several embodiments have been provided in the present disclosure, it should be understood that the disclosed compositions and methods might be embodied in many other specific forms without departing from the spirit or scope of the present disclosure. The present examples are to be considered as illustrative and not restrictive, and the intention is not to be limited to the details given herein. Various examples of changes, substitutions, and alterations are ascertainable by one skilled in the art and could be made without departing from the spirit and scope disclosed herein.

EXAMPLES

Example 1: Production of Rabbit Monoclonal Antibody Specific for AS-SPIK

Ten monoclonal antibodies described here were generated from rabbit. Briefly, rabbit were immunized with the recombinant AS-SPIK which contain different subsets of 23 extra amino acids (SEQ ID NO: 81). The blood was tested after three or four time imbursements by ELISA. Briefly, blood from immunized rabbits were reacted with plate coated with recombinant AS-SPIK. After washing, the color was developed by incubation of the plate with an anti-rabbit antibody labeled with HRP (horseradish peroxidase), and the optical density was measured after reaction with substrate TMB. The rabbit which is positive in test (produced antibody) was sacrificed. The monoclonal antibody was then established and further screened with ELISA using the plates immobilized with partially purified AS-SPIK from S2-3 cells, a cell line expresses high amount of AS-SPIK by integrated entire SPIK gene, Lu et. al *Tumor-associated protein SPIK/TATI suppresses serine protease dependent cell apoptosis, Apoptosis,* 2008 13(4), 483-494 and NS-SPIK from pancreatic cells. Finally, 10 monoclonal antibodies which strongly bind AS-SPIK but not NS-SPIK were selected. FIG. 1 shows 10 clones named I-A1, I-A6, IM-B10, IM-C6, IM-D3, IM-D5, IM-E2, IM-F5, IM-G6 and IM-G7 exhibit high binding activity to AS-SPIK, while their binding activity to NS-SPIK is just at background level as negative control (FIG. 1 Neg. Ctrl). This data suggests that the rabbit monoclonal antibodies identified herein solely recognize AS-SPIK. Furthermore, all of 10 antibodies can strongly bind to AS-SPIK and have similar binding affinity with AS-SPIK.

Example 2: Detection of Antibody-Antigen Complexes in Samples with IM-E2

The complex formed of antibody IM-A1, I-A6, IM-B10, IM-C6, IM-D3, IM-D5, IM-E2, IM-F5, IM-G6 and IM-G7 with AS-SPIK in medium of S2-3, medium of PanC1, serum of HCC patient and healthy person are measured with sandwich ELISA. Briefly, the immune-complex of antibodies with AS-SPIK in different samples were formed by incubation of antibody with the samples at 37° C. 0.5 hour. The mixture then reacted with the 96-well plate immobilized with polyclonal anti-SPIK antibody at 37° C. 1 hour. The plate then was incubated with anti-rabbit antibody labeled with HRP at 37° C. 45 minutes. The amount of antibody-antigen complex was determined by optical density after reaction with substrate TMB. FIG. 2 shows the test results from IM-E2. Similar results were achieved from other antibodies. The results clearly show that IM-E2 is able to form an antibody-antigen complex with AS-SPIK (FIG. 2; S2-3: OD (1.389)), but not NS-SPIK (FIG. 2, PanC1: OD (0.061)). The high OD (1.477) is also found in the serum of patients with HCC, but not in healthy person (healthy: OD (0.106)) suggests that the antibodies such as IM-E2 described here can be used for detecting serum AS-SPIK.

Example 3: The Sequence of Variable Heavy Chain and Variable Light Chain of Antibody and their CDRs The sequence of variable heavy chain (VH) and variable light chain (VL) of all 10 antibodies were determined. The CDRs of them then are identified. Table 1 shows the SEQ ID NOs of VH and VL of 10 antibodies: IM-A1, IM-A6, IM-B10, IM-C6, IM-D3, IM-D5, IM-E2, IM-F5, IM-G6 and IM-G7. Table 2 shows the SEQ ID NOs of VH CDRs of these 10 antibodies and Table 3 shows the SEQ ID NOs of VL CDRs of these 10 antibody.

TABLE 1

VH and VL SEQ ID NOs

| Antibody name | VH SEQ ID NO: | VL SEQ ID NO: |
| --- | --- | --- |
| A1 | 1 | 11 |
| A6 | 2 | 12 |
| B10 | 3 | 13 |
| C6 | 4 | 14 |
| D3 | 5 | 15 |
| D5 | 6 | 16 |
| E2 | 7 | 17 |
| F5 | 8 | 18 |
| G6 | 9 | 19 |

TABLE 1-continued

VH and VL SEQ ID NOs

| Antibody name | VH SEQ ID NO: | VL SEQ ID NO: |
|---|---|---|
| G7 | 10 | 20 |

TABLE 2

VH and HC CDR SEQ ID NOs

| Antibody name | VH SEQ ID NO: | VH CDR1 SEQ ID NO: | VH CDR2 SEQ ID NO: | VH CDR3 SEQ ID NO: |
|---|---|---|---|---|
| A1 | 1 | 21 | 31 | 41 |
| A6 | 2 | 22 | 32 | 42 |
| B10 | 3 | 23 | 33 | 43 |
| C6 | 4 | 24 | 34 | 44 |
| D3 | 5 | 25 | 35 | 45 |
| D5 | 6 | 26 | 36 | 46 |
| E2 | 7 | 27 | 37 | 47 |
| F5 | 8 | 28 | 38 | 48 |
| G6 | 9 | 29 | 39 | 49 |
| G7 | 10 | 30 | 40 | 50 |

TABLE 3

VL and LC CDR SEQ ID NOs

| Antibody name | VL SEQ ID NO: | VL CDR1 SEQ ID NO: | VL CDR2 SEQ ID NO: | VL CDR3 SEQ ID NO: |
|---|---|---|---|---|
| A1 | 11 | 51 | 61 | 71 |
| A6 | 12 | 52 | 62 | 72 |
| B10 | 13 | 53 | 63 | 73 |
| C6 | 14 | 54 | 64 | 74 |
| D3 | 15 | 55 | 65 | 75 |
| D5 | 16 | 56 | 66 | 76 |
| E2 | 17 | 57 | 67 | 77 |
| F5 | 18 | 58 | 68 | 78 |
| G6 | 19 | 59 | 69 | 79 |
| G7 | 20 | 60 | 70 | 80 |

Example 4: Consensus of VH and VL Sequences

The consensus of sequence was determined by alignment of entire sequence of VH and VL of 10 antibodies using program named BioEdit Sequence Alignment Editor, North Carolina University. The bottom line in FIG. 3 and FIG. 4 show that the sequence identity of these 10 antibodies, either in VH or in VL. Obviously, high similarity of sequence in VH and VL is existing in these 10 antibodies. The sequence identity of the 10 antibodies is between 85-95%.

Example 5: Consensus of CDR Sequences

The consensus of sequence of CDRs of variable heavy chain was determined using the software mentioned above. FIG. 5 shows that all 10 antibodies have high similarity of VH CDR1, the identity of them is from 66-100%. There is 66% similarity in VH CRD2 of 10 antibodies, the identity is from 50-66%. In contrast, there is very little similarity of VH CDR3 of these 10 antibodies. Only on amino-acid in VH CDR3 is identical in all 10 antibodies. The consensus sequence shows that there is more similarity of CDRs of VL than of VH in these 10 antibodies. There is 82% similarity in VL CDR1 of 10 antibodies, the identity of them is from 73-82% (FIG. 6). There is 86% similarity in VL CDR2 of 10 antibodies, the identity of them is from 72-86%. For VL CDR3, there is 75% similarity of 10 antibodies while the identity is from 45-75% (FIG. 6).

The invention claimed is:

1. An antibody or antigen-binding fragment thereof, that specifically binds to AS-SPIK (SEQ ID NO: 82), and does not bind to NS-SPIK (SEQ ID NO: 83), comprising:

(a) a CDRH1 sequence of SEQ ID NO: 21, a CDRH2 sequence of SEQ ID NO: 31, a CDRH3 sequence of SEQ ID NO: 41, a CDRL1 sequence of SEQ ID NO: 51, a CDRL2 sequence of SEQ ID NO: 61, and a CDRL3 sequence of SEQ ID NO: 71; or (b) a CDRH1 sequence of SEQ ID NO: 22, a CDRH2 sequence of SEQ ID NO: 32, a CDRH3 sequence of SEQ ID NO: 42, a CDRL1 sequence of SEQ ID NO: 52, a CDRL2 sequence of SEQ ID NO: 62, and a CDRL3 sequence of SEQ ID NO: 72; or (c) a CDRH1 sequence of SEQ ID NO: 23, a CDRH2 sequence of SEQ ID NO: 33, a CDRH3 sequence of SEQ ID NO: 43, a CDRL1 sequence of SEQ ID NO: 53, a CDRL2 sequence of SEQ ID NO: 63, and a CDRL3 sequence of SEQ ID NO: 73; or (d) a CDRH1 sequence of SEQ ID NO: 24, a CDRH2 sequence of SEQ ID NO: 34, a CDRH3 sequence of SEQ ID NO: 44, a CDRL1 sequence of SEQ ID NO: 54, a CDRL2 sequence of SEQ ID NO: 64, and a CDRL3 sequence of SEQ ID NO: 74; or (e) a CDRH1 sequence of SEQ ID NO: 25, a CDRH2 sequence of SEQ ID NO: 35, a CDRH3 sequence of SEQ ID NO: 45, a CDRL1 sequence of SEQ ID NO: 55, a CDRL2 sequence of SEQ ID NO: 65, and a CDRL3 sequence of SEQ ID NO: 75; or (f) a CDRH1 sequence of SEQ ID NO: 26, a CDRH2 sequence of SEQ ID NO: 36, a CDRH3 sequence of SEQ ID NO: 46, a CDRL1 sequence of SEQ ID NO: 56, a CDRL2 sequence of SEQ ID NO: 66, and a CDRL3 sequence of SEQ ID NO: 76; or (g) a CDRH1 sequence of SEQ ID NO: 27, a CDRH2 sequence of SEQ ID NO: 37, a CDRH3 sequence of SEQ ID NO: 47, a CDRL1 sequence of SEQ ID NO: 57, a CDRL2 sequence of SEQ ID NO: 67, and a CDRL3 sequence of SEQ ID NO: 77; or (h) a CDRH1 sequence of SEQ ID NO: 28, a CDRH2 sequence of SEQ ID NO: 38, a CDRH3 sequence of SEQ ID NO: 48, a CDRL1 sequence of SEQ ID NO: 58, a CDRL2 sequence of SEQ ID NO: 68, and a CDRL3 sequence of SEQ ID NO: 78; or (i) a CDRH1 sequence of SEQ ID NO: 29, a CDRH2 sequence of SEQ ID NO: 39, a CDRH3 sequence of SEQ ID NO: 49, a CDRL1 sequence of SEQ ID NO:

59, a CDRL2 sequence of SEQ ID NO: 69, and a CDRL3 sequence of SEQ ID NO: 79; or
(j) a CDRH1 sequence of SEQ ID NO: 30, a CDRH2 sequence of SEQ ID NO: 40, a CDRH3 sequence of SEQ ID NO: 50, a CDRL1 sequence of SEQ ID NO: 60, a CDRL2 sequence of SEQ ID NO: 70, and a CDRL3 sequence of SEQ ID NO: 80.

2. The antibody or antigen-binding fragment of claim 1, wherein the CDRH1, CDRH2, CDRH3, CDRL1, CDRL2, and CDRL3 sequences are present within a framework sequence.

3. The antibody or antigen-binding fragment of claim 2, wherein at least a portion of the framework sequence comprises a human consensus framework sequence.

4. The antibody or antigen-binding fragment of claim 3, comprising:
(a) a heavy chain variable region sequence having at least 95% sequence identity to SEQ ID NO: 1 and a light chain variable region sequence having at least 95% sequence identity to SEQ ID NO: 11; or
(b) a heavy chain variable region sequence having at least 95% sequence identity to SEQ ID NO: 2 and a light chain variable region sequence having at least 95% sequence identity to SEQ ID NO: 12; or
(c) a heavy chain variable region sequence having at least 95% sequence identity to SEQ ID NO: 3 and a light chain variable region sequence having at least 95% sequence identity to SEQ ID NO: 13; or
(d) a heavy chain variable region sequence having at least 95% sequence identity to SEQ ID NO: 4 and a light chain variable region sequence having at least 95% sequence identity to SEQ ID NO: 14; or
(e) a heavy chain variable region sequence having at least 95% sequence identity to SEQ ID NO: 5 and a light chain variable region sequence having at least 95% sequence identity to SEQ ID NO: 15; or
(f) a heavy chain variable region sequence having at least 95% sequence identity to SEQ ID NO: 6 and a light chain variable region sequence having at least 95% sequence identity to SEQ ID NO: 16; or
(g) a heavy chain variable region sequence having at least 95% sequence identity to SEQ ID NO: 7 and a light chain variable region sequence having at least 95% sequence identity to SEQ ID NO: 17; or
(h) a heavy chain variable region sequence having at least 95% sequence identity to SEQ ID NO: 8 and a light chain variable region sequence having at least 95% sequence identity to SEQ ID NO: 18; or
(i) a heavy chain variable region sequence having at least 95% sequence identity to SEQ ID NO: 9 and a light chain variable region sequence having at least 95% sequence identity to SEQ ID NO: 19; or
(j) a heavy chain variable region sequence having at least 95% sequence identity to SEQ ID NO: 10 and a light chain variable region sequence having at least 95% sequence identity to SEQ ID NO: 20.

5. The antibody or antigen-binding fragment of claim 4, comprising:
(a) a heavy chain variable region sequence of SEQ ID NO: 1 and a light chain variable region sequence of SEQ ID NO: 11; or
(b) a heavy chain variable region sequence of SEQ ID NO: 2 and a light chain variable region sequence of SEQ ID NO: 12; or
(c) a heavy chain variable region sequence of SEQ ID NO: 3 and a light chain variable region sequence of SEQ ID NO: 13; or
(d) a heavy chain variable region sequence of SEQ ID NO: 4 and a light chain variable region sequence of SEQ ID NO: 14; or
(e) a heavy chain variable region sequence of SEQ ID NO: 5 and a light chain variable region sequence of SEQ ID NO: 15; or
(f) a heavy chain variable region sequence of SEQ ID NO: 6 and a light chain variable region sequence of SEQ ID NO: 16; or
(g) a heavy chain variable region sequence of SEQ ID NO: 7 and a light chain variable region sequence of SEQ ID NO: 17; or
(h) a heavy chain variable region sequence of SEQ ID NO: 8 and a light chain variable region sequence of SEQ ID NO: 18; or
(i) a heavy chain variable region sequence of SEQ ID NO: 9 and a light chain variable region sequence of SEQ ID NO: 19; or
(j) a heavy chain variable region sequence of SEQ ID NO: 10 and a light chain variable region sequence of SEQ ID NO: 20.

6. The antibody or antigen-binding fragment of claim 1, which is multispecific.

7. The antibody or antigen-binding fragment of claim 1, which is bispecific.

8. The antibody or antigen-binding fragment of claim 1, which is monoclonal.

9. A diagnostic method for determining whether a subject has or is at risk of developing a disorder characterized by expression of AS-SPIK, the method comprising:
(a) contacting a biological test sample from the subject with an anti-AS-SPIK antibody, or an antigen-binding fragment thereof, that specifically binds to AS-SPIK (SEQ ID NO: 82), and does not bind to NS-SPIK (SEQ ID NO: 83), to generate an AS-SPIK-antibody complex, wherein the anti-AS-SPIK antibody or antigen-binding fragment thereof comprises:
(i) a CDRH1 sequence of SEQ ID NO: 21, a CDRH2 sequence of SEQ ID NO: 31, a CDRH3 sequence of SEQ ID NO: 41, a CDRL1 sequence of SEQ ID NO: 51, a CDRL2 sequence of SEQ ID NO: 61, and a CDRL3 sequence of SEQ ID NO: 71; or
(ii) a CDRH1 sequence of SEQ ID NO: 22, a CDRH2 sequence of SEQ ID NO: 32, a CDRH3 sequence of SEQ ID NO: 42, a CDRL1 sequence of SEQ ID NO: 52, a CDRL2 sequence of SEQ ID NO: 62, and a CDRL3 sequence of SEQ ID NO: 72; or
(iii) a CDRH1 sequence of SEQ ID NO: 23, a CDRH2 sequence of SEQ ID NO: 33, a CDRH3 sequence of SEQ ID NO: 43, a CDRL1 sequence of SEQ ID NO: 53, a CDRL2 sequence of SEQ ID NO: 63, and a CDRL3 sequence of SEQ ID NO: 73; or
(iv) a CDRH1 sequence of SEQ ID NO: 24, a CDRH2 sequence of SEQ ID NO: 34, a CDRH3 sequence of SEQ ID NO: 44, a CDRL1 sequence of SEQ ID NO: 54, a CDRL2 sequence of SEQ ID NO: 64, and a CDRL3 sequence of SEQ ID NO: 74; or
(v) a CDRH1 sequence of SEQ ID NO: 25, a CDRH2 sequence of SEQ ID NO: 35, a CDRH3 sequence of SEQ ID NO: 45, a CDRL1 sequence of SEQ ID NO: 55, a CDRL2 sequence of SEQ ID NO: 65, and a CDRL3 sequence of SEQ ID NO: 75; or
(vi) a CDRH1 sequence of SEQ ID NO: 26, a CDRH2 sequence of SEQ ID NO: 36, a CDRH3 sequence of SEQ ID NO: 46, a CDRL1 sequence of SEQ ID NO: 56, a CDRL2 sequence of SEQ ID NO: 66, and a CDRL3 sequence of SEQ ID NO: 76; or (vii) a CDRH1 sequence of SEQ ID NO: 27, a CDRH2 sequence of SEQ ID NO: 37, a CDRH3 sequence of SEQ ID NO: 47, a CDRL1 sequence of SEQ ID NO: 57, a CDRL2 sequence of SEQ ID NO: 67, and a CDRL3 sequence of SEQ ID NO: 77; or (viii) a CDRH1 sequence of SEQ ID NO: 28, a CDRH2 sequence of SEQ ID NO: 38, a CDRH3 sequence of SEQ ID NO: 48, a CDRL1 sequence of SEQ ID NO: 58, a CDRL2 sequence of SEQ ID NO: 68, and a CDRL3 sequence of SEQ ID NO: 78; or (ix) a CDRH1 sequence of SEQ ID NO: 29, a CDRH2 sequence of SEQ ID NO: 39, a CDRH3 sequence of SEQ ID NO: 49, a CDRL1 sequence of SEQ ID NO: 59, a CDRL2 sequence of SEQ ID NO: 69, and a CDRL3 sequence of SEQ ID NO: 79; or (x) a CDRH1 sequence of SEQ ID NO: 30, a CDRH2 sequence of SEQ ID NO: 40, a CDRH3 sequence of SEQ ID NO: 50, a CDRL1 sequence of SEQ ID NO: 60, a CDRL2 sequence of SEQ ID NO: 70, and a CDRL3 sequence of SEQ ID NO: 80;

(b) detecting a concentration of the AS-SPIK-antibody complex in the biological test sample; and (c) comparing the concentration of the AS-SPIK-antibody complex to a reference value to determine whether the subject has or is at risk of developing the disorder.

10. The diagnostic method of claim 9, wherein the anti-AS-SPIK antibody or antigen-binding fragment thereof comprises a detectable label.

11. The diagnostic method of claim 9, wherein the disorder is a liver disorder.

12. The diagnostic method of claim 11, wherein the liver disorder is hepatocellular carcinoma.

13. The diagnostic method of claim 11, wherein the liver disorder is intrahepatic cholangiocarcinoma.

14. The diagnostic method of claim 11, wherein the liver disorder is a viral infection of the liver.

15. The diagnostic method of claim 11, wherein the liver disorder is an inflammatory liver disorder.

16. The diagnostic method of claim 15, wherein the inflammatory liver disorder is cirrhosis of the liver.

17. A kit comprising an anti-AS-SPIK antibody, or an antigen-binding fragment thereof, that specifically binds to AS-SPIK (SEQ ID NO: 82), and does not bind to NS-SPIK (SEQ ID NO: 83), comprising:

(a) a CDRH1 sequence of SEQ ID NO: 21, a CDRH2 sequence of SEQ ID NO: 31, a CDRH3 sequence of SEQ ID NO: 41, a CDRL1 sequence of SEQ ID NO: 51, a CDRL2 sequence of SEQ ID NO: 61, and a CDRL3 sequence of SEQ ID NO: 71; or (b) a CDRH1 sequence of SEQ ID NO: 22, a CDRH2 sequence of SEQ ID NO: 32, a CDRH3 sequence of SEQ ID NO: 42, a CDRL1 sequence of SEQ ID NO: 52, a CDRL2 sequence of SEQ ID NO: 62, and a CDRL3 sequence of SEQ ID NO: 72; or (c) a CDRH1 sequence of SEQ ID NO: 23, a CDRH2 sequence of SEQ ID NO: 33, a CDRH3 sequence of SEQ ID NO: 43, a CDRL1 sequence of SEQ ID NO: 53, a CDRL2 sequence of SEQ ID NO: 63, and a CDRL3 sequence of SEQ ID NO: 73; or (d) a CDRH1 sequence of SEQ ID NO: 24, a CDRH2 sequence of SEQ ID NO: 34, a CDRH3 sequence of SEQ ID NO: 44, a CDRL1 sequence of SEQ ID NO: 54, a CDRL2 sequence of SEQ ID NO: 64, and a CDRL3 sequence of SEQ ID NO: 74; or (e) a CDRH1 sequence of SEQ ID NO: 25, a CDRH2 sequence of SEQ ID NO: 35, a CDRH3 sequence of SEQ ID NO: 45, a CDRL1 sequence of SEQ ID NO: 55, a CDRL2 sequence of SEQ ID NO: 65, and a CDRL3 sequence of SEQ ID NO: 75; or (f) a CDRH1 sequence of SEQ ID NO: 26, a CDRH2 sequence of SEQ ID NO: 36, a CDRH3 sequence of SEQ ID NO: 46, a CDRL1 sequence of SEQ ID NO: 56, a CDRL2 sequence of SEQ ID NO: 66, and a CDRL3 sequence of SEQ ID NO: 76; or (g) a CDRH1 sequence of SEQ ID NO: 27, a CDRH2 sequence of SEQ ID NO: 37, a CDRH3 sequence of SEQ ID NO: 47, a CDRL1 sequence of SEQ ID NO: 57, a CDRL2 sequence of SEQ ID NO: 67, and a CDRL3 sequence of SEQ ID NO: 77; or (h) a CDRH1 sequence of SEQ ID NO: 28, a CDRH2 sequence of SEQ ID NO: 38, a CDRH3 sequence of SEQ ID NO: 48, a CDRL1 sequence of SEQ ID NO: 58, a CDRL2 sequence of SEQ ID NO: 68, and a CDRL3 sequence of SEQ ID NO: 78; or (i) a CDRH1 sequence of SEQ ID NO: 29, a CDRH2 sequence of SEQ ID NO: 39, a CDRH3 sequence of SEQ ID NO: 49, a CDRL1 sequence of SEQ ID NO: 59, a CDRL2 sequence of SEQ ID NO: 69, and a CDRL3 sequence of SEQ ID NO: 79; or (j) a CDRH1 sequence of SEQ ID NO: 30, a CDRH2 sequence of SEQ ID NO: 40, a CDRH3 sequence of SEQ ID NO: 50, a CDRL1 sequence of SEQ ID NO: 60, a CDRL2 sequence of SEQ ID NO: 70, and a CDRL3 sequence of SEQ ID NO: 80.

18. The kit of claim 17, further comprising an antibody or antigen-binding fragment thereof that specifically binds to SPIK.

19. The kit of claim 17, further comprising an antibody or antigen-binding fragment thereof that specifically binds to both AS-SPIK and NS-SPIK.

20. The kit of claim 17, wherein the antibody or antigen-binding fragment thereof that specifically binds to AS-SPIK, and does not bind to NS-SPIK, is pre-bound to an assay device.

* * * * *